US012746068B2

(12) United States Patent
Roche et al.

(10) Patent No.: US 12,746,068 B2
(45) Date of Patent: Sep. 29, 2026

(54) METHODS AND SYSTEMS FOR UTILIZING RADIOMIC-BASED MEASUREMENTS WITHIN A CLINICAL DECISION SUPPORT TOOL

(71) Applicant: Advita Ortho, LLC, Gainesville, FL (US)

(72) Inventors: Christopher Roche, Gainesville, FL (US); Josie Elwell, Fayetteville, NY (US); Vikas Kumar, Seattle, WA (US); Hamidreza Rajabzadeh-Oghaz, Bothell, WA (US)

(73) Assignee: Advita Ortho, LLC, Gainesville, FL (US)

( * ) Notice: Subject to any disclaimer, the term of this patent is extended or adjusted under 35 U.S.C. 154(b) by 0 days.

(21) Appl. No.: 19/462,437

(22) Filed: Jan. 28, 2026

(65) Prior Publication Data

US 2026/0224286 A1 Aug. 6, 2026

Related U.S. Application Data

(60) Provisional application No. 63/750,974, filed on Jan. 29, 2025.

(51) Int. Cl.
*A61B 34/10* (2016.01)
*A61F 2/46* (2006.01)
(Continued)

(52) U.S. Cl.
CPC ............ *A61B 34/10* (2016.02); *A61F 2/4612* (2013.01); *G06T 3/40* (2013.01); *G06T 5/77* (2024.01);
(Continued)

(58) Field of Classification Search
CPC .............. A61B 2034/105; A61B 34/25; A61B 2034/108; A61B 34/10; A61B 2034/256;
(Continued)

(56) References Cited

U.S. PATENT DOCUMENTS

| | | | | |
|---|---|---|---|---|
| 2012/0232592 A1* | 9/2012 | Massoudi | .......... | A61B 17/7068 606/279 |
| 2013/0245695 A1* | 9/2013 | Bordeaux | .......... | A61B 17/8066 606/280 |

(Continued)

FOREIGN PATENT DOCUMENTS

WO 2024054584 A1 3/2024

OTHER PUBLICATIONS

International Search Report and Written Opinion from International PCT Application No. PCT/US2026/012892 dated Mar. 27, 2026.

*Primary Examiner* — Ajibola A Akinyemi
(74) *Attorney, Agent, or Firm* — GREENBERG TRAURIG, LLP

(57) ABSTRACT

A method and system for pre-surgical joint analysis for arthroplasty treatment are disclosed. A processor receives image data of medical images of a portion of a joint acquired from a medical imaging device prior to implantation. The processor generates pixel-voxel granularity (PVG) corrected images by applying a PVG pre-processing algorithm that normalizes gray-level intensities to a common scale, resamples to a standard voxel size to increase or decrease voxels between images, and quantizes pixel values to produce PVG corrected images. The processor segments the PVG corrected images using a segmentation algorithm to identify region of interest associated with bone, connective tissue, and/or muscle. The processor inputs the regions of interest and PVG corrected images into a medical image analysis machine model trained to output image based measurements (Continued)

and an implant complication risk assessment and displays a 3D representation of the joint and the implant complication risk assessment to a user.

30 Claims, 47 Drawing Sheets

(51) Int. Cl.

| | |
|---|---|
| ***G06T 3/40*** | (2006.01) |
| ***G06T 5/77*** | (2024.01) |
| ***G06T 7/00*** | (2017.01) |
| ***G06T 7/11*** | (2017.01) |
| ***G16H 30/40*** | (2018.01) |
| ***G16H 50/20*** | (2018.01) |
| *G16H 10/60* | (2018.01) |

(52) U.S. Cl.
CPC .............. *G06T 7/0014* (2013.01); *G06T 7/11* (2017.01); *G16H 30/40* (2018.01); *G16H 50/20* (2018.01); *A61B 2034/108* (2016.02); *A61F 2002/4633* (2013.01); *G06T 2207/10081* (2013.01); *G06T 2207/20076* (2013.01); *G06T 2207/20084* (2013.01); *G06T 2207/30008* (2013.01); *G16H 10/60* (2018.01)

(58) Field of Classification Search
CPC . A61B 34/20; A61B 2034/102; A61B 5/1122; A61B 5/1126; A61B 5/742; A61B 2562/0252; A61B 2562/04
USPC .......................................................... 382/128
See application file for complete search history.

(56) References Cited

U.S. PATENT DOCUMENTS

2014/0093153 A1* 4/2014 Sofka .................... G06T 7/0014 382/131
2021/0217164 A1 7/2021 Weese
2021/0304361 A1 9/2021 Huemmer
2021/0330389 A1 10/2021 Varadarajan

* cited by examiner

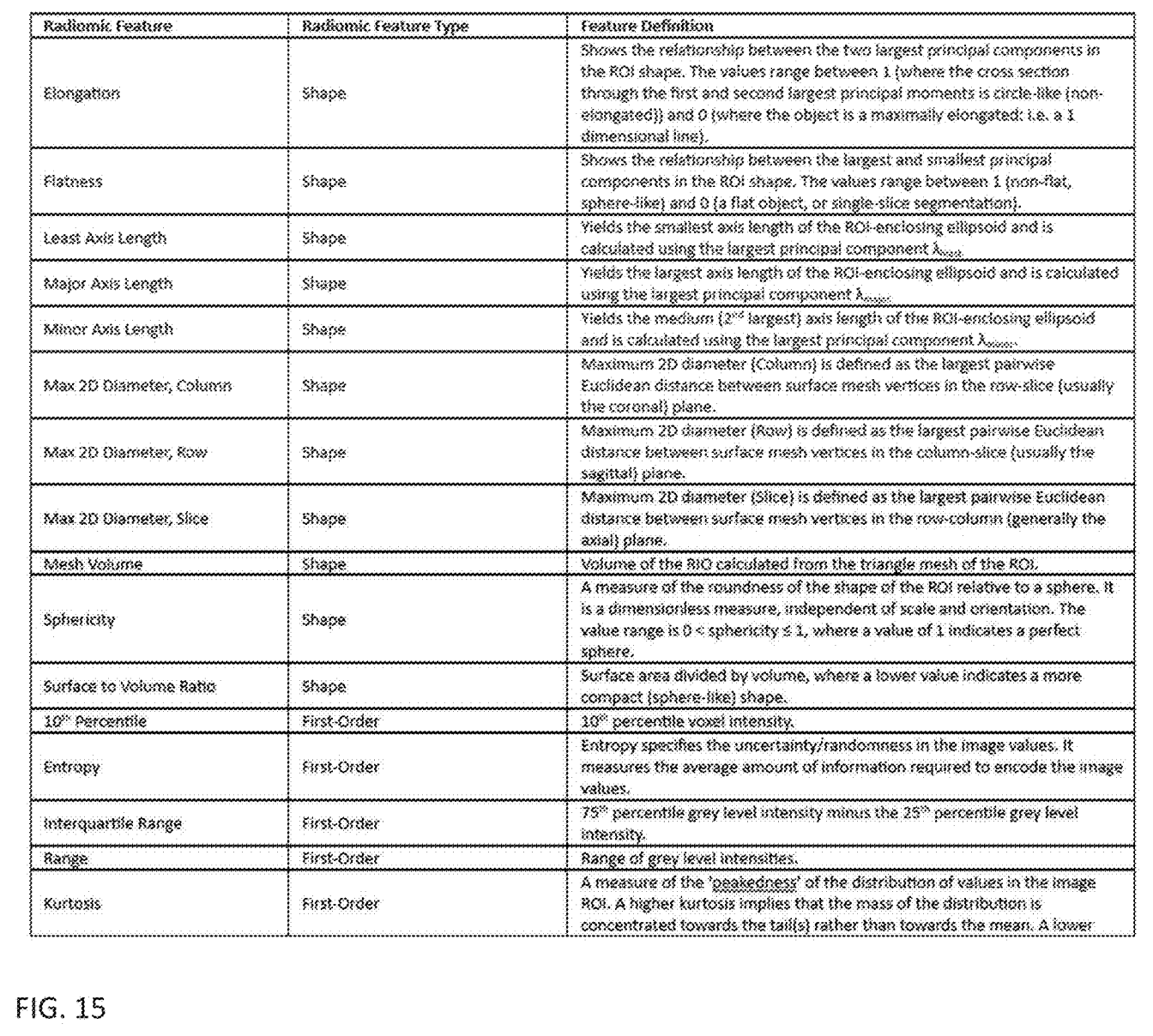

| Radiomic Feature | Radiomic Feature Type | Feature Definition |
|---|---|---|
| Elongation | Shape | Shows the relationship between the two largest principal components in the ROI shape. The values range between 1 (where the cross section through the first and second largest principal moments is circle-like (non-elongated)) and 0 (where the object is a maximally elongated: i.e. a 1 dimensional line). |
| Flatness | Shape | Shows the relationship between the largest and smallest principal components in the ROI shape. The values range between 1 (non-flat, sphere-like) and 0 (a flat object, or single-slice segmentation). |
| Least Axis Length | Shape | Yields the smallest axis length of the ROI-enclosing ellipsoid and is calculated using the largest principal component $\lambda$[illegible]. |
| Major Axis Length | Shape | Yields the largest axis length of the ROI-enclosing ellipsoid and is calculated using the largest principal component $\lambda$[illegible]. |
| Minor Axis Length | Shape | Yields the medium (2nd largest) axis length of the ROI-enclosing ellipsoid and is calculated using the largest principal component $\lambda$[illegible]. |
| Max 2D Diameter, Column | Shape | Maximum 2D diameter (Column) is defined as the largest pairwise Euclidean distance between surface mesh vertices in the row-slice (usually the coronal) plane. |
| Max 2D Diameter, Row | Shape | Maximum 2D diameter (Row) is defined as the largest pairwise Euclidean distance between surface mesh vertices in the column-slice (usually the sagittal) plane. |
| Max 2D Diameter, Slice | Shape | Maximum 2D diameter (Slice) is defined as the largest pairwise Euclidean distance between surface mesh vertices in the row-column (generally the axial) plane. |
| Mesh Volume | Shape | Volume of the RIO calculated from the triangle mesh of the ROI. |
| Sphericity | Shape | A measure of the roundness of the shape of the ROI relative to a sphere. It is a dimensionless measure, independent of scale and orientation. The value range is $0 < \text{sphericity} \leq 1$, where a value of 1 indicates a perfect sphere. |
| Surface to Volume Ratio | Shape | Surface area divided by volume, where a lower value indicates a more compact (sphere-like) shape. |
| 10th Percentile | First-Order | 10th percentile voxel intensity. |
| Entropy | First-Order | Entropy specifies the uncertainty/randomness in the image values. It measures the average amount of information required to encode the image values. |
| Interquartile Range | First-Order | 75th percentile grey level intensity minus the 25th percentile grey level intensity. |
| Range | First-Order | Range of grey level intensities. |
| Kurtosis | First-Order | A measure of the 'peakedness' of the distribution of values in the image ROI. A higher kurtosis implies that the mass of the distribution is concentrated towards the tail(s) rather than towards the mean. A lower |

FIG. 15

| | | |
|---|---|---|
| | | kurtosis implies the reverse: that the mass of the distribution is concentrated towards a spike near the Mean value. |
| Maximum | First-Order | Maximum grey level intensity. |
| Mean | First-Order | Mean grey level intensity. |
| Minimum | First-Order | Minimum grey level intensity. |
| Skewness | First-Order | Measures the asymmetry of the distribution of values about the mean value. Depending on where the tail is elongated and the mass of the distribution is concentrated, this value can be positive or negative. |
| Autocorrelation | Second-Order/Texture (GLCM) | A measure of the magnitude of the fineness and coarseness of texture. |
| Cluster Tendency | Second-Order/Texture (GLCM) | A measure of groupings of voxels with similar gray-level values. |
| Contrast | Second-Order/Texture (GLCM) | A measure of the local intensity variation, favoring values away from the diagonal (i=j). A larger value correlates with a greater disparity in intensity values among neighboring voxels. |
| Correlation | Second-Order/Texture (GLCM) | A value between 0 (uncorrelated) and 1 (perfectly correlated) showing the linear dependency of gray level values to their respective voxels in the GLCM. |
| Id | Second-Order/Texture (GLCM) | A measure of the local homogeneity of an image. With more uniform gray levels, the denominator will remain low, resulting in a higher overall value. |
| Joint Energy | Second-Order/Texture (GLCM) | A measure of homogeneous patterns in the image. A greater Energy implies that there are more instances of intensity value pairs in the image that neighbor each other at higher frequencies. |
| Joint Entropy | Second-Order/Texture (GLCM) | A measure of the randomness/variability in neighborhood intensity values. |
| Maximum Probability | Second-Order/Texture (GLCM) | A measure of occurrences of the most predominant pair of neighboring intensity values. |
| Maximal Correlation Coefficient (MCC) | Second-Order/Texture (GLCM) | A measure of complexity of the texture and $0 \leq MCC \leq 1$. |
| Sum Entropy | Second-Order/Texture (GLCM) | Specifies the uncertainty/randomness in the image values. |
| Dependence Entropy | Second-Order/Texture (GLDM) | $-\sum_{i=1}^{N_g}\sum_{j=1}^{N_d} p(i,j)\log_2(p(i,j)+\epsilon)$ |
| Dependence Variance | Second-Order/Texture (GLDM) | A measure of the variance in dependence size in the image. |
| Gray Level Variance | Second-Order/Texture (GLDM) | A measure of the variance in gray level intensities for the zones. |
| Large Dependence High Gray Level Emphasis | Second-Order/Texture (GLDM) | A measure of the joint distribution of large dependence with higher gray-level values. |
| Large Dependence Low Gray Level Emphasis | Second-Order/Texture (GLDM) | A measure of the joint distribution of large dependence with lower gray-level values. |
| Low Gray Level Emphasis | Second-Order/Texture (GLDM) | A measure of the distribution of low gray-level values, with a higher value indicating a greater concentration of low gray-level values in the image. |
| Small Dependence Low Gray Level Emphasis | Second-Order/Texture (GLDM) | A measure of the joint distribution of small dependence with lower gray-level values. |
| Run Entropy | Second-Order/Texture (GLRLM) | A measure of the uncertainty/randomness in the distribution of run lengths and gray levels. A higher value indicates more heterogeneity in the texture patterns. |

FIG. 15 (CONT'D)

| | | |
|---|---|---|
| Gray Level Non-Uniformity Normalized | Second-Order/Texture (GLSZM) | A measure of the variability of gray-level intensity values in the image, with a lower value indicating a greater similarity in intensity values. |
| Gray Level Variance | Second-Order/Texture (GLSZM) | A measure of the variance in grey level in the image. |
| Size-Zone Non-Uniformity Normalized | Second-Order/Texture (GLSZM) | A measure of the variability of size zone volumes in the image, with a lower value indicating more homogeneity in size zone volumes. |
| Low Gray Level Zone Emphasis | Second-Order/Texture (GLSZM) | A measure of the distribution of lower gray-level size zones, with a higher value indicating a greater proportion of lower gray-level values and size zones in the image. |
| Zone Entropy | Second-Order/Texture (GLSZM) | A measure of the uncertainty/randomness in the distribution of zone sizes and gray levels. A higher value indicates more heterogeneity in the texture patterns. |
| Courseness | Second-Order/Texture (NGTDM) | A measure of average difference between the center voxel and its neighborhood and is an indication of the spatial rate of change. A higher value indicates a lower spatial change rate and a locally more uniform texture. |
| Strength | Second-Order/Texture (NGTDM) | A measure of the primitives in an image. Its value is high when the primitives are easily defined and visible, i.e. an image with slow change in intensity but more large coarse differences in gray level intensities. |

FIG. 15 (CONT'D)

| Method # | Spatial Resampling (Voxel Size, mm) | Interpolation Method | Intensity Discretization (Bin Count, # of Gray Levels) | Normalization? |
|---|---|---|---|---|
| #1 (Baseline) | 1.0x1.0x1.0 | WelchSinc | 40 | Yes |
| #2 | 1.5x1.5x1.5 | WelchSinc | 40 | Yes |
| #3 | 0.5x0.5x0.5 | WelchSinc | 40 | Yes |
| #4 | 1.0x1.0x1.0 | BSpline | 40 | Yes |
| #5 | 1.0x1.0x1.0 | WelchSinc | 60 | Yes |
| #6 | 1.0x1.0x1.0 | WelchSinc | 80 | Yes |
| #7 | 1.0x1.0x1.0 | WelchSinc | 40 | Yes (voxel array shift of 1000) |

FIG. 16

| Radiomic Feature | Radiomic Feature Type | ICC |
|---|---|---|
| Deltoid Elongation | Shape | 1.0 |
| Deltoid Flatness | Shape | 1.0 |
| Deltoid Least Axis Length | Shape | 1.0 |
| Deltoid Major Axis Length | Shape | 1.0 |
| Deltoid Max 2D Diameter, Column | Shape | 1.0 |
| Deltoid Max 2D Diameter, Row | Shape | 1.0 |
| Deltoid Max 2D Diameter, Slice | Shape | 1.0 |
| Deltoid Mesh Volume | Shape | 1.0 |
| Deltoid Sphericity | Shape | 1.0 |
| Deltoid Surface to Volume Ratio | Shape | 1.0 |
| Deltoid $10^{th}$ Percentile | First-Order | 1.0 |
| Deltoid Entropy | First-Order | 0.99 |
| Deltoid Interquartile Range | First-Order | 1.0 |
| Deltoid Kurtosis | First-Order | 0.98 |
| Deltoid Maximum | First-Order | 1.0 |
| Deltoid Mean | First-Order | 1.0 |
| Deltoid Minimum | First-Order | 0.99 |
| Deltoid Skewness | First-Order | 0.99 |
| Deltoid glcm Autocorrelation | Second-Order/Texture | 0.92 |
| Deltoid glcm Cluster Tendency | Second-Order/Texture | 0.92 |
| Deltoid glcm Contrast | Second-Order/Texture | 0.91 |
| Deltoid glcm Correlation | Second-Order/Texture | 0.99 |
| Deltoid glcm Id | Second-Order/Texture | 0.99 |
| Deltoid glcm Joint Energy | Second-Order/Texture | 0.96 |
| Deltoid glcm MCC | Second-Order/Texture | 0.98 |
| Deltoid glcm Sum Entropy | Second-Order/Texture | 0.99 |
| Deltoid gldm Dependence Entropy | Second-Order/Texture | 0.99 |
| Deltoid gldm Large Dependence High Gray Level Emphasis | Second-Order/Texture | 0.97 |
| Deltoid gldm Large Dependence Low Gray Level Emphasis | Second-Order/Texture | 0.93 |
| Deltoid gldm Low Gray Level Emphasis | Second-Order/Texture | 0.96 |

FIG. 17

| | | |
|---|---|---|
| Deltoid gldm Small Dependence Low Gray Level Emphasis | Second-Order/Texture | 0.95 |
| Deltoid glrlm Run Entropy | Second-Order/Texture | 0.97 |
| Deltoid glszm Gray Level NonUniformity Normalized | Second-Order/Texture | 0.97 |
| Deltoid glszm Gray Level Variance | Second-Order/Texture | 0.95 |
| Deltoid glszm Size Zone NonUniformity Normalized | Second-Order/Texture | 0.94 |
| Deltoid ngtdm Coarseness | Second-Order/Texture | 0.91 |
| Deltoid ngtdm Strength | Second-Order/Texture | 0.92 |

FIG. 17 (CONT'D)

| | | |
|---|---|---|
| Scapula gldm Dependence Entropy | Second-Order/Texture | 0.99 |
| Scapula gldm Dependence Variance | Second-Order/Texture | 0.96 |
| Scapula gldm Gray Level Variance | Second-Order/Texture | 0.92 |
| Scapula gldm High Gray Level Emphasis | Second-Order/Texture | 0.92 |
| Scapula gldm Large Dependence High Gray Level Emphasis | Second-Order/Texture | 0.94 |
| Scapula gldm Large Dependence Low Gray Level Emphasis | Second-Order/Texture | 0.94 |
| Scapula gldm Small Dependence Low Gray Level Emphasis | Second-Order/Texture | 0.92 |
| Scapula ngtd Strength | Second-Order/Texture | 0.93 |

FIG. 17 (CONT'D)

| Radiomic Feature | Radiomic Feature Type | ICC |
|---|---|---|
| Scapula Elongation | Shape | 1 |
| Scapula Flatness | Shape | 1 |
| Scapula Least Axis Length | Shape | 1 |
| Scapula Major Axis Length | Shape | 1 |
| Scapula Maximum 2D Diameter Column | Shape | 1 |
| Scapula Maximum 2D Diameter Row | Shape | 1 |
| Scapula Maximum 2D Diameter Slice | Shape | 1 |
| Scapula Mesh Volume | Shape | 1 |
| Scapula Minor Axis Length | Shape | 1 |
| Scapula Sphericity | Shape | 0.99 |
| Scapula Surface to Volume Ratio | Shape | 1 |
| Scapula 10th Percentile | First-Order | 1 |
| Scapula Entropy | First-Order | 1 |
| Scapula Kurtosis | First-Order | 0.99 |
| Scapula Mean | First-Order | 1 |
| Scapula Minimum | First-Order | 0.99 |
| Scapula Range | First-Order | 1 |
| Scapula Skewness | First-Order | 1 |
| Scapula Autocorrelation | Second-Order/Texture | 0.92 |
| Scapula glcm Contrast | Second-Order/Texture | 0.91 |
| Scapula glcm Correlation | Second-Order/Texture | 1 |
| Scapula glcm Id | Second-Order/Texture | 0.99 |
| Scapula glcm Joint Energy | Second-Order/Texture | 0.98 |
| Scapula glcm Joint Entropy | Second-Order/Texture | 1 |
| Scapula glcm Maximum Probability | Second-Order/Texture | 0.98 |
| Scapula glcm Sum Entropy | Second-Order/Texture | 1 |
| Scapula glszm Gray Level NonUniformity Normalized | Second-Order/Texture | 0.99 |
| Scapula glszm Low Gray Level Zone Emphasis | Second-Order/Texture | 0.95 |
| Scapula glszm Size Zone NonUniformity Normalized | Second-Order/Texture | 0.98 |
| Scapula glszm Zone Entropy | Second-Order/Texture | 0.98 |

FIG. 18

| Clinical Outcomes Prediction All (aTSA, rTSA) | Preoperative MAE of Predict+ w/o Image Data (aTSA, rTSA) | Preoperative MAE of Predict+ with Deltoid Image Data | Percent Difference in MAE (Preoperative) | 3 month MAE of Predict+ w/o Image Data (aTSA, rTSA) | 3 month MAE of Predict+ with Deltoid Image Data | Percent Difference in MAE (3 month) | 6 month MAE of Predict+ w/o Image Data (aTSA, rTSA) | 6 month MAE of Predict+ with Deltoid Image Data | Percent Difference in MAE (6 month) |
|---|---|---|---|---|---|---|---|---|---|
| Abduction | 30.5 (30.9, 30.4) | 27.2 (27.8, 26.9) | 10.8% (9.6%, 11.3%) | 24.2 (24.8, 24.0) | 23.1 (23.9, 23.8) | 4.5% (3.6%, 4.7%) | 22.6 (26.0, 21.9) | 21.9 (23.2, 21.7) | 2.9% (11.0%, 1.0%) |
| External Rotation | 17.4 (16.9, 17.5) | 16.1 (15.1, 16.4) | 7.1% (10.3%, 6.2%) | 13.3 (12.8, 13.5) | 13.2 (13.3, 13.2) | 0.7% (-4.1%, 3.1%) | 13.7 (14.3, 13.5) | 13.2 (14.2, 13.0) | 3.4% (0.8%, 3.9%) |
| Forward Elevation | 30.7 (28.8, 31.3) | 29.0 (28.1, 29.3) | 5.7% (2.4%, 6.6%) | 23.5 (22.2, 22.8) | 22.1 (23.4, 21.8) | 1.6% (-5.8%, 3.6%) | 19.8 (21.2, 19.4) | 19.0 (21.2, 18.5) | 4.1% (-0.2%, 4.7%) |
| Internal Rotation Score | 1.5 (1.5, 1.5) | 1.4 (1.3, 1.4) | 8.5% (9.7%, 5.6%) | 1.2 (1.2, 1.2) | 1.2 (1.2, 1.2) | 2.1% (0.9%, 2.5%) | 1.3 (1.3, 1.3) | 1.4 (1.5, 1.4) | -8.5% (-15.7%, -5.1%) |
| ASES | Did not model | Did not model | Did not model | 13.7 (13.2, 13.9) | 13.3 (12.8, 13.5) | 2.9% (2.6%, 3.1%) | 14.0 (13.9, 14.0) | 13.9 (13.9, 13.9) | 1.1% (0.3%, 1.2%) |
| Constant | Did not model | Did not model | Did not model | 10.8 (11.5, 10.8) | 10.0 (10.0, 10.0) | 7.8% (13.4%, 6.4%) | 9.4 (9.4, 9.4) | 8.9 (8.7, 8.9) | 5.8% (7.0%, 5.4%) |
| SAS | 9.6 (9.9, 9.5) | 8.9 (8.7, 8.9) | 7.6% (11.8%, 6.3%) | 9.3 (9.7, 9.1) | 9.0 (9.9, 8.8) | 2.6% (-2.1%, 3.7%) | 8.4 (8.5, 8.4) | 8.7 (8.9, 8.7) | -3.3% (-4.6%, -3.1%) |
| Global Shoulder Function | 1.7 (1.6, 1.7) | 1.6 (1.6, 1.7) | 5.3% (3.7%, 5.5%) | 1.9 (1.7, 1.8) | 1.8 (1.8, 1.6) | 2.3% (7.8%, 0.7%) | 1.5 (1.4, 1.6) | 1.5 (1.3, 1.6) | 1.4% (5.3%, 0.6%) |
| VAS Pain | 1.9 (1.8, 1.9) | 1.8 (1.7, 1.8) | 5.1% (6.1%, 4.9%) | 1.5 (1.4, 1.6) | 1.6 (1.5, 1.6) | -1.0% (-6.3%, 0.3%) | 1.6 (1.6, 1.6) | 1.6 (1.5, 1.6) | 1.6% (6.5%, 0.2%) |

| Clinical Outcomes Prediction All (aTSA, rTSA) | 1yr MAE of Predict+ w/o Image Data (aTSA, rTSA) | 1yr MAE of Predict+ with Deltoid Image Data | Percent Difference in MAE (1yr) | 2-3yr MAE of Predict+ w/o Image Data (aTSA, rTSA) | 2-3yr MAE of Predict+ with Deltoid Image Data | Percent Difference in MAE (2-3yr) | 3-5yr MAE of Predict+ w/o Image Data (aTSA, rTSA) | 3-5yr MAE of Predict+ with Deltoid Image Data | Percent Difference in MAE (3-5yr) |
|---|---|---|---|---|---|---|---|---|---|
| Abduction | 20.7 (21.1, 20.5) | 19.7 (18.8, 20.1) | 4.5% (10.8%, 2.4%) | 19.4 (17.7, 20.0) | 18.7 (16.7, 19.3) | 3.8% (5.5%, 3.8%) | 18.3 (15.8, 18.3) | 16.8 (15.6, 17.1) | 9.3% (1.5%, 11.4%) |
| External Rotation | 12.4 (12.6, 12.3) | 12.2 (12.5, 12.1) | 1.1% (0.0%, 1.5%) | 13.0 (12.7, 13.0) | 12.9 (12.1, 13.2) | 0.7% (5.2%, -0.9%) | 13.0 (12.8, 13.1) | 12.4 (13.7, 11.8) | 4.7% (-6.0%, 8.5%) |
| Forward Elevation | 17.2 (18.3, 16.8) | 16.3 (16.2, 16.4) | 4.9% (11.5%, 2.7%) | 15.6 (15.2, 15.8) | 15.1 (15.2, 15.0) | 3.5% (0.0%, 4.9%) | 16.7 (14.4, 17.5) | 15.5 (14.1, 16.1) | 6.9% (2.1%, 8.1%) |
| Internal Rotation Score | 1.2 (1.1, 1.3) | 1.2 (1.1, 1.3) | -0.6% (0.5%, -0.2%) | 1.2 (0.9, 1.3) | 1.2 (1.0, 1.3) | -4.9% (-8.1%, -4.0%) | 1.1 (1.0, 1.1) | 1.1 (1.1, 1.2) | -2.7% (-6.8%, -1.4%) |
| ASES | 12.1 (11.6, 12.2) | 12.1 (11.0, 12.5) | -0.6% (5.2%, -2.2%) | 12.4 (11.9, 12.6) | 12.8 (11.0, 13.5) | -3.9% (7.2%, -7.4%) | 11.1 (8.8, 11.9) | 11.4 (9.7, 12.2) | -3.2% (-9.7%, -2.5%) |
| Constant | 9.3 (9.6, 9.2) | 9.1 (9.2, 9.1) | 1.7% (3.5%, 1.2%) | 9.6 (8.7, 9.9) | 9.8 (9.3, 9.9) | -2.2% (-7.4%, -0.7%) | 9.1 (9.6, 8.9) | 8.6 (8.0, 8.9) | 5.1% (16.3%, 0.5%) |
| SAS | 8.1 (8.3, 8.0) | 7.9 (7.8, 7.9) | 3.0% (5.5%, 2.2%) | 8.1 (7.6, 8.3) | 8.0 (7.3, 8.2) | 1.3% (3.8%, 0.7%) | 7.5 (7.1, 7.7) | 7.6 (7.8, 7.6) | -1.9% (-9.8%, 0.8%) |
| Global Shoulder Function | 1.3 (1.3, 1.4) | 1.3 (1.2, 1.4) | -0.1% (2.7%, -1.0%) | 1.4 (1.2, 1.5) | 1.4 (1.2, 1.4) | 2.7% (0.2%, 3.2%) | 1.4 (1.3, 1.4) | 1.4 (1.3, 1.5) | -4.8% (-2.4%, -5.6%) |
| VAS Pain | 1.4 (1.4, 1.4) | 1.4 (1.3, 1.5) | 0.7% (8.2%, -1.8%) | 1.6 (1.5, 1.6) | 1.5 (1.3, 1.6) | 3.1% (13.4%, -0.5%) | 1.3 (1.2, 1.3) | 1.3 (1.3, 1.4) | -5.1% (-8.6%, -3.6%) |

FIG. 19

| All (aTSA, rTSA) | ML Model | Active Abduction | Active Forward Elevation | IR Score | Active External Rotation | VAS Pain | Global Shoulder Function | Constant | ASES | SAS |
|---|---|---|---|---|---|---|---|---|---|---|
| **MCID** | | 7.85 (11.3, 4.4) | 12.85 (17.2, 8.5) | 0.6 (0.6, -0.1) | 6.05 (9.5, 2.6) | -1.3 (-1.3, -1.3) | 1.1 (1.1, 1.1) | 5.8 (8.6, 3.0) | 12.7 (14.2, 11.2) | 6.65 (8.4, 4.9) |
| **Precision, %** | Non-image | 91.8% (87.2%, 92.8%) | 93.4% (90.5%, 94.4%) | 80.7% (87.4%, 90.8%) | 82.9% (90.4%, 82.5%) | 91.9% (93.6%, 91.2%) | 89.7% (90.2%, 89.6%) | 91.2% (88.6%, 92.2%) | 92.9% (94.2%, 92.8%) | 92.5% (95.1%, 91.7%) |
| | image model | 91.6% (90.7%, 91.4%) | 93.5% (91.4%, 95.0%) | 81.8% (92.0%, 88.9%) | 83.0% (89.4%, 82.4%) | 92.4% (95.8%, 91.1%) | 91.5% (90.4%, 92.0%) | 91.3% (85.7%, 92.0%) | 92.6% (95.1%, 92.3%) | 94.1% (95.8%, 94.1%) |
| **Recall, %** | Non-image | 95.3% (93.4%, 96.0%) | 94.3% (89.8%, 94.8%) | 79.8% (84.9%, 83.1%) | 90.3% (89.0%, 91.8%) | 96.1% (97.8%, 95.5%) | 96.2% (94.6%, 96.9%) | 97.4% (90.3%, 98.7%) | 98.7% (99.4%, 98.3%) | 98.4% (98.8%, 98.4%) |
| | image model | 93.8% (94.1%, 95.2%) | 93.7% (89.9%, 94.7%) | 79.3% (85.2%, 83.9%) | 91.1% (91.5%, 91.9%) | 96.3% (97.1%, 95.9%) | 96.2% (95.7%, 96.4%) | 96.4% (92.3%, 98.7%) | 97.8% (97.4%, 97.6%) | 98.4% (98.3%, 99.1%) |
| **Accuracy, %** | Non-image | 89.2% (84.2%, 90.6%) | 90.4% (85.6%, 91.3%) | 76.6% (79.9%, 80.5%) | 79.9% (83.4%, 80.0%) | 89.8% (92.2%, 89.0%) | 88.2% (87.1%, 88.6%) | 90.9% (84.5%, 92.6%) | 92.5% (94.1%, 92.1%) | 91.9% (94.2%, 91.3%) |
| | image model | 88.2% (86.0%, 88.8%) | 90.2% (87.0%, 91.6%) | 76.5% (83.0%, 79.7%) | 80.7% (84.7%, 80.1%) | 90.3% (93.6%, 89.0%) | 89.6% (87.9%, 90.3%) | 90.4% (84.1%, 92.4%) | 91.5% (93.3%, 91.1%) | 93.3% (94.6%, 93.9%) |
| **AUROC** | Non-image | 0.786 (0.732, 0.805) | 0.858 (0.818, 0.860) | 0.758 (0.757, 0.773) | 0.725 (0.743, 0.708) | 0.785 (0.752, 0.791) | 0.763 (0.734, 0.776) | 0.843 (0.801, 0.858) | 0.781 (0.785, 0.781) | 0.772 (0.748, 0.773) |
| | image model | 0.789 (0.820, 0.782) | 0.862 (0.853, 0.865) | 0.756 (0.808, 0.750) | 0.740 (0.753, 0.715) | 0.780 (0.802, 0.774) | 0.781 (0.727, 0.798) | 0.842 (0.793, 0.851) | 0.772 (0.799, 0.773) | 0.810 (0.796, 0.817) |

FIG. 20

| All (aTSA, rTSA) | ML Model | Active Abduction | Active Forward Elevation | IR Score | Active External Rotation | VAS Pain | Global Shoulder Function | Constant | ASES | SAS |
|---|---|---|---|---|---|---|---|---|---|---|
| **SCB** | | 25.6 (31.1, 20.1) | 29.85 (36.7, 23.0) | 0.35 (1.1, 0.6) | 12.55 (16.4, 8.7) | -2.9 (-3.1, -2.7) | 2.8 (3.0, 2.6) | 17.5 (20.4, 14.6) | 30.95 (33.2, 28.7) | 16.75 (19.1, 14.4) |
| **Precision, %** | Non-image | 85.3% (86.3%, 85.9%) | 91.7% (86.6%, 90.8%) | 78.3% (73.2%, 77.8%) | 79.6% (82.7%, 82.1%) | 88.8% (84.3%, 87.9%) | 89.0% (80.7%, 87.0%) | 84.9% (78.9%, 88.5%) | 85.2% (86.7%, 85.6%) | 86.3% (87.6%, 87.1%) |
| | Image model | 85.1% (78.0%, 87.7%) | 93.5% (86.0%, 92.7%) | 80.2% (81.8%, 77.5%) | 79.0% (81.3%, 82.3%) | 89.3% (83.1%, 88.6%) | 90.7% (76.5%, 90.4%) | 86.8% (76.8%, 89.6%) | 86.0% (89.3%, 85.1%) | 87.4% (86.9%, 88.9%) |
| **Recall, %** | Non-image | 93.8% (91.8%, 95.8%) | 91.9% (89.7%, 96.9%) | 87.6% (87.1%, 77.5%) | 82.4% (86.1%, 85.9%) | 88.0% (92.1%, 89.3%) | 87.4% (83.9%, 90.8%) | 89.1% (79.5%, 92.8%) | 88.1% (87.0%, 89.2%) | 92.9% (91.0%, 93.1%) |
| | Image model | 92.5% (90.5%, 95.1%) | 91.3% (87.5%, 94.9%) | 86.8% (83.5%, 76.8%) | 84.2% (84.7%, 85.8%) | 88.3% (92.5%, 90.1%) | 86.7% (85.8%, 91.2%) | 86.5% (84.6%, 90.8%) | 86.8% (91.8%, 86.6%) | 92.4% (88.6%, 93.6%) |
| **Accuracy, %** | Non-image | 85.3% (86.7%, 86.1%) | 89.0% (87.2%, 91.0%) | 78.1% (79.3%, 75.4%) | 75.7% (79.2%, 77.9%) | 82.6% (81.7%, 83.2%) | 83.3% (78.9%, 83.9%) | 83.5% (78.5%, 87.0%) | 80.6% (80.4%, 81.3%) | 84.0% (82.8%, 84.6%) |
| | Image model | 84.5% (81.2%, 87.4%) | 89.8% (87.3%, 91.1%) | 78.8% (81.9%, 74.3%) | 76.3% (77.4%, 78.2%) | 83.0% (81.4%, 84.0%) | 83.6% (77.2%, 86.4%) | 83.3% (81.0%, 86.4%) | 80.3% (85.5%, 79.2%) | 84.6% (80.6%, 86.3%) |
| **AUROC** | Non-image | 0.814 (0.860, 0.803) | 0.874 (0.871, 0.871) | 0.759 (0.799, 0.752) | 0.735 (0.764, 0.738) | 0.769 (0.734, 0.779) | 0.804 (0.778, 0.793) | 0.818 (0.788, 0.838) | 0.750 (0.744, 0.747) | 0.767 (0.719, 0.766) |
| | Image model | 0.810 (0.802, 0.829) | 0.889 (0.873, 0.881) | 0.763 (0.820, 0.739) | 0.742 (0.748, 0.745) | 0.770 (0.734, 0.782) | 0.806 (0.759, 0.817) | 0.823 (0.816, 0.837) | 0.754 (0.795, 0.729) | 0.775 (0.710, 0.787) |

FIG. 21

| Clinical Outcomes Prediction All (aTSA, rTSA) | Preoperative MAE of Predict+ w/o Image Data (aTSA, rTSA) | Preoperative MAE of Predict+ with Scapular Bone Image Data | Percent Difference in MAE (Preoperative) | 3 month MAE of Predict+ w/o Image Data (aTSA, rTSA) | 3 month MAE of Predict+ with Scapular Bone Image Data | Percent Difference in MAE (3 month) | 6 month MAE of Predict+ w/o Image Data (aTSA, rTSA) | 6 month MAE of Predict+ with Scapular Bone Image Data | Percent Difference in MAE (6 month) |
|---|---|---|---|---|---|---|---|---|---|
| Abduction | 30.5 (30.6, 30.4) | 28.4 (28.8, 28.3) | 6.9% (6.7%, 6.9%) | 24.2 (24.8, 24.0) | 22.7 (24.0, 22.2) | 6.0% (3.4%, 7.3%) | 22.6 (26.0, 21.8) | 20.4 (21.0, 20.2) | 9.7% (19.4%, 8.0%) |
| External Rotation | 17.4 (18.6, 17.5) | 16.5 (15.3, 16.8) | 5.4% (9.1%, 3.9%) | 13.3 (12.8, 13.5) | 13.5 (13.2, 13.6) | -1.3% (-3.8%, -0.6%) | 13.7 (14.3, 13.5) | 14.0 (14.7, 13.8) | -2.4% (-3.0%, -2.0%) |
| Forward Elevation | 30.7 (28.8, 31.3) | 28.1 (26.8, 28.6) | 8.6% (7.0%, 8.8%) | 22.5 (22.2, 22.6) | 21.8 (20.8, 22.1) | 3.1% (6.2%, 2.3%) | 19.8 (21.2, 19.4) | 18.6 (19.2, 18.5) | 5.9% (9.4%, 4.7%) |
| Internal Rotation Score | 1.5 (1.5, 1.5) | 1.4 (1.3, 1.4) | 6.9% (9.2%, 6.0%) | 1.2 (1.2, 1.2) | 1.2 (1.1, 1.2) | 0.0% (5.2%, -1.8%) | 1.3 (1.3, 1.3) | 1.3 (1.3, 1.3) | 0.6% (0.4%, 0.7%) |
| ASES | Did not model | Did not model | Did not model | 13.7 (13.3, 13.9) | 13.6 (13.3, 13.7) | 0.8% (-0.8%, 1.1%) | 14.0 (13.9, 14.0) | 13.3 (14.0, 13.1) | 5.3% (-0.8%, 6.5%) |
| Constant | Did not model | Did not model | Did not model | 10.8 (11.5, 10.6) | 10.0 (10.0, 10.0) | 7.5% (13.3%, 6.0%) | 9.4 (9.4, 9.4) | 9.3 (8.5, 9.5) | 1.5% (9.5%, -0.5%) |
| SAS | 9.6 (9.9, 9.5) | 9.3 (9.1, 9.4) | 3.0% (8.2%, 1.3%) | 9.3 (9.7, 9.1) | 8.9 (9.0, 8.9) | 3.5% (7.7%, 2.2%) | 8.4 (8.5, 8.4) | 8.9 (8.8, 8.9) | -5.3% (-4.2%, -5.6%) |
| Global Shoulder Function | 1.7 (1.6, 1.7) | 1.6 (1.6, 1.7) | 5.1% (2.9%, 5.2%) | 1.6 (1.7, 1.6) | 1.6 (1.7, 1.6) | -1.4% (-2.2%, -0.8%) | 1.5 (1.4, 1.6) | 1.6 (1.4, 1.6) | -0.6% (-2.1%, -1.0%) |
| VAS Pain | 1.9 (1.8, 1.9) | 1.8 (1.7, 1.8) | 3.1% (6.7%, 1.8%) | 1.5 (1.4, 1.6) | 1.6 (1.5, 1.6) | -1.9% (-5.6%, -1.4%) | 1.6 (1.6, 1.6) | 1.5 (1.5, 1.5) | 9.0% (9.6%, 8.8%) |
| Clinical Outcomes Prediction All (aTSA, rTSA) | 1yr MAE of Predict+ w/o Image Data (aTSA, rTSA) | 1yr MAE of Predict+ with Scapular Bone Image Data | Percent Difference in MAE (1yr) | 2-3yr MAE of Predict+ w/o Image Data (aTSA, rTSA) | 2-3yr MAE of Predict+ with Scapular Bone Image Data | Percent Difference in MAE (2-3yr) | 3-5yr MAE of Predict+ w/o Image Data (aTSA, rTSA) | 3-5yr MAE of Predict+ with Scapular Bone Image Data | Percent Difference in MAE (3-5yr) |
| Abduction | 20.7 (21.1, 20.5) | 18.6 (17.8, 18.8) | 10.2% (15.0%, 8.5%) | 19.4 (17.7, 20.0) | 18.3 (17.7, 18.6) | 5.6% (-0.1%, 7.2%) | 18.3 (15.8, 19.3) | 18.0 (17.1, 18.3) | 2.1% (-8.2%, 5.2%) |
| External Rotation | 12.4 (13.5, 12.3) | 12.6 (12.8, 12.4) | -1.6% (-3.2%, -0.9%) | 13.0 (12.7, 13.0) | 12.4 (12.5, 12.4) | 4.1% (1.7%, 4.9%) | 13.0 (12.8, 13.1) | 12.6 (13.7, 13.1) | 3.9% (-6.9%, 7.1%) |
| Forward Elevation | 17.2 (18.3, 16.8) | 15.6 (14.7, 15.9) | 9.4% (20.0%, 5.6%) | 15.6 (15.2, 15.8) | 16.0 (15.2, 16.3) | -2.4% (0.2%, -3.3%) | 16.7 (14.4, 17.5) | 14.8 (13.4, 15.5) | 11.1% (7.1%, 11.7%) |
| Internal Rotation Score | 1.2 (1.1, 1.3) | 1.2 (1.1, 1.3) | -0.1% (-0.5%, 0.0%) | 1.2 (0.9, 1.3) | 1.2 (1.0, 1.2) | 0.8% (-8.0%, 2.2%) | 1.1 (1.0, 1.1) | 1.1 (1.1, 1.1) | 1.9% (-8.8%, 5.4%) |
| ASES | 12.1 (11.6, 12.2) | 11.7 (11.3, 11.8) | 3.2% (3.0%, 3.3%) | 12.4 (11.9, 12.6) | 12.4 (11.5, 12.8) | -0.2% (3.4%, -1.8%) | 11.1 (8.9, 11.9) | 11.2 (10.5, 11.4) | -0.7% (-18.1%, 3.4%) |
| Constant | 9.3 (9.6, 9.2) | 9.0 (8.0, 9.3) | 3.5% (16.2%, -0.5%) | 9.5 (8.7, 9.8) | 9.6 (9.5, 9.6) | -0.4% (-8.9%, 2.0%) | 9.1 (9.6, 8.9) | 7.9 (8.0, 7.8) | 13.7% (16.0%, 12.5%) |
| SAS | 8.1 (8.3, 8.0) | 7.6 (6.8, 8.0) | 5.8% (18.3%, 1.1%) | 8.1 (7.6, 8.3) | 7.6 (7.3, 7.7) | 6.4% (3.8%, 7.2%) | 7.5 (7.1, 7.7) | 7.1 (6.8, 7.2) | 5.6% (3.0%, 6.1%) |
| Global Shoulder Function | 1.3 (1.3, 1.4) | 1.3 (1.1, 1.4) | 2.3% (12.5%, -0.9%) | 1.4 (1.2, 1.5) | 1.4 (1.2, 1.5) | -0.2% (-0.7%, -0.3%) | 1.4 (1.3, 1.4) | 1.4 (1.3, 1.4) | 0.1% (0.0%, 0.1%) |
| VAS Pain | 1.4 (1.4, 1.4) | 1.3 (1.2, 1.4) | 6.5% (14.1%, 4.0%) | 1.6 (1.5, 1.6) | 1.4 (1.4, 1.5) | 7.9% (6.1%, 7.7%) | 1.3 (1.2, 1.3) | 1.3 (1.2, 1.3) | -2.3% (-4.9%, -1.7%) |

FIG. 22

| All (aTSA, rTSA) | ML Model | Active Abduction | Active Forward Elevation | IR Score | Active External Rotation | VAS Pain | Global Shoulder Function | Constant | ASES | SAS |
|---|---|---|---|---|---|---|---|---|---|---|
| MCID | | 7.85 (11.3, 4.4) | 12.85 (17.2, 8.5) | 0.6 (0.6, -0.1) | 6.05 (9.5, 2.6) | -1.3 (-1.3, -1.3) | 1.1 (1.1, 1.1) | 5.8 (8.6, 3.0) | 12.7 (14.2, 11.2) | 6.65 (8.4, 4.9) |
| Precision, % | Non-image | 91.8% (87.2%, 92.8%) | 93.4% (90.5%, 94.4%) | 80.7% (87.4%, 90.8%) | 82.9% (90.4%, 82.5%) | 91.9% (93.6%, 91.2%) | 89.7% (90.2%, 89.6%) | 91.2% (88.6%, 93.2%) | 92.9% (94.2%, 92.8%) | 92.5% (95.1%, 91.7%) |
| | Scapular Bone Image model | 90.6% (89.1%, 92.5%) | 92.4% (87.7%, 94.1%) | 79.2% (86.9%, 87.7%) | 83.4% (91.2%, 83.4%) | 91.5% (90.8%, 91.8%) | 90.8% (92.0%, 90.3%) | 92.6% (88.6%, 92.5%) | 92.6% (93.6%, 92.3%) | 93.7% (95.8%, 93.6%) |
| Recall, % | Non-image | 95.3% (93.4%, 96.0%) | 94.3% (89.8%, 94.8%) | 79.6% (64.9%, 83.1%) | 90.3% (89.0%, 91.8%) | 96.1% (97.8%, 95.5%) | 96.2% (94.6%, 96.9%) | 97.4% (90.3%, 98.7%) | 98.7% (99.4%, 98.3%) | 98.4% (98.8%, 98.4%) |
| | Scapular Bone Image model | 93.9% (95.5%, 95.0%) | 93.2% (87.5%, 93.0%) | 76.6% (82.2%, 81.3%) | 91.1% (91.8%, 93.2%) | 96.2% (96.2%, 96.2%) | 95.5% (94.1%, 96.1%) | 96.2% (91.1%, 97.8%) | 97.2% (97.6%, 97.3%) | 97.6% (97.1%, 98.4%) |
| Accuracy, % | Non-image | 89.2% (84.2%, 90.6%) | 90.4% (85.6%, 91.3%) | 76.6% (79.9%, 80.5%) | 79.9% (83.4%, 80.0%) | 89.6% (92.2%, 89.0%) | 88.2% (87.1%, 88.6%) | 90.9% (84.5%, 92.6%) | 92.5% (94.1%, 92.1%) | 91.9% (94.2%, 91.3%) |
| | Scapular Bone Image model | 87.3% (87.7%, 89.6%) | 89.0% (82.3%, 89.6%) | 74.6% (78.3%, 77.6%) | 80.9% (86.0%, 81.7%) | 89.7% (89.1%, 90.0%) | 88.8% (88.9%, 88.8%) | 91.5% (86.1%, 92.4%) | 91.0% (92.2%, 90.8%) | 92.5% (93.9%, 93.0%) |
| AUROC | Non-image | 0.786 (0.732, 0.805) | 0.858 (0.818, 0.860) | 0.758 (0.757, 0.773) | 0.725 (0.743, 0.708) | 0.785 (0.752, 0.791) | 0.763 (0.734, 0.776) | 0.843 (0.801, 0.858) | 0.781 (0.785, 0.781) | 0.772 (0.748, 0.773) |
| | Scapular Bone Image model | 0.773 (0.800, 0.803) | 0.843 (0.788, 0.841) | 0.742 (0.759, 0.740) | 0.738 (0.755, 0.724) | 0.790 (0.785, 0.795) | 0.800 (0.818, 0.792) | 0.875 (0.835, 0.870) | 0.760 (0.782, 0.752) | 0.813 (0.852, 0.811) |

FIG. 23

| All (aTSA, rTSA) | ML Model | Active Abduction | Active Forward Elevation | IR Score | Active External Rotation | VAS Pain | Global Shoulder Function | Constant | ASES | SAS |
|---|---|---|---|---|---|---|---|---|---|---|
| **SCB** | | 25.6 (31.1, 20.1) | 29.85 (36.7, 23.0) | 0.25 (1.1, 0.6) | 12.55 (16.4, 8.7) | -2.9 (-3.1, -2.7) | 2.8 (3.0, 2.6) | 17.5 (20.4, 14.6) | 30.95 (33.2, 28.7) | 16.75 (19.1, 14.4) |
| **Precision, %** | Non-image | 85.3% (86.3%, 85.9%) | 91.7% (86.6%, 90.8%) | 78.3% (73.2%, 77.8%) | 79.6% (82.7%, 82.1%) | 88.8% (84.3%, 87.9%) | 89.0% (80.7%, 87.0%) | 84.9% (78.9%, 88.5%) | 85.2% (86.7%, 85.6%) | 86.3% (87.6%, 87.1%) |
| | Scapular Bone Image model | 85.1% (80.3%, 85.3%) | 91.3% (86.8%, 91.4%) | 76.9% (74.6%, 75.9%) | 79.1% (83.9%, 82.4%) | 90.0% (85.4%, 89.8%) | 90.0% (80.3%, 88.5%) | 83.6% (76.2%, 86.9%) | 84.9% (83.6%, 85.6%) | 87.4% (87.5%, 88.7%) |
| **Recall, %** | Non-image | 93.8% (91.5%, 95.8%) | 91.9% (89.7%, 96.5%) | 87.6% (97.1%, 77.8%) | 82.4% (86.1%, 85.9%) | 88.0% (92.1%, 89.3%) | 87.4% (83.9%, 90.8%) | 89.1% (79.5%, 92.8%) | 88.1% (87.0%, 89.2%) | 92.9% (91.0%, 93.1%) |
| | Scapular Bone Image model | 93.1% (91.4%, 95.0%) | 88.7% (84.0%, 92.8%) | 84.3% (84.1%, 73.7%) | 85.4% (86.9%, 86.5%) | 88.9% (93.9%, 90.4%) | 88.4% (92.7%, 90.5%) | 88.5% (77.4%, 93.8%) | 88.3% (90.0%, 88.2%) | 91.6% (88.6%, 92.9%) |
| **Accuracy, %** | Non-image | 85.3% (86.7%, 86.1%) | 89.0% (87.2%, 91.0%) | 78.1% (79.3%, 75.4%) | 75.7% (79.2%, 77.9%) | 82.6% (81.7%, 83.2%) | 83.3% (78.9%, 83.9%) | 83.5% (78.5%, 87.0%) | 80.6% (80.4%, 81.3%) | 84.0% (82.8%, 84.6%) |
| | Scapular Bone Image model | 85.3% (82.7%, 85.9%) | 87.3% (86.1%, 89.1%) | 76.1% (79.7%, 73.2%) | 77.2% (79.8%, 78.7%) | 84.3% (85.4%, 85.1%) | 85.0% (83.3%, 85.0%) | 83.3% (78.4%, 86.9%) | 81.0% (81.5%, 80.6%) | 84.6% (82.1%, 86.0%) |
| **AUROC** | Non-image | 0.814 (0.860, 0.803) | 0.874 (0.871, 0.871) | 0.759 (0.799, 0.752) | 0.735 (0.764, 0.738) | 0.769 (0.734, 0.779) | 0.804 (0.778, 0.793) | 0.818 (0.788, 0.838) | 0.750 (0.744, 0.747) | 0.767 (0.719, 0.766) |
| | Scapular Bone Image model | 0.823 (0.815, 0.816) | 0.868 (0.861, 0.870) | 0.745 (0.801, 0.732) | 0.749 (0.758, 0.750) | 0.798 (0.818, 0.799) | 0.827 (0.824, 0.812) | 0.822 (0.784, 0.841) | 0.763 (0.776, 0.746) | 0.794 (0.759, 0.797) |

FIG. 24

| Feature | F-Score Ranking of Preoperative Inputs, Preop | Average F - Score | Abduction | External Rotation | Forward Elevation | Internal Rotation Score | SAS | Global Shoulder Function | VAS Pain |
|---|---|---|---|---|---|---|---|---|---|
| Glenoid Retroversion | 1 (Most Used Feature) | 6407 | 5018 | 10537 | 5702 | 5769 | 7545 | 5024 | 5257 |
| Glenoid Bone Width | 2 | 4755 | 3305 | 7732 | 4143 | 4391 | 6145 | 3844 | 3722 |
| Beta Angle | 3 | 4605 | 3822 | 7329 | 3820 | 3950 | 6079 | 3831 | 3407 |
| Age | 4 | 4428 | 4235 | 8782 | 4501 | 2774 | 5068 | 3079 | 2556 |
| Glenoid Bone Height | 5 | 4254 | 3261 | 7290 | 3705 | 4243 | 4903 | 3121 | 3256 |
| Humeral Head Subluxation | 6 | 3845 | 3047 | 5807 | 3458 | 3497 | 5004 | 3086 | 3018 |
| Deltoid Volume Normalized by Age and Gender | 7 | 3788 | 3089 | 5843 | 3831 | 3399 | 4615 | 3011 | 2726 |
| Deltoid Fat Percentage | 8 | 3556 | 2985 | 5639 | 3080 | 3424 | 4444 | 2942 | 2375 |
| Deltoid Elongation | 9 | 3401 | 3010 | 4907 | 3292 | 2960 | 4114 | 2809 | 2712 |
| Deltoid Flatness | 10 | 3261 | 2754 | 4888 | 2932 | 2940 | 4244 | 2397 | 2809 |
| Deltoid Max 2D Diameter, Row | 11 | 2766 | 2149 | 4549 | 2447 | 2646 | 3161 | 2389 | 2020 |
| Deltoid Max 2D Diameter, Column | 12 | 2668 | 2297 | 4064 | 2513 | 2405 | 3142 | 2288 | 1967 |
| Deltoid Sphericity | 13 | 2588 | 1998 | 4114 | 2542 | 2405 | 3002 | 2118 | 1936 |
| Deltoid Least Axis Length | 14 | 2545 | 1914 | 3921 | 2215 | 2225 | 3240 | 2193 | 2106 |
| Deltoid Major Axis Length | 15 | 2395 | 2031 | 3768 | 2284 | 2104 | 2939 | 1960 | 1676 |
| Deltoid 10th Percentile, 1st Order | 16 | 2344 | 1996 | 3710 | 2043 | 2210 | 2785 | 1899 | 1767 |
| Deltoid Max 2D Diameter, Slice | 17 | 2272 | 2084 | 3418 | 2251 | 2078 | 2727 | 1727 | 1618 |
| Pixel Spacing | 18 | 2241 | 1988 | 3403 | 2185 | 1888 | 2639 | 1868 | 1713 |
| Bmi | 19 | 2200 | 1870 | 4016 | 2034 | 1457 | 2643 | 1704 | 1674 |
| Deltoid Max, 1st Order | 20 | 2165 | 2069 | 3000 | 2267 | 1873 | 2783 | 1640 | 1525 |

FIG. 25

| Feature | F-Score Ranking of Preoperative Inputs, 2-3 year | Average F - Score | Abduction | External Rotation | Forward Elevation | Internal Rotation Score | ASES | Constant | SAS | Global Shoulder Function | VAS Pain |
|---|---|---|---|---|---|---|---|---|---|---|---|
| Abduction | 1 (Most Used Feature) | 2437 | 3205 | 4648 | 2956 | 1902 | 1147 | 844 | 3163 | 2111 | 1958 |
| Glenoid Retroversion | 2 | 1833 | 2230 | 3002 | 2305 | 1694 | 1032 | 778 | 2338 | 1681 | 1434 |
| External Rotation | 3 | 1776 | 2235 | 3511 | 1660 | 1476 | 795 | 719 | 2286 | 1831 | 1474 |
| Forward Elevation | 4 | 1776 | 1949 | 3932 | 2174 | 1518 | 845 | 582 | 2038 | 1588 | 1355 |
| SAS score | 5 | 1638 | 1852 | 2726 | 1729 | 1745 | 693 | 680 | 2274 | 1793 | 1290 |
| Age | 6 | 1631 | 2392 | 3754 | 2297 | 1176 | 531 | 343 | 1643 | 1284 | 1260 |
| Composite ROM score | 7 | 1605 | 1837 | 2627 | 1704 | 1723 | 792 | 609 | 2525 | 1358 | 1269 |
| Glenoid Bone Height | 8 | 1455 | 1754 | 2291 | 1759 | 1230 | 744 | 679 | 1964 | 1523 | 1151 |
| Glenoid Bone Width | 9 | 1447 | 1430 | 2617 | 1835 | 1641 | 729 | 653 | 1683 | 1197 | 1237 |
| Deltoid Volume Normalized by Age and Gender | 10 | 1416 | 1863 | 1815 | 1398 | 1097 | 722 | 817 | 2010 | 1621 | 1403 |
| VAS Pain | 11 | 1293 | 1605 | 2314 | 1372 | 1096 | 533 | 507 | 1795 | 1152 | 1259 |
| Deltoid Flatness | 12 | 1277 | 1595 | 2235 | 1685 | 1172 | 616 | 557 | 1626 | 984 | 1020 |
| Global Shoulder Function score | 13 | 1227 | 1380 | 2253 | 1350 | 991 | 602 | 442 | 1780 | 1308 | 934 |
| Deltoid Elongation | 14 | 1216 | 1573 | 2336 | 1237 | 1215 | 560 | 496 | 1668 | 963 | 894 |
| IR Score | 15 | 1118 | 1551 | 2069 | 1269 | 1109 | 488 | 382 | 1325 | 906 | 965 |
| Beta Angle | 16 | 1111 | 1341 | 1782 | 1201 | 1075 | 603 | 593 | 1601 | 839 | 967 |
| Deltoid Sphericity | 17 | 1049 | 1271 | 1871 | 1264 | 768 | 673 | 525 | 1226 | 1153 | 693 |
| Humeral Head Subluxation | 18 | 1049 | 1457 | 1888 | 1255 | 961 | 513 | 511 | 1377 | 794 | 687 |
| Deltoid Max 2D Diameter, Column | 19 | 1025 | 1300 | 1558 | 1053 | 1092 | 671 | 606 | 1363 | 831 | 752 |
| Deltoid Max 2D Diameter, Row | 20 | 1024 | 1083 | 1951 | 1017 | 898 | 535 | 467 | 1196 | 1168 | 898 |

FIG. 26

| aTSA, rTSA | Age at time of surgery | <60 yrs | 60-70 yrs | 70-80 yrs |
|---|---|---|---|---|
| Deltoid Normalized Volume | Male | 1.05 ± 0.21, 0.95 ± 0.20 | 1.03 ± 0.19, 0.99 ± 0.19 | 1.01 ± 0.18, 1.00 ± 0.18 |
| | Female | 1.01 ± 0.17, 1.01 ± 0.18 | 1.00 ± 0.18, 1.00 ± 0.20 | 1.00 ± 0.17, 1.00 ± 0.19 |
| | P Value (aTSA, rTSA) | 0.2653, 0.1140 | 0.1166, 0.7608 | 0.5870, 0.7628 |
| Deltoid Elongation | Male | 0.854 ± 0.061, 0.852 ± 0.059 | 0.855 ± 0.065, 0.845 ± 0.065 | 0.839 ± 0.058, 0.837 ± 0.062 |
| | Female | 0.771 ± 0.060, 0.771 ± 0.066 | 0.768 ± 0.050, 0.776 ± 0.064 | 0.766 ± 0.061, 0.772 ± 0.064 |
| | P Value (aTSA, rTSA) | **<0.001, <0.001** | **<0.001, <0.001** | **<0.001, <0.001** |
| Deltoid Flatness | Male | 0.474 ± 0.035, 0.479 ± 0.041 | 0.472 ± 0.036, 0.483 ± 0.042 | 0.473 ± 0.034, 0.486 ± 0.038 |
| | Female | 0.455 ± 0.034, 0.451 ± 0.038 | 0.451 ± 0.036, 0.455 ± 0.044 | 0.454 ± 0.042, 0.457 ± 0.045 |
| | P Value (aTSA, rTSA) | **0.003, <0.001** | **<0.001, <0.001** | **0.002, <0.001** |
| Deltoid Fat Percentage (%) | Male | 12.6 ± 10.6, 15.7 ± 10.6 | 11.6 ± 10.4, 14.1 ± 11.3 | 11.2 ± 10.4, 13.4 ± 11.4 |
| | Female | 16.5 ± 10.4, 17.2 ± 10.7 | 14.6 ± 10.7, 17.2 ± 11.7 | 12.3 ± 9.1, 15.5 ± 11.7 |
| | P Value (aTSA, rTSA) | **0.048**, 0.432 | **0.013, 0.001** | 0.429, **0.005** |
| Deltoid Max 2D Diameter, Row (mm) | Male | 150.5 ± 13.1, 147.2 ± 14.9 | 150.3 ± 16.0, 149.2 ± 15.8 | 147.0 ± 16.8, 148.4 ± 17.1 |
| | Female | 121.7 ± 14.0, 124.1 ± 14.5 | 121.2 ± 15.3, 124.1 ± 16.1 | 122.8 ± 18.1, 123.3 ± 16.1 |
| | P Value (aTSA, rTSA) | **<0.001, <0.001** | **<0.001, <0.001** | **<0.001, <0.001** |
| Deltoid Sphericity | Male | 0.476 ± 0.026, 0.467 ± 0.025 | 0.462 ± 0.027, 0.465 ± 0.028 | 0.451 ± 0.024, 0.451 ± 0.024 |
| | Female | 0.469 ± 0.028, 0.468 ± 0.024 | 0.453 ± 0.029, 0.464 ± 0.030 | 0.443 ± 0.027, 0.452 ± 0.027 |
| | P Value (aTSA, rTSA) | 0.174, 0.797 | **0.012**, 0.483 | **0.027**, 0.270 |
| Deltoid Max 2D Diameter, Column (mm) | Male | 175.3 ± 12.9, 172.3 ± 12.9 | 176.7 ± 12.4, 173.1 ± 13.1 | 174.5 ± 14.3, 173.1 ± 17.1 |
| | Female | 152.9 ± 11.8, 154.7 ± 12.1 | 157.0 ± 13.3, 153.1 ± 12.5 | 154.1 ± 11.5, 151.2 ± 11.5 |
| | P Value (aTSA, rTSA) | **<0.001, <0.001** | **<0.001, <0.001** | **<0.001, <0.001** |
| Deltoid 10th Percentile, 1st Order | Male | 0.798 ± 0.148, 0.777 ± 0.154 | 0.791 ± 0.165, 0.817 ± 0.142 | 0.813 ± 0.148, 0.817 ± 0.161 |
| | Female | 0.787 ± 0.128, 0.813 ± 0.141 | 0.804 ± 0.154, 0.827 ± 0.162 | 0.841 ± 0.152, 0.827 ± 0.164 |
| | P Value (aTSA, rTSA) | 0.662, 0.185 | 0.467, 0.424 | 0.226, 0.330 |

FIG. 27

| Feature | F-Score Ranking of Preoperative Inputs, Preop | Average F - Score | Abduction | External Rotation | Forward Elevation | Internal Rotation Score | SAS | Global Shoulder Function | VAS Pain |
|---|---|---|---|---|---|---|---|---|---|
| Glenoid Retroversion | 1 (Most Used Feature) | 7168 | 5902 | 11289 | 5923 | 7099 | 8896 | 5309 | 5761 |
| Glenoid Bone Width | 2 | 5064 | 3853 | 8219 | 4238 | 5432 | 6132 | 3817 | 3758 |
| Age | 3 | 4883 | 4438 | 9724 | 4195 | 3401 | 5977 | 3300 | 3144 |
| Glenoid Bone Height | 4 | 4836 | 3733 | 7281 | 4329 | 5419 | 6072 | 3465 | 3553 |
| Beta Angle | 5 | 4252 | 3564 | 6842 | 3436 | 4506 | 4933 | 3126 | 3360 |
| Scapula Elongation | 6 | 4146 | 3356 | 6524 | 3690 | 4097 | 5016 | 3043 | 3296 |
| Scapula Flatness | 7 | 3690 | 3283 | 5796 | 3347 | 3689 | 4276 | 2908 | 2532 |
| Humeral Head Subluxation | 8 | 3665 | 3099 | 5869 | 3089 | 3744 | 4510 | 2610 | 2736 |
| Scapula Max 2D Diameter, Column | 9 | 3389 | 2928 | 4899 | 2883 | 3587 | 4317 | 2474 | 2636 |
| Scapula Max 2D Diameter, Row | 10 | 3104 | 2825 | 4399 | 2790 | 3309 | 3712 | 2114 | 2577 |
| Scapula Max 2D Diameter, Slice | 11 | 3080 | 2726 | 4902 | 2719 | 3127 | 3349 | 2051 | 2688 |
| Scapula Least Axis Length | 12 | 3008 | 2510 | 4827 | 2716 | 2956 | 3588 | 2273 | 2186 |
| Scapula Sphericity | 13 | 2839 | 2507 | 4953 | 2291 | 2675 | 3239 | 1965 | 2243 |
| Scapula Major Axis Length | 14 | 2823 | 2660 | 4312 | 2559 | 2788 | 3217 | 1909 | 2314 |
| Scapula 10th Percentile, 1st Order | 15 | 2750 | 2149 | 4642 | 2371 | 2736 | 3219 | 2012 | 2119 |
| Bmi | 16 | 2490 | 2085 | 4729 | 2054 | 1954 | 2940 | 1753 | 1918 |
| Scapula Range, 1st Order | 17 | 2397 | 2050 | 3368 | 2193 | 2677 | 2945 | 1800 | 1749 |
| Scapula Mean, 1st Order | 18 | 2313 | 1943 | 3706 | 2090 | 2389 | 2650 | 1843 | 1571 |
| Pixel Spacing | 19 | 2305 | 2036 | 3950 | 2014 | 2220 | 2527 | 1599 | 1786 |
| Scapula Kurtosis, 1st Order | 20 | 2299 | 1706 | 3575 | 1942 | 2378 | 2942 | 1692 | 1859 |

FIG. 28

| Feature | F-Score Ranking of Preoperative Inputs, 2-3 year | Average F-Score | Abduction | External Rotation | Forward Elevation | Internal Rotation Score | ASES | Constant | SAS | Global Shoulder Function | VAS Pain |
|---|---|---|---|---|---|---|---|---|---|---|---|
| Abduction | 1 (Most Used Feature) | 3106 | 3699 | 6434 | 3314 | 2894 | 1222 | 1179 | 4304 | 2752 | 2153 |
| Glenoid Retroversion | 2 | 2482 | 2748 | 4804 | 2448 | 2540 | 1328 | 1120 | 3118 | 2033 | 2202 |
| External Rotation | 3 | 2205 | 2424 | 5223 | 2108 | 1933 | 880 | 864 | 3024 | 1941 | 1449 |
| Forward Elevation | 4 | 2165 | 2269 | 4361 | 2271 | 2358 | 952 | 842 | 2788 | 1940 | 1700 |
| Age | 5 | 2104 | 2761 | 5306 | 2582 | 1712 | 604 | 446 | 2391 | 1610 | 1528 |
| Composite ROM score | 6 | 2030 | 2035 | 3653 | 1926 | 2669 | 797 | 712 | 2934 | 2104 | 1444 |
| Sas score | 7 | 1939 | 2097 | 3874 | 1652 | 1871 | 768 | 963 | 2806 | 1706 | 1443 |
| Glenoid Bone Width | 8 | 1834 | 1864 | 3473 | 2139 | 2137 | 755 | 813 | 2335 | 1644 | 1342 |
| Glenoid Bone Height | 9 | 1806 | 2006 | 3242 | 2143 | 1777 | 890 | 729 | 2270 | 1741 | 1454 |
| Scapula Flatness | 10 | 1629 | 2253 | 3271 | 1312 | 1693 | 659 | 770 | 1878 | 1400 | 1427 |
| Scapula Elongation | 11 | 1567 | 1746 | 3252 | 1739 | 1659 | 710 | 688 | 1869 | 1303 | 1134 |
| VAS pain | 12 | 1548 | 1429 | 3255 | 1653 | 1516 | 548 | 590 | 2074 | 1455 | 1410 |
| Global Shoulder Function score | 13 | 1467 | 1656 | 2729 | 1484 | 1421 | 683 | 632 | 1802 | 1472 | 1336 |
| Scapula Sphericity | 14 | 1437 | 1682 | 2711 | 1640 | 1628 | 625 | 670 | 1750 | 1170 | 1010 |
| Scapula Max 2D Diameter, Column | 15 | 1427 | 1473 | 2858 | 1368 | 1715 | 656 | 799 | 2014 | 1082 | 878 |
| Beta Angle | 16 | 1367 | 1659 | 3658 | 1372 | 1320 | 585 | 749 | 1714 | 1065 | 1178 |
| IR score | 17 | 1292 | 1463 | 2599 | 1435 | 1356 | 499 | 408 | 1707 | 1122 | 1038 |
| Scapula Max 2D Diameter, Slice | 18 | 1285 | 1403 | 2768 | 1133 | 1428 | 558 | 601 | 1464 | 1139 | 1067 |
| Scapula Least Axis Length | 19 | 1267 | 1430 | 2598 | 1405 | 1225 | 551 | 681 | 1416 | 1044 | 715 |
| Scapula 10th Percentile, 1st Order | 20 | 1248 | 1503 | 2332 | 1386 | 1228 | 680 | 666 | 1397 | 1068 | 970 |

FIG. 29

| aTSA, rTSA | Age at time of surgery (yrs) | <60 | 60-70 | 70-80 |
|---|---|---|---|---|
| **Scapula Elongation** | Male | 0.513 ± 0.032, 0.510 ± 0.038 | 0.507 ± 0.034, 0.504 ± 0.035 | 0.501 ± 0.030, 0.501 ± 0.034 |
| | Female | 0.514 ± 0.033, 0.517 ± 0.031 | 0.520 ± 0.037, 0.514 ± 0.033 | 0.515 ± 0.031, 0.516 ± 0.035 |
| | P Value (aTSA, rTSA) | 0.826, 0.187 | **<0.001, <0.001** | **<0.001, <0.001** |
| **Scapula Flatness** | Male | 0.293 ± 0.026, 0.299 ± 0.040 | 0.295 ± 0.026, 0.301 ± 0.031 | 0.298 ± 0.025, 0.299 ± 0.026 |
| | Female | 0.283 ± 0.026, 0.292 ± 0.026 | 0.295 ± 0.036, 0.293 ± 0.026 | 0.291 ± 0.022, 0.297 ± 0.027 |
| | P Value (aTSA, rTSA) | **0.011**, 0.232 | 0.968, **<0.001** | **0.034**, 0.108 |
| **Scapula Max 2D Diameter, Column (mm)** | Male | 122.2 ± 11.7, 125.6 ± 11.3 | 121.8 ± 10.4, 125.2 ± 12.6 | 121.2 ± 8.9, 125.0 ± 13.1 |
| | Female | 105.0 ± 11.9, 108.6 ± 11.2 | 104.3 ± 8.7, 105.7 ± 11.2 | 101.8 ± 9.0, 104.7 ± 9.9 |
| | P Value (aTSA, rTSA) | **<0.001, <0.001** | **<0.001, <0.001** | **<0.001, <0.001** |
| **Scapula Sphericity** | Male | 0.236 ± 0.014, 0.236 ± 0.016 | 0.237 ± 0.013, 0.235 ± 0.014 | 0.236 ± 0.013, 0.233 ± 0.013 |
| | Female | 0.238 ± 0.013, 0.234 ± 0.015 | 0.235 ± 0.016, 0.230 ± 0.014 | 0.234 ± 0.014, 0.230 ± 0.014 |
| | P Value (aTSA, rTSA) | 0.524, 0.430 | 0.173, **<0.001** | 0.264, **<0.001** |
| **Scapula, 10th Percentile, 1st Order** | Male | 1.002 ± 0.185, 0.955 ± 0.184 | 0.968 ± 0.184, 0.966 ± 0.170 | 0.981 ± 0.184, 0.956 ± 0.164 |
| | Female | 1.043 ± 0.168, 1.029 ± 0.229 | 0.989 ± 0.179, 1.002 ± 0.178 | 1.001 ± 0.189, 0.987 ± 0.184 |
| | P Value (aTSA, rTSA) | 0.126, **0.032** | 0.249, **0.006** | 0.420, **0.002** |
| **Scapula Max 2D Diameter, Row (mm)** | Male | 163.2 ± 10.1, 164.5 ± 18.1 | 164.2 ± 11.2, 165.1 ± 14.5 | 162.6 ± 10.8, 165.6 ± 13.2 |
| | Female | 140.9 ± 14.7, 145.8 ± 10.2 | 139.5 ± 9.6, 144.8 ± 12.3 | 141.9 ± 10.0, 142.5 ± 11.5 |
| | P Value (aTSA, rTSA) | **<0.001, <0.001** | **<0.001, <0.001** | **<0.001, <0.001** |
| **Scapula Least Axis Length (mm)** | Male | 57.4 ± 4.8, 57.8 ± 5.2 | 58.1 ± 4.3, 59.0 ± 4.5 | 58.5 ± 4.0, 58.9 ± 4.2 |
| | Female | 47.8 ± 3.7, 50.1 ± 4.3 | 49.4 ± 3.8, 50.1 ± 3.9 | 49.2 ± 3.7, 49.9 ± 3.5 |
| | P Value (aTSA, rTSA) | **<0.001, <0.001** | **<0.001, <0.001** | **<0.001, <0.001** |
| **Scapula Max 2D Diameter, Slice (mm)** | Male | 142.7 ± 11.5, 148.3 ± 14.9 | 144.0 ± 11.2, 145.5 ± 12.0 | 142.2 ± 9.7, 141.7 ± 10.5 |
| | Female | 121.6 ± 10.1, 125.1 ± 11.3 | 125.6 ± 9.8, 121.8 ± 11.1 | 124.4 ± 9.3, 118.4 ± 9.6 |
| | P Value (aTSA, rTSA) | **<0.001, <0.001** | **<0.001, <0.001** | **<0.001, <0.001** |

FIG. 30

| Preoperative Overhead Motion | Deltoid Normalized Volume | Deltoid Elongation | Deltoid Flatness | Deltoid Least Axis Length | Deltoid Major Axis Length | Deltoid Max 2D Diameter, Column | Deltoid Max 2D Diameter, Row | Deltoid Mesh Volume ($cm^3$) | Deltoid Sphericity | Deltoid Surface to Volume Ratio | Deltoid Fat Percentage | Deltoid 10th Percentile HU, 1st Order |
|---|---|---|---|---|---|---|---|---|---|---|---|---|
| aTSA, <160° | 1.01 ± 0.18 | 0.805 ± 0.071 | 0.461 ± 0.038 | 69.4 ± 8.3 | 150.7 ± 12.9 | 165.3 ± 16.4 | 135.0 ± 21.3 | 359.9 ± 121.8 | 0.457 ± 0.029 | 0.154 ± 0.023 | 13.3 ± 10.5% | 0.807 ± 0.154 |
| aTSA, ≥160° | 1.06 ± 0.19 | 0.831 ± 0.076 | 0.473 ± 0.033 | 72.3 ± 7.9 | 152.8 ± 12.5 | 168.0 ± 15.9 | 138.5 ± 19.4 | 400.8 ± 136.4 | 0.460 ± 0.027 | 0.147 ± 0.022 | 12.5 ± 9.3% | 0.786 ± 0.146 |
| P Value | **0.047** | **0.013** | **0.017** | **0.014** | 0.261 | 0.246 | 0.238 | **0.023** | 0.455 | **0.049** | 0.638 | 0.357 |
| rTSA, <160° | 1.00 ± 0.19 | 0.798 ± 0.072 | 0.469 ± 0.045 | 68.2 ± 8.6 | 145.6 ± 12.8 | 160.1 ± 16.3 | 133.6 ± 20.5 | 319.7 ± 107.3 | 0.453 ± 0.029 | 0.161 ± 0.023 | 15.3 ± 11.6% | 0.825 ± 0.156 |
| rTSA, ≥160° | 1.05 ± 0.16 | 0.823 ± 0.066 | 0.474 ± 0.042 | 69.4 ± 8.3 | 146.4 ± 11.4 | 161.2 ± 14.9 | 136.4 ± 18.1 | 352.2 ± 103.3 | 0.464 ± 0.024 | 0.151 ± 0.018 | 14.4 ± 11.2% | 0.793 ± 0.156 |
| P Value | **0.001** | **<0.001** | 0.157 | 0.101 | 0.450 | 0.449 | 0.111 | **<0.001** | **<0.001** | **<0.001** | 0.353 | **0.015** |

FIG. 31

| Instability Cohorts | Deltoid Normalized Volume | Deltoid Elongation | Deltoid Flatness | Deltoid Least Axis Length | Deltoid Major Axis Length | Deltoid Max 2D Diameter, Column | Deltoid Max 2D Diameter, Row | Deltoid Mesh Volume ($cm^3$) | Deltoid Sphericity | Deltoid Surface to Volume Ratio | Deltoid Fat Percentage | Deltoid 10th Percentile HU, 1° Order |
|---|---|---|---|---|---|---|---|---|---|---|---|---|
| Stable rTSA Patients | 1.00 ± 0.19 | 0.799 ± 0.071 | 0.469 ± 0.045 | 68.2 ± 8.6 | 145.4 ± 12.7 | 160.0 ± 16.2 | 133.6 ± 20.2 | 320.2 ± 106.2 | 0.454 ± 0.028 | 0.160 ± 0.023 | 15.0 ± 11.5% | 0.823 ± 0.159 |
| Unstable rTSA Patients | 1.13 ± 0.21 | 0.821 ± 0.070 | 0.487 ± 0.039 | 76.0 ± 8.3 | 156.3 ± 13.9 | 172.7 ± 14.0 | 153.6 ± 19.8 | 442.9 ± 116.8 | 0.468 ± 0.028 | 0.138 ± 0.017 | 18.3 ± 11.5% | 0.823 ± 0.136 |
| P Value | **0.016** | 0.321 | 0.176 | **0.002** | **0.005** | **0.009** | **0.001** | **<0.001** | 0.089 | 0.001 | 0.349 | 0.987 |

FIG. 32

| Scapula Fracture Cohorts | Scapula Elongation | Scapula Flatness | Scapula Least Axis Length (mm) | Scapula Minor Axis Length (mm) | Scapula Max 2D Diameter, Column (mm) | Scapula Max 2D Diameter, Row (mm) | Scapula Max 2D Diameter, Slice (mm) | Scapula Mesh Volume ($cm^3$) | Scapula Sphericity | Scapula Surface to Volume Ratio | Scapula 10th Percentile | Scapula NGTDM Strength |
|---|---|---|---|---|---|---|---|---|---|---|---|---|
| Non-Fx Patients | 0.509 ± 0.035 | 0.298 ± 0.028 | 54.0 ± 6.0 | 92.4 ± 8.3 | 114.1 ± 15.2 | 153.2 ± 16.9 | 130.9 ± 13.4 | 78.8 ± 25.4 | 0.232 ± 0.014 | 0.500 ± 0.069 | 0.978 ± 0.178 | 0.077 ± 0.024 |
| Scapula Fx Patients | 0.510 ± 0.029 | 0.292 ± 0.023 | 50.4 ± 4.4 | 88.0 ± 5.6 | 109.6 ± 14.7 | 144.6 ± 14.9 | 123.6 ± 12.1 | 61.3 ± 16.4 | 0.226 ± 0.012 | 0.551 ± 0.052 | 1.024 ± 0.167 | 0.096 ± 0.021 |
| P Value | 0.917 | 0.329 | **0.004** | **0.012** | 0.154 | **0.016** | **0.009** | **0.001** | **0.049** | **<0.001** | 0.219 | **<0.001** |

FIG. 33

| Deltoid Cluster | Deltoid Normalized Volume | Deltoid Elongation | Deltoid Flatness | Deltoid Fat Percentage | Deltoid Max 2D Diameter, Column | Deltoid Max 2D Diameter, Row | Deltoid Sphericity | Deltoid 10th Percentile, 1st Order | Patient Age (yrs) | Patient BMI | Diagnosis OA % | Diagnosis RCT % | Diagnosis RCT % | Prosthesis Type, rTSA % |
|---|---|---|---|---|---|---|---|---|---|---|---|---|---|---|
| Cluster 0, Male (n=257) | 0.99 ± 0.14 | 0.82 ± 0.06 | 0.50 ± 0.03 | 10.8 ± 10.5 | 180.3 ± 10.7 | 163.2 ± 14.2 | 0.43 ± 0.02 | 0.88 ± 0.14 | 73.6 ± 6.7 | 26.8 ± 3.4 | 62.6% | 17.9% | 30.4% | 80.5% |
| Cluster 1, Male (n=294) | 0.83 ± 0.13 | 0.83 ± 0.06 | 0.47 ± 0.03 | 10.4 ± 10.3 | 163.5 ± 11.2 | 135.4 ± 12.0 | 0.45 ± 0.02 | 0.86 ± 0.14 | 70.9 ± 8.1 | 28.6 ± 4.8 | 69.0% | 16.7% | 23.5% | 78.2% |
| Cluster 2, Male (n=272) | 1.08 ± 0.15 | 0.82 ± 0.05 | 0.45 ± 0.03 | 18.8 ± 10.5 | 182.4 ± 10.9 | 146.9 ± 12.7 | 0.47 ± 0.02 | 0.71 ± 0.15 | 66.3 ± 7.8 | 32.4 ± 5.5 | 80.9% | 14.3% | 15.4% | 61.8% |
| Cluster 3, Male (n=270) | 1.11 ± 0.17 | 0.90 ± 0.04 | 0.50 ± 0.04 | 13.3 ± 10.9 | 169.7 ± 9.4 | 151.7 ± 11.9 | 0.48 ± 0.02 | 0.79 ± 0.14 | 66.1 ± 8 | 31.0 ± 5.0 | 64.4% | 14.8% | 33.0% | 70.4% |
| Cluster 0, Female (n=443) | 0.95 ± 0.15 | 0.79 ± 0.06 | 0.49 ± 0.04 | 9.3 ± 9.0 | 150.2 ± 9.6 | 135.3 ± 13.7 | 0.43 ± 0.02 | 0.93 ± 0.14 | 73.7 ± 7.5 | 24.7 ± 4.1 | 67.7% | 15.1% | 26.4% | 83.3% |
| Cluster 1, Female (n=318) | 1.13 ± 0.18 | 0.75 ± 0.05 | 0.44 ± 0.03 | 18.6 ± 10.9 | 166.4 ± 9.9 | 125.5 ± 15.1 | 0.46 ± 0.02 | 0.75 ± 0.13 | 67.6 ± 7.9 | 32.3 ± 6.2 | 71.7% | 16.7% | 21.1% | 68.6% |
| Cluster 2, Female (n=409) | 0.87 ± 0.13 | 0.73 ± 0.05 | 0.43 ± 0.03 | 15.1 ± 11.1 | 148.7 ± 9.9 | 110.2 ± 10.5 | 0.45 ± 0.02 | 0.84 ± 0.15 | 72.8 ± 7.1 | 29.6 ± 5.6 | 73.8% | 13.9% | 19.1% | 81.2% |
| Cluster 3, Female (n=324) | 1.10 ± 0.16 | 0.82 ± 0.05 | 0.47 ± 0.04 | 21.5 ± 10.8 | 146.2 ± 9.2 | 121.2 ± 11.6 | 0.48 ± 0.02 | 0.74 ± 0.14 | 69.1 ± 8.4 | 32.9 ± 6.7 | 58.3% | 24.1% | 30.6% | 81.8% |

FIG. 34

| Deltoid Cluster | Active Abduction | Active Forward Elevation | IR Score | Active External Rotation | VAS Pain | Global Shoulder Function | Constant | ASES | SAS |
|---|---|---|---|---|---|---|---|---|---|
| Cluster 0, Male (n=257) | 81.5 ± 36.9 | 97.2 ± 39.2 | 3.4 ± 1.7 | 25.2 ± 22.5 | 5.7 ± 2.2 | 4.4 ± 2.3 | 43.1 ± 15.2 | 42.2 ± 16.1 | 50.5 ± 11.8 |
| Cluster 1, Male (n=294) | 85.2 ± 35.5 | 97.3 ± 36.7 | 3.2 ± 1.8 | 24.0 ± 20.3 | 5.6 ± 2.3 | 4.4 ± 1.8 | 42.5 ± 14.9 | 41.7 ± 15.2 | 49.4 ± 10.7 |
| Cluster 2, Male (n=272) | 94.6 ± 40.2 | 104.2 ± 36.2 | 3.0 ± 1.9 | 25.4 ± 21.3 | 5.8 ± 2.3 | 4.5 ± 2.0 | 42.7 ± 15.5 | 41.6 ± 15.6 | 49.2 ± 12.2 |
| Cluster 3, Male (n=270) | 99.4 ± 39.0 | 112.0 ± 36.7 | 3.5 ± 1.7 | 26.2 ± 21.5 | 5.8 ± 2.2 | 4.7 ± 1.9 | 47.3 ± 15.9 | 42.2 ± 15.4 | 52.4 ± 11.0 |
| **ANOVA P-Value** | **<0.001** | **<0.001** | **0.019** | 0.580 | 0.933 | 0.342 | **0.011** | 0.840 | **0.005** |
| **P Value (0M vs 3M)** | **<0.001** | **<0.001** | 0.661 | NA | NA | NA | **0.011** | NA | 0.072 |
| Cluster 0, Female (n=443) | 79.7 ± 34.4 | 97.3 ± 37.1 | 3.5 ± 1.8 | 24.9 ± 21.8 | 6.3 ± 2.2 | 3.9 ± 2.1 | 39.5 ± 14.5 | 37.6 ± 15.7 | 48.2 ± 12.4 |
| Cluster 1, Female (n=318) | 90.4 ± 37.0 | 99.4 ± 35.2 | 3.1 ± 1.8 | 27.5 ± 20.7 | 6.4 ± 2.1 | 4.3 ± 2.0 | 38.7 ± 14.0 | 35.2 ± 15.0 | 47.4 ± 12.3 |
| Cluster 2, Female (n=409) | 75.2 ± 33.7 | 86.2 ± 35.5 | 2.6 ± 1.8 | 19.3 ± 20.0 | 6.7 ± 2.2 | 3.8 ± 2.2 | 34.2 ± 14.3 | 33.0 ± 15.5 | 42.7 ± 12.4 |
| Cluster 3, Female (n=324) | 84.8 ± 40.3 | 96.3 ± 40.8 | 3.1 ± 1.9 | 23.7 ± 21.3 | 6.4 ± 2.1 | 4.1 ± 2.2 | 35.9 ± 14.7 | 33.9 ± 14.7 | 46.4 ± 12.8 |
| **ANOVA P-Value** | **<0.001** | **<0.001** | **<0.001** | **<0.001** | **0.025** | **0.005** | **<0.001** | **<0.001** | **<0.001** |
| **P Value (1F vs 2F)** | **<0.001** | **<0.001** | **<0.001** | **<0.001** | **0.048** | **0.002** | **<0.001** | 0.073 | **<0.001** |

FIG. 35

| Deltoid Cluster | Active Abduction | Active Forward Elevation | IR Score | Active External Rotation | VAS Pain | Global Shoulder Function | Constant | ASES | SAS |
|---|---|---|---|---|---|---|---|---|---|
| Cluster 0, Male (n=257) | 128.9 ± 26.0 | 145.2 ± 21.2 | 4.3 ± 1.7 | 43.7 ± 18.2 | 1.1 ± 2.1 | 8.5 ± 1.9 | 71.9 ± 13.5 | 84.6 ± 17.6 | 75.1 ± 11.4 |
| Cluster 1, Male (n=294) | 126.8 ± 31.6 | 145.0 ± 23.3 | 3.9 ± 1.7 | 42.1 ± 20.7 | 1.3 ± 2.0 | 8.2 ± 2.1 | 69.5 ± 14.6 | 83.6 ± 18.0 | 74.1 ± 12.4 |
| Cluster 2, Male (n=272) | 145.1 ± 23.3 | 151.3 ± 18.3 | 4.7 ± 1.4 | 50.5 ± 18.3 | 1.2 ± 2.2 | 8.6 ± 1.7 | 75.0 ± 12.1 | 86.2 ± 17.8 | 78.4 ± 10.3 |
| Cluster 3, Male (n=270) | 134.9 ± 25.1 | 149.9 ± 17.4 | 4.4 ± 1.7 | 47.0 ± 18.8 | 1.4 ± 2.3 | 8.3 ± 2.1 | 73.8 ± 13.5 | 84.0 ± 19.0 | 75.5 ± 11.8 |
| **ANOVA P-Value** | **<0.001** | 0.202 | **0.016** | **0.012** | 0.418 | 0.626 | 0.061 | 0.652 | 0.104 |
| **P Value (1M vs 2M)** | **<0.001** | NA | **<0.001** | **0.003** | NA | NA | NA | NA | NA |
| Cluster 0, Female (n=443) | 125.1 ± 27.7 | 148.2 ± 23.4 | 5.0 ± 1.4 | 44.2 ± 20.0 | 1.3 ± 2.1 | 8.5 ± 1.9 | 70.1 ± 12.8 | 84.8 ± 17.9 | 77.5 ± 12.2 |
| Cluster 1, Female (n=318) | 131.3 ± 32.5 | 143.1 ± 27.0 | 4.7 ± 1.5 | 48.2 ± 17.2 | 1.4 ± 2.3 | 8.2 ± 2.1 | 68.2 ± 14.1 | 81.8 ± 19.6 | 75.4 ± 11.9 |
| Cluster 2, Female (n=409) | 128.3 ± 30.8 | 142.6 ± 27.9 | 4.6 ± 1.6 | 44.8 ± 17.9 | 1.0 ± 1.9 | 8.5 ± 1.8 | 66.6 ± 14.8 | 84.9 ± 16.3 | 75.5 ± 12.1 |
| Cluster 3, Female (n=324) | 129.1 ± 34.8 | 140.6 ± 29.2 | 4.2 ± 1.8 | 45.5 ± 20.2 | 1.4 ± 2.1 | 7.9 ± 2.1 | 63.6 ± 14.7 | 80.1 ± 18.7 | 72.6 ± 13.0 |
| **ANOVA P-Value** | 0.091 | **0.039** | **<0.001** | 0.099 | 0.265 | **0.004** | **0.001** | **0.026** | **0.003** |
| **P Value (0F vs 3F)** | NA | **0.010** | **<0.001** | NA | NA | **0.003** | **<0.001** | **0.015** | **<0.001** |

FIG. 36

| Scapula Cluster | Scapula Elongation | Scapula Flatness | Scapula Least Axis Length (mm) | Scapula Max 2D Diameter, Column (mm) | Scapula Max 2D Diameter, Row (mm) | Scapula Max 2D Diameter, Slice (mm) | Scapula Sphericity | Scapula $10^{th}$ Percentile, $1^{st}$ Order | Patient Age (yrs) | Patient BMI | Diagnosis OA % | Diagnosis RCT % | Diagnosis RCT % | Prosthesis Type, rTSA % |
|---|---|---|---|---|---|---|---|---|---|---|---|---|---|---|
| Cluster 0, Male (n=579) | 0.50 ± 0.03 | 0.28 ± 0.02 | 54.8 ± 2.9 | 118.3 ± 8.7 | 158.2 ± 9.6 | 135.5 ± 9.2 | 0.24 ± 0.01 | 1.01 ± 0.17 | 66.5 ± 9.1 | 29.5 ± 5.3 | 75.3% | 13.1% | 18.8% | 60.8% |
| Cluster 1, Male (n=218) | 0.50 ± 0.03 | 0.30 ± 0.02 | 59.9 ± 4.2 | 143.5 ± 12.1 | 180.5 ± 13.3 | 131.1 ± 9.9 | 0.23 ± 0.01 | 0.93 ± 0.18 | 71.1 ± 8.1 | 30.3 ± 6.0 | 50.0% | 22.0% | 45.4% | 86.7% |
| Cluster 2, Male (n=549) | 0.49 ± 0.02 | 0.30 ± 0.02 | 60.3 ± 3.0 | 121.9 ± 8.1 | 166.9 ± 9.7 | 146.1 ± 9.8 | 0.23 ± 0.01 | 0.94 ± 0.17 | 70.8 ± 7.6 | 29.4 ± 4.7 | 69.8% | 13.7% | 25.7% | 74.7% |
| Cluster 3, Male (n=267) | 0.54 ± 0.04 | 0.33 ± 0.04 | 62.6 ± 3.6 | 124.7 ± 8.8 | 161.0 ± 13.6 | 146.2 ± 10.6 | 0.24 ± 0.01 | 0.96 ± 0.17 | 65.7 ± 8.0 | 31.2 ± 5.7 | 79.4% | 11.6% | 18.4% | 58.1% |
| Cluster 0, Female (n=511) | 0.50 ± 0.03 | 0.29 ± 0.02 | 50.2 ± 2.4 | 100.2 ± 7.0 | 141.9 ± 9.5 | 129.9 ± 9.2 | 0.23 ± 0.01 | 0.97 ± 0.16 | 74.7 ± 6.2 | 28.5 ± 6.1 | 67.9% | 16.6% | 24.3% | 85.5% |
| Cluster 1, Female (n=363) | 0.54 ± 0.04 | 0.33 ± 0.03 | 52.8 ± 3.0 | 104.9 ± 7.4 | 140.8 ± 11.2 | 126.3 ± 9.7 | 0.24 ± 0.01 | 0.95 ± 0.17 | 70.8 ± 7.3 | 30.5 ± 6.6 | 74.4% | 18.2% | 20.1% | 78.2% |
| Cluster 2, Female (n=318) | 0.51 ± 0.03 | 0.29 ± 0.02 | 51.9 ± 3.1 | 117.7 ± 10.1 | 154.9 ± 11.8 | 123.0 ± 11.2 | 0.22 ± 0.01 | 1.00 ± 0.19 | 68.9 ± 8.6 | 30.0 ± 7.7 | 60.1% | 18.2% | 34.6% | 88.1% |
| Cluster 3, Female (n=535) | 0.51 ± 0.03 | 0.28 ± 0.02 | 46.3 ± 2.4 | 101.5 ± 8.4 | 137.8 ± 9.2 | 118.1 ± 9.1 | 0.24 ± 0.01 | 1.05 ± 0.19 | 68.5 ± 8.1 | 29.8 ± 7.1 | 73.3% | 15.3% | 19.1% | 67.3% |

FIG. 37

| Scapula Cluster | Active Abduction | Active Forward Elevation | IR Score | Active External Rotation | VAS Pain | Global Shoulder Function | Constant | ASES | SAS |
|---|---|---|---|---|---|---|---|---|---|
| Cluster 0, Male (n=579) | 94.3 ± 36.4 | 107.0 ± 35.3 | 3.5 ± 1.7 | 26.2 ± 21.2 | 5.9 ± 2.2 | 4.6 ± 2.0 | 47.3 ± 15.4 | 41.8 ± 15.8 | 51.4 ± 11.3 |
| Cluster 1, Male (n=218) | 88.3 ± 40.9 | 97.9 ± 41.4 | 3.6 ± 1.9 | 26.2 ± 22.1 | 5.5 ± 2.3 | 4.2 ± 2.0 | 42.7 ± 15.9 | 43.1 ± 16.8 | 50.9 ± 11.8 |
| Cluster 2, Male (n=549) | 91.2 ± 39.2 | 103.4 ± 37.4 | 3.3 ± 1.7 | 23.5 ± 21.5 | 5.5 ± 2.3 | 4.6 ± 2.1 | 44.7 ± 15.5 | 43.4 ± 16.6 | 50.5 ± 11.5 |
| Cluster 3, Male (n=267) | 92.5 ± 35.9 | 107.0 ± 35.2 | 3.1 ± 1.7 | 22.4 ± 22.7 | 5.8 ± 2.2 | 4.6 ± 1.8 | 45.0 ± 15.2 | 41.0 ± 15.7 | 49.6 ± 11.2 |
| **ANOVA P-Value** | 0.097 | **0.018** | **0.004** | 0.085 | 0.083 | **0.041** | **0.010** | 0.222 | 0.230 |
| **P Value (0M vs 1M)** | NA | **0.002** | 0.569 | NA | NA | **0.016** | **0.003** | NA | NA |
| Cluster 0, Female (n=511) | 78.8 ± 33.2 | 93.8 ± 34.8 | 3.0 ± 1.8 | 20.3 ± 21.2 | 6.1 ± 2.2 | 4.2 ± 2.1 | 38.2 ± 13.4 | 37.3 ± 15.7 | 46.3 ± 11.8 |
| Cluster 1, Female (n=363) | 82.9 ± 37 | 95.2 ± 36.4 | 3.0 ± 1.9 | 24.1 ± 21.9 | 6.6 ± 2.1 | 4 ± 2.1 | 37.8 ± 14.4 | 34.5 ± 15.3 | 46.1 ± 12.4 |
| Cluster 2, Female (n=318) | 79.9 ± 39.4 | 91.7 ± 39.8 | 3.3 ± 1.9 | 25.2 ± 22.9 | 6.3 ± 2.2 | 3.9 ± 2.1 | 35.8 ± 15.2 | 35.5 ± 15.9 | 46.6 ± 13.6 |
| Cluster 3, Female (n=535) | 85.6 ± 35.9 | 96.2 ± 36.2 | 3.1 ± 1.9 | 24.2 ± 20.5 | 6.7 ± 2.1 | 4.2 ± 2.1 | 37.3 ± 14.6 | 33.8 ± 15.6 | 45.8 ± 12.9 |
| **ANOVA P-Value** | **0.005** | 0.176 | 0.378 | **0.005** | **<0.001** | 0.194 | 0.173 | **0.006** | 0.865 |
| **P Value (0F vs 3F)** | **0.002** | NA | NA | **0.003** | **<0.001** | NA | NA | **<0.001** | NA |

FIG. 38

| Scapula Cluster | Active Abduction | Active Forward Elevation | IR Score | Active External Rotation | VAS Pain | Global Shoulder Function | Constant | ASES | SAS |
|---|---|---|---|---|---|---|---|---|---|
| Cluster 0, Male (n=579) | 132.2 ± 28.9 | 148.0 ± 24.0 | 4.5 ± 1.6 | 47.3 ± 18.4 | 1.1 ± 1.9 | 8.6 ± 1.8 | 72.3 ± 15.1 | 86.3 ± 16.7 | 77.5 ± 11.8 |
| Cluster 1, Male (n=218) | 130.9 ± 26.8 | 142.6 ± 24.8 | 4.2 ± 1.7 | 42.4 ± 19.9 | 1.4 ± 2.1 | 8.2 ± 2.0 | 69.8 ± 16.6 | 81.8 ± 20.0 | 74.7 ± 12.2 |
| Cluster 2, Male (n=549) | 134.6 ± 27.9 | 148.3 ± 22.2 | 4.1 ± 1.6 | 44.5 ± 17.9 | 1.2 ± 2.1 | 8.4 ± 1.8 | 71.9 ± 12.9 | 85.7 ± 17.0 | 76.8 ± 10.4 |
| Cluster 3, Male (n=267) | 138.7 ± 31.0 | 148.6 ± 27.0 | 4.3 ± 1.7 | 47.7 ± 20.0 | 0.9 ± 1.8 | 8.7 ± 1.8 | 71.8 ± 14.7 | 87.7 ± 15.9 | 78.5 ± 11.8 |
| **ANOVA P-Value** | 0.062 | 0.094 | 0.126 | 0.219 | 0.309 | 0.119 | 0.834 | 0.107 | 0.055 |
| Cluster 0, Female (n=511) | 128.2 ± 29.8 | 144.9 ± 25.6 | 4.6 ± 1.6 | 42.1 ± 20.1 | 1.1 ± 2.0 | 8.4 ± 2.0 | 67.1 ± 13.8 | 84.1 ± 17.1 | 76.6 ± 11.7 |
| Cluster 1, Female (n=363) | 127.8 ± 30.9 | 141.6 ± 27.8 | 4.6 ± 1.6 | 45.1 ± 18.5 | 1.0 ± 1.8 | 8.5 ± 1.8 | 66.5 ± 13.4 | 84.6 ± 16.1 | 76.4 ± 11.1 |
| Cluster 2, Female (n=318) | 124.0 ± 30.1 | 140.9 ± 27.1 | 4.6 ± 1.8 | 45.6 ± 18.7 | 1.3 ± 2.0 | 8.2 ± 1.9 | 68.5 ± 13.4 | 81.9 ± 18.0 | 76.0 ± 12.7 |
| Cluster 3, Female (n=535) | 129.4 ± 32.9 | 143.6 ± 28.1 | 4.7 ± 1.5 | 47.7 ± 18.7 | 1.4 ± 2.3 | 8.2 ± 2.2 | 66.7 ± 14.9 | 82.2 ± 19.4 | 75.8 ± 12.3 |
| **ANOVA P-Value** | 0.186 | 0.310 | 0.738 | **0.011** | 0.137 | 0.221 | 0.693 | 0.241 | 0.934 |
| **P Value (0F vs 3F)** | NA | NA | NA | **<0.001** | NA | NA | NA | NA | NA |

FIG. 39

METHODS AND SYSTEMS FOR UTILIZING RADIOMIC-BASED MEASUREMENTS WITHIN A CLINICAL DECISION SUPPORT TOOL

FIELD

The present disclosure relates to machine learning modeling for medical applications, and more specifically to methods and systems for utilizing radiomic-based measurements (and other image-based measurements) within a clinical decision support tool.

BACKGROUND

Supervised machine learning is a class of artificial intelligence by which the computer learns the complex structure and relationships in large datasets to create predictive models with the help of labeled features. The machine learning model iteratively learns using the feature data to minimize predictive error. There are numerous commercial applications of various machine learning techniques.

DRAWINGS

Some embodiments of the disclosure are herein described, by way of example only, with reference to the accompanying drawings. With specific reference now to the drawings in detail, it is stressed that the embodiments shown are by way of example and for purposes of illustrative discussion of embodiments of the disclosure. In this regard, the description taken with the drawings makes apparent to those skilled in the art how embodiments of the disclosure may be practiced.

FIG. 1 is a block diagram of a system for utilizing radiomic-based measurements within a clinical decision support tool in accordance with one or more embodiments of the present disclosure;

FIG. 2 illustrates 3D reconstructions of the scapula, proximal humerus, deltoid muscle, and rotator cuff muscles (left), with select radiomic measurements of the deltoid are extracted and presented (left), and also with the deltoid removed (right) to show the supraspinatus, infraspinatus, and subscapularis rotator cuff muscles (right), in this example (right) select radiomic measures of the supraspinatus, infraspinatus, and subscapularis rotator cuff muscles are extracted and presented in accordance with one or more embodiments of the present disclosure;

FIG. 3 illustrates 3D reconstructions of the scapula, proximal humerus, and deltoid muscle (left), with segmentation of the 3D muscle volume into anatomically relevant sub-volumes of the deltoid (anterior, middle, and posterior deltoid) for localized radiomic analysis (right), select radiomic measures of the middle deltoid are extracted and presented in accordance with one or more embodiments of the present disclosure;

FIG. 4 illustrates multiple views of 3D reconstructions of a scapular bone (left), with segmentation/partitioning of the 3D volume into anatomically relevant sub-volumes of scapular bone segments for localized radiomic analysis (middle), in this example (right), select radiomic measures of the glenoid vault are extracted and presented in accordance with one or more embodiments of the present disclosure;

FIG. 5 illustrates multiple views of 3D reconstructions of the proximal humerus (left), with segmentation/partitioning of the 3D volume into anatomically relevant sub-volumes of the proximal humeral bone segments for localized radiomic analysis (middle), in this example (right), select radiomic measures of the proximal humeral metaphysis and humeral head are extracted and presented in accordance with one or more embodiments of the present disclosure;

FIG. 6 is a Scatter Plot of Pre-operative Abduction vs. Deltoid Volume Normalized by Age and Gender (left), with Corresponding 3D CT Reconstructed Deltoids Representative (i.e. Near) of the Centroid of each of the 4 Female Deltoid Cluster Cohorts. Note that Female Deltoid Cluster F1 is associated with Significantly more Pre-operative Abduction than Female Deltoid Cluster F2, as shown in the Table of FIG. 35 below in accordance with one or more embodiments of the present disclosure;

FIG. 7 is a Scatter Plot of 2-year Minimum Abduction vs. Deltoid Volume Normalized by Age and Gender (left), with Corresponding 3D CT Reconstructed Deltoids Representative (i.e. Near) of the Centroid of each of the 4 Male Deltoid Cluster Cohorts. Note that Male Deltoid Cluster M2 is associated with Significantly more 2-year Minimum Abduction than Male Deltoid Cluster M1, as shown in the Table of FIG. 36 below. in accordance with one or more embodiments of the present disclosure;

FIG. 8 illustrates 3D CT Reconstructed Scapula Representative (i.e. Near) of the Centroid of each of the 4 Female (Left) and 4 Male (Right) Deltoid Cluster Cohorts in accordance with one or more embodiments of the present disclosure;

FIG. 9 illustrates Multiple views of 3D reconstructions of a scapular bone (left), with segmentation/partitioning of the 3D volume into anatomically relevant sub-volumes of scapular bone segments for localized radiomic analysis (middle), in this example (right), outlier image-based measurements (relative to a patient reference group) of the glenoid vault are identified and displayed for visual interpretation in accordance with one or more embodiments of the present disclosure;

FIG. 10 illustrates multiple views of 3D reconstructions of a scapular bone (left), with segmentation/partitioning of the 3D volume into anatomically relevant sub-volumes of scapular bone segments for localized radiomic analysis (middle), in this example (right), outlier image-based measurements (relative to a patient reference group) of the acromion are identified and displayed for visual interpretation in accordance with one or more embodiments of the present disclosure;

FIG. 11 illustrates multiple views of 3D reconstructions of the proximal humerus (left), with segmentation/partitioning of the 3D volume into anatomically relevant sub-volumes of the proximal humeral bone segments for localized radiomic analysis (middle), in this example (right) outlier image-based measurements (relative to a patient reference group) of the proximal humerus are identified and displayed for visual interpretation in accordance with one or more embodiments of the present disclosure;

FIG. 12 illustrates 3D reconstructions of the scapula, proximal humerus, and deltoid muscle (left), with segmentation/partitioning of the 3D muscle volume into anatomically relevant sub-volumes of the deltoid (middle deltoid, middle) for localized radiomic analysis (right), in this example (right) outlier image-based measurements (relative to a patient reference group) of the middle deltoid are identified and displayed for visual interpretation in accordance with one or more embodiments of the present disclosure;

FIG. 13 illustrates 3D reconstructions of the scapula, proximal humerus, deltoid muscle, and rotator cuff muscles (left), with deltoid removed (middle, and with the supraspinatus rotator cuff muscle (right) highlighted for localized radiomic analysis (right), in this example (right) select radiomic measures of the supraspinatus are extracted and presented in tabular format relative to outlier image-based measurements (relative to a patient reference group) of the supraspinatus are identified and displayed for visual interpretation in accordance with one or more embodiments of the present disclosure;

FIG. 14 illustrates 3D reconstructions of the scapula, proximal humerus, and deltoid muscle. The table below the reconstruction displays the extracted radiomic measures of the patient's deltoid muscle and compares image-based measurements relative to a control/reference patient cohort of deltoid radiomic measures to provide the physician and/or health care professional context of this patient's image-based measurements in accordance with one or more embodiments of the present disclosure;

FIG. 15 is a table showing Definitions of PyRadiomics Radiomic Feature Measurements in accordance with one or more embodiments of the present disclosure;

FIG. 16 is a table showing CT image processing parameters used for the 7 different methods for the Deltoid muscle and Scapular bone sensitivity study in accordance with one or more embodiments of the present disclosure;

FIG. 17 is a table showing PyRadiomics radiomic features deemed robust, stable, and unique/non-redundant after sensitivity analysis and correlation study for the Deltoid muscle in accordance with one or more embodiments of the present disclosure;

FIG. 18 is a table showing PyRadiomics radiomic features deemed robust, stable, and unique/non-redundant after sensitivity analysis and correlation study for the Scapular Bone in accordance with one or more embodiments of the present disclosure;

Figure 1:
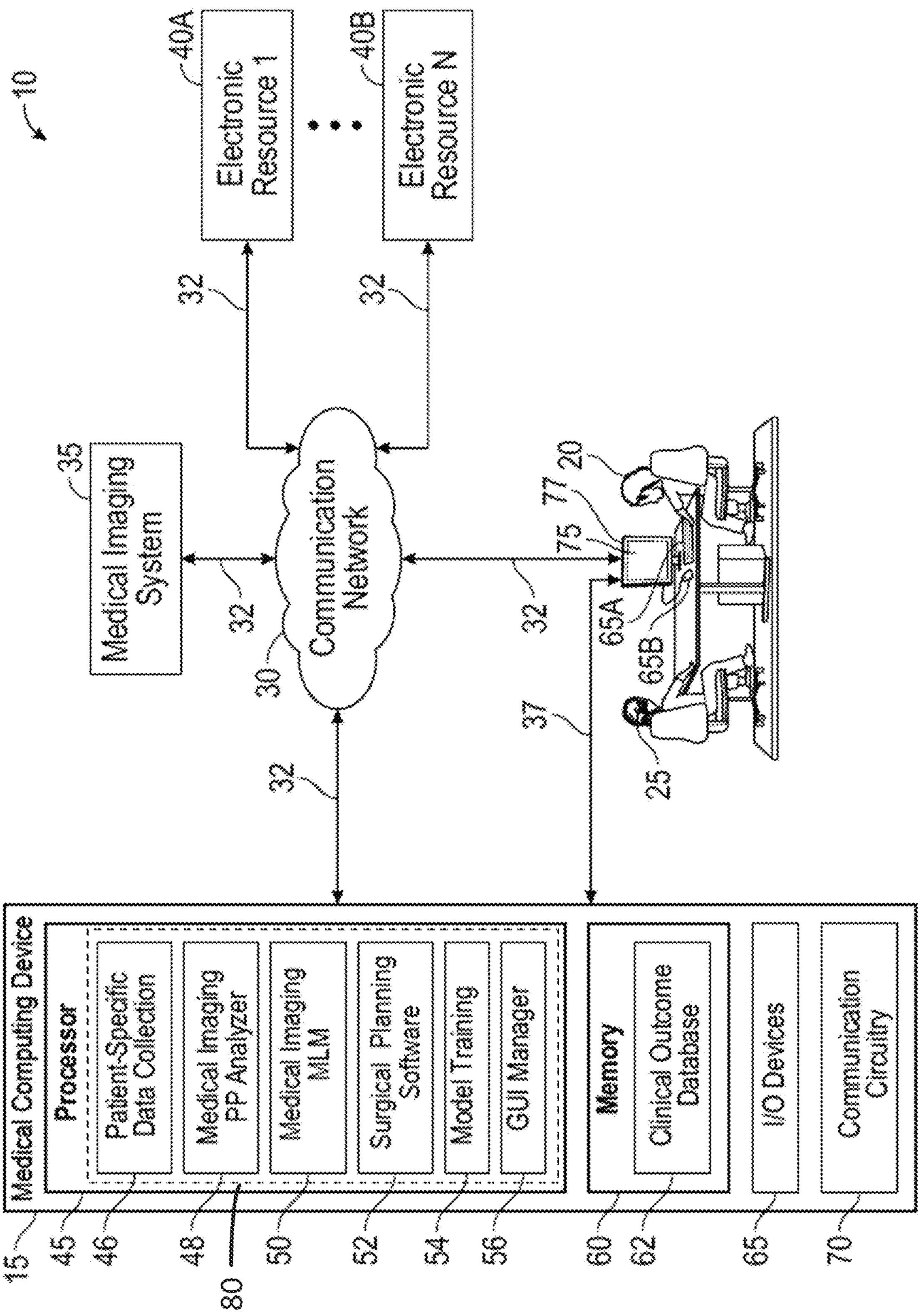
Figure 40:
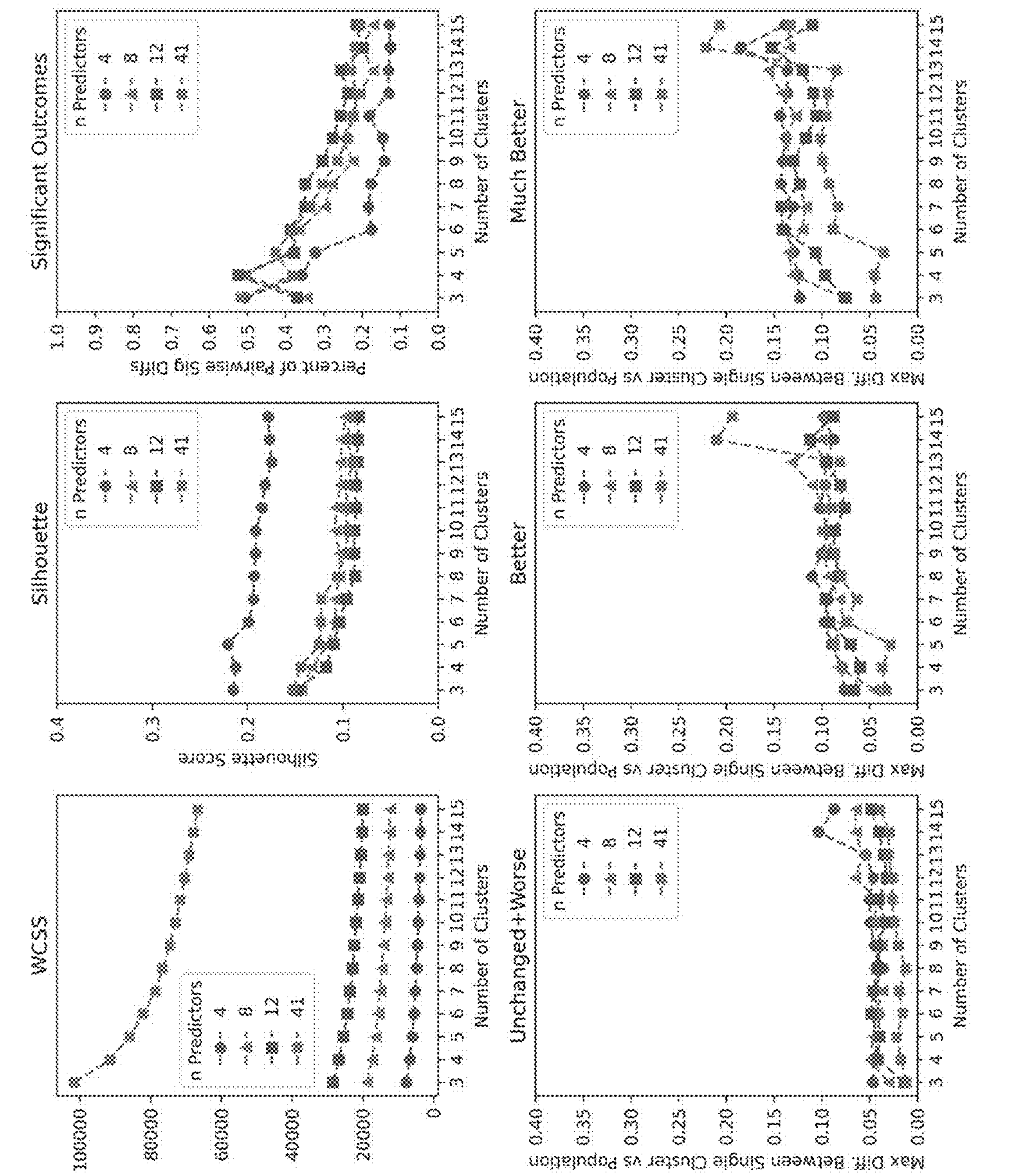
Figure 41:
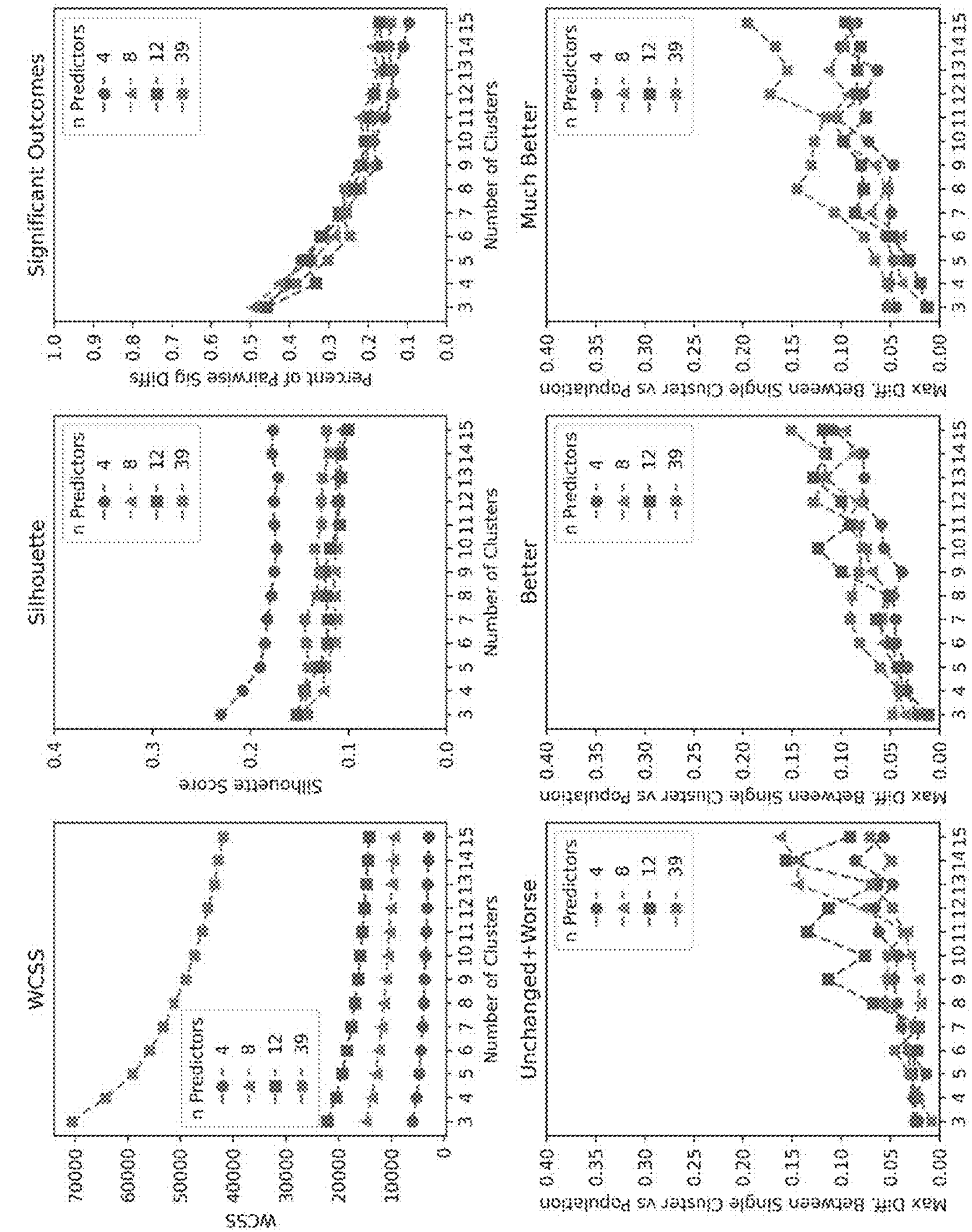
Figure 42:
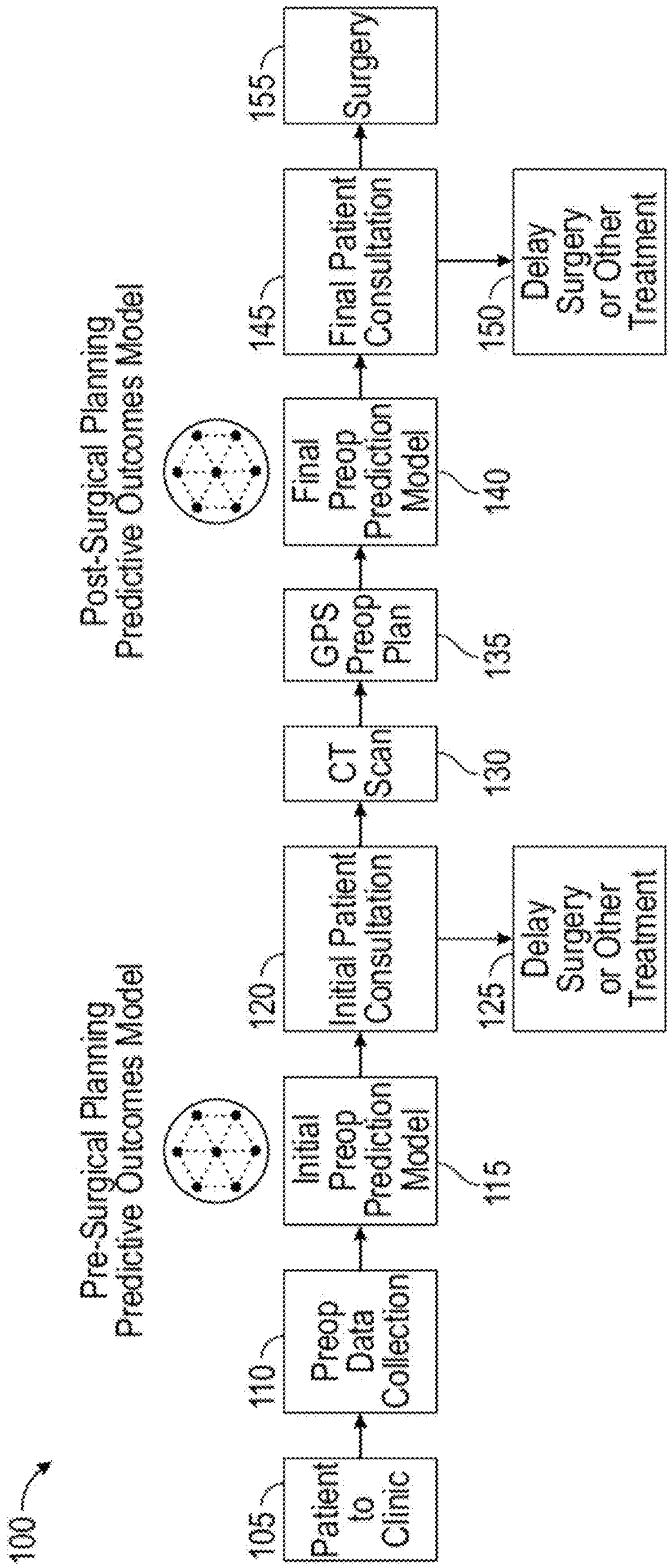
Figure 43:
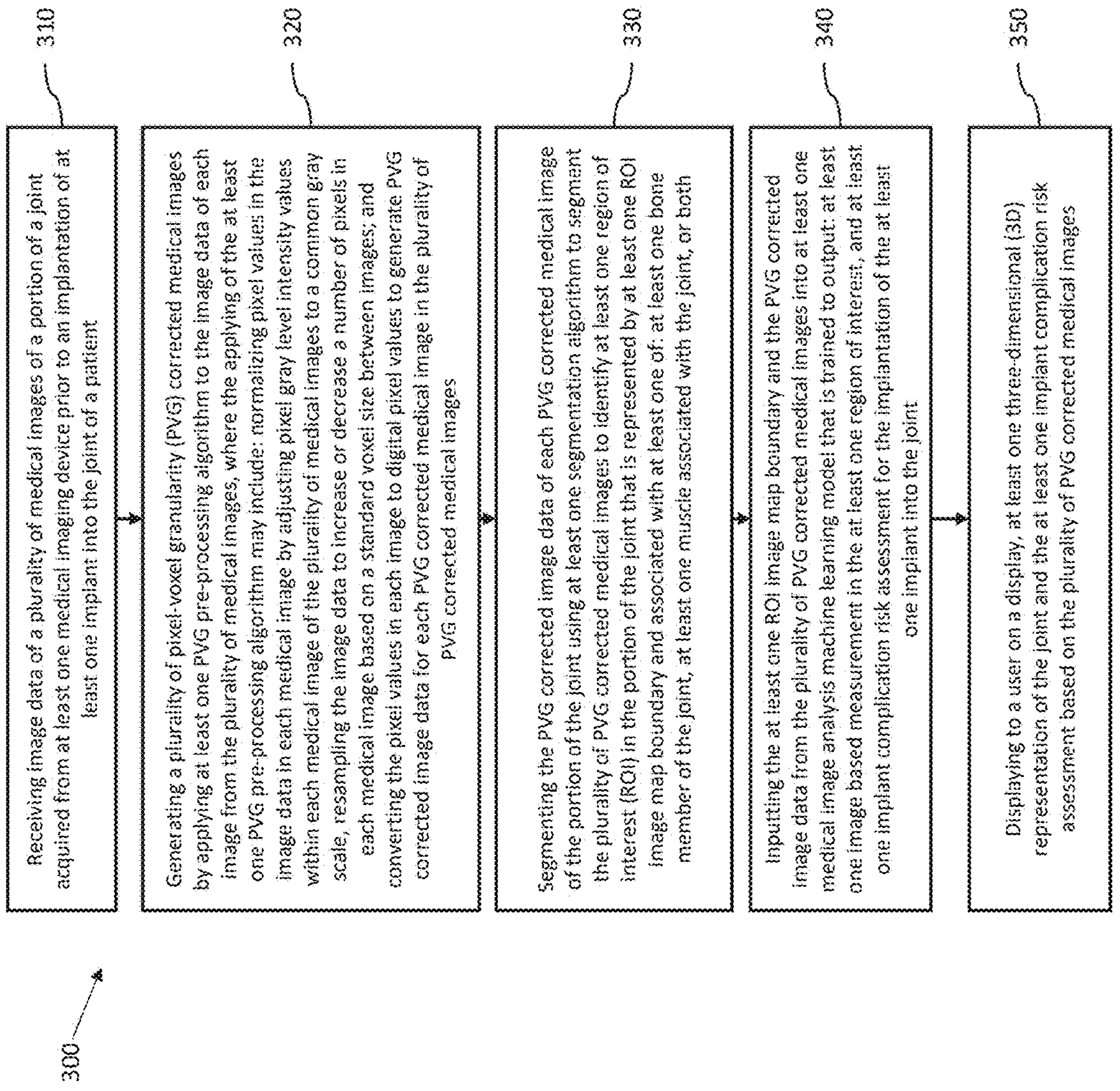

FIG. 19 is a table showing a comparison of the Mean Absolute Error (MAE) Associated with 2 Different Machine Learning Models (Deltoid Muscle Image data vs. No radiomic image data) to Predict Clinical Outcomes, Pre-operatively, 3 months, 6 months, 1 yr, 2-3 yrs, and 3-5 yrs after Anatomic Total Shoulder Arthroplasty (aTSA) and Reverse Total Shoulder Arthroplasty (rTSA) in accordance with one or more embodiments of the present disclosure;

FIG. 20 is a table showing Classification Predictions Performance Associated with 2 Different Machine Learning Models (Deltoid Muscle Image data vs. No radiomic image data) to Predict aTSA and rTSA clinical improvement at 2-3 years follow-up greater than the Minimal Clinically Important Difference (MCID) threshold for multiple different outcome measures in accordance with one or more embodiments of the present disclosure;

FIG. 21 is a table showing Classification Predictions Performance Associated with 2 Different Machine Learning Models (Deltoid Muscle Image data vs. No radiomic image data) to Predict aTSA and rTSA clinical improvement at 2-3 years follow-up greater than the substantial clinical benefit (SCB) threshold for multiple different outcome measures in accordance with one or more embodiments of the present disclosure;

FIG. 22 is a table showing a comparison of the Mean Absolute Error (MAE) Associated with 2 Different Machine Learning Models (Scapular Bone Image data vs. No radiomic image data) to Predict Clinical Outcomes, Pre-operatively, 3 months, 6 months, 1 yr, 2-3 yrs, and 3-5 yrs after aTSA and rTSA in accordance with one or more embodiments of the present disclosure;

FIG. 23 is a table showing Classification Predictions Performance Associated with 2 Different Machine Learning Models (Scapular Bone Image data vs. No radiomic image data) to Predict aTSA and rTSA clinical improvement at 2-3 years follow-up greater than the MCID threshold for multiple different outcome measures in accordance with one or more embodiments of the present disclosure;

FIG. 24 is a table showing Classification Predictions Performance Associated with 2 Different Machine Learning Models (Scapular Bone Image model vs. No radiomic image data) to Predict aTSA and rTSA clinical improvement at 2-3 years follow-up greater than the SCB threshold for multiple different outcome measures in accordance with one or more embodiments of the present disclosure;

FIG. 25 is a table showing Comparison of the Top 20 Preoperative Model Inputs (by F-Score Ranking) Used to Predict Pre-operative Clinical Outcomes Using the Deltoid Muscle Model in accordance with one or more embodiments of the present disclosure;

FIG. 26 is a table showing Comparison of the Top 20 Pre-operative Model Inputs (by F-Score Ranking) Used to Predict 2-3 year Clinical Outcomes after aTSA and rTSA Using the Deltoid Muscle Model in accordance with one or more embodiments of the present disclosure;

FIG. 27 is a table showing Comparison of Average Deltoid Muscle Radiomic Measurements Associated with Primary aTSA and rTSA Patients, Stratified by Gender and Age at the Time of Surgery in accordance with one or more embodiments of the present disclosure;

FIG. 28 is a table showing Comparison of the Top 20 Preoperative Model Inputs (by F-Score Ranking) Used to Predict Pre-operative Clinical Outcomes Using the Scapular Bone Model in accordance with one or more embodiments of the present disclosure;

FIG. 29 is a table showing a comparison of the Top 20 Pre-operative Model Inputs (by F-Score Ranking) Used to Predict 2-3-year Clinical Outcomes after aTSA and rTSA Using the Scapular Bone Model in accordance with one or more embodiments of the present disclosure;

FIG. 30 is a table showing a comparison of Average Scapular Bone Radiomic Measurements Associated with Primary aTSA and rTSA Patients, Stratified by Gender and Age at the Time of Surgery in accordance with one or more embodiments of the present disclosure;

FIG. 31 is a table showing a comparison of Average Deltoid Muscle Radiomic Measurements Associated with aTSA/rTSA Patients with and without High Preoperative Overhead Motion (defined as ≥160° in abduction and/or forward elevation), stratified by the prosthesis type that they would later receive in accordance with one or more embodiments of the present disclosure;

FIG. 32 is a table showing a comparison of Average Deltoid Muscle Radiomic Measurements Associated with Primary rTSA Patients with and without Adverse Event Reports of Instability in accordance with one or more embodiments of the present disclosure;

FIG. 33 is a table showing a comparison of Average Scapula Bone Radiomic Measurements Associated with Primary rTSA Patients with and without Adverse Event Reports of Scapula Fractures in accordance with one or more embodiments of the present disclosure;

FIG. 34 is a table showing a distribution of Deltoid Muscle Radiomic Measurements and Patient Demographics Associated with Male and Female Deltoid Clusters in accordance with one or more embodiments of the present disclosure;

FIG. 35 is a table showing a comparison of Deltoid Clusters to Pre-operative Clinical Outcomes Measures of Active Range of Motion, Pain, Function, and Patient Reported Outcome Measures for Male and Female Patients in accordance with one or more embodiments of the present disclosure;

FIG. 36 is a table showing a comparison of Deltoid Clusters to 2-Year Minimum Clinical Outcomes Measures of Active Range of Motion, Pain, Function, and Patient Reported Outcome Measures for Male and Female Patients in accordance with one or more embodiments of the present disclosure;

FIG. 37 is a table showing a distribution of Scapular Bone Radiomic Measurements and Patient Demographics Associated with Male and Female Deltoid Clusters in accordance with one or more embodiments of the present disclosure;

FIG. 38 is a table showing a comparison of Scapula Clusters to Pre-operative Clinical Outcomes Measures of Active Range of Motion, Pain, Function, and Patient Reported Outcome Measures for Male and Female Patients in accordance with one or more embodiments of the present disclosure;

FIG. 39 is a table showing a comparison of Scapula Clusters to 2-Year Minimum Clinical Outcomes Measures of Active Range of Motion, Pain, Function, and Patient Reported Outcome Measures for Male and Female Patients in accordance with one or more embodiments of the present disclosure;

FIG. 40 illustrates graphs of: within cluster sum of squares (WCSS) (top left), Silhouette score (top middle), the percentage of significant pairwise difference in clinical outcomes (top right), and the maximum difference in relative proportion between a single cluster and the remaining population for each of the different patient satisfaction rankings (bottom row) for various combinations of predictor variables and cluster numbers for the Scapula bone in accordance with one or more embodiments of the present disclosure;

FIG. 41 illustrates graphs of: within cluster sum of squares WCSS (top left), Silhouette score (top middle), the percentage of significant pairwise difference in clinical outcomes (top right), and the maximum difference in relative proportion between a single cluster and the remaining population for each of the different patient satisfaction rankings (bottom row) for various combinations of predictor variables and cluster numbers for the Deltoid muscle in accordance with one or more embodiments of the present disclosure;

FIG. 42 is an exemplary flow diagram 100 for modeling predictive outcomes of arthroplasty surgical procedures in accordance with one or more embodiments of the present disclosure; and FIG. 43 is a flowchart of a method for utilizing radiomic-based measurements (and other image-based measurements) within a clinical decision support tool in accordance with one or more embodiments of the present disclosure.

DETAILED DESCRIPTION

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, terms such as "comprising" "including," and "having" do not limit the scope of a specific claim to the materials or steps recited by the claim.

All prior patents, publications, and test methods referenced herein are incorporated by reference in their entireties.

Variations, modifications and alterations to embodiments of the present disclosure described above will make themselves apparent to those skilled in the art. All such variations, modifications, alterations and the like are intended to fall within the spirit and scope of the present disclosure, limited solely by the appended claims.

While several embodiments of the present disclosure have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

Any feature or element that is positively identified in this description may also be specifically excluded as a feature or element of an embodiment of the present as defined in the claims.

The domain of clinical decision support tools (CDSTs) has traditionally relied on generalized patient data, clinical guidelines, and basic imaging assessments to assist healthcare professionals in making informed decisions. However, these conventional approaches often may lack the granularity and specificity required to account for patient-specific anatomical and physiological variations. For example, while preoperative planning software has been used to generate 3D reconstructions of bones and fit implants to match patient anatomy, such software has historically failed to incorporate detailed assessments of bone quality, muscle quality, and other quantitative image-based measurements. This technical problem may hinder the ability of healthcare professionals to predict post-treatment outcomes, assess risks of complications, and optimize surgical planning based on individualized patient data. Furthermore, the lack of interpretability of highly granular image-based data may pose challenges for clinicians, as raw radiomic measurements often may fail to provide actionable insights without additional processing or contextualization.

In at least some embodiments disclosed herein may address these technical problems by introducing a novel system and method for utilizing radiomic-based measurements and other image-based data within a clinical decision support tool. This technical solution may integrate machine learning (ML) frameworks with standard medical imaging modalities (e.g., CT, MRI, X-ray) to extract, analyze, and interpret pixel- and voxel-level data from regions of interest, such as muscles, tendons, bones, and ligaments. By leveraging specialized algorithms, the system may perform quantitative analyses of image-based features, including shape, texture, and intensity metrics, and may combine these measurements with patient-specific data (e.g., demographics, comorbidities, clinical history) and traditional clinical outcomes. The system may employ advanced ML models, such as clustering algorithms and predictive regression models, to transform raw image-based data into clinically relevant classifications and predictions. These classifications may be aggregated into hierarchies that align with reference patient groups, enabling clinicians to visualize and interpret the data more effectively.

In at least some embodiments, the technical solutions described herein may further enhance usability by deploying pre-trained ML models within surgical planning software, allowing healthcare professionals to prospectively assign patients to clinically relevant classification systems based on their specific anatomical and radiomic profiles. This approach may not only improve the accuracy of clinical outcome predictions but also facilitate the identification of outlier measurements associated with poor functional performance or elevated complication risks. Additionally, the system may incorporate dimensionality reduction techniques and visualization tools, such as heat maps and adaptive tables, to simplify the presentation of granular data and improve interpretability. By integrating these capabilities, the system may transform complex healthcare data into actionable insights, enabling personalized treatment planning, risk assessment, and improved patient outcomes.

Clinical decision support tools (CDST) may be generally described without limitation as software designed to assist healthcare professionals in making informed decisions about patient care. These tools may use a variety of techniques, including artificial intelligence, to analyze patient data, clinical guidelines, and/or other relevant information to provide recommendations and/or alerts. The key features of CDSTs may include, but are not limited to:

- Data analysis: CDSTs may analyze large amounts of patient data, including electronic health records, lab results, and imaging studies, to identify patterns and trends that may be relevant to patient care.
- Clinical guideline integration: CDSTs may incorporate clinical guidelines and best practices to ensure that care decisions align with evidence-based standards.
- Decision support: CDSTs may provide specific recommendations and/or alerts to clinicians, such as suggesting diagnostic tests, recommending treatments, or flagging potential drug interactions.
- Personalized medicine: CDSTs may use patient-specific data to tailor recommendations and improve the accuracy of diagnoses and treatment plans.
- Workflow integration: CDSTs may be integrated into electronic health records and other healthcare workflows to streamline the decision-making process.

Machine learning techniques for healthcare applications may offer the potential to transform complex healthcare data into practical knowledge that can help surgeons better understand their patients and the complexities of their patient's conditions. By leveraging large quantities of high-quality clinical outcomes data, machine learning analyses can identify previously hidden correlations and relationships in datasets to create predictive models that can better inform individual patient treatment decisions.

In orthopedics, predictive models derived from high-quality outcomes and patient data may represent a patient-specific implementation of evidence-based decision-making tools, that may transform complex healthcare data into practical knowledge to support more-informed treatment decision making. While the commercial usage of machine learning may be new to orthopedics, its usage in research has increased in recent years. Many machine learning applications have been image-based analyses, but there is a growing interest to use machine learning techniques to predict clinical outcomes. Predictive outcomes models may assist the orthopedic surgeon to better identify which patients will benefit from elective procedures, such as arthroplasty, and also help better-align patient and surgeon expectations for clinical improvement by leveraging the experiences of previous patients with similar demographics, diagnoses, comorbidities, clinical history, and treatments. With more insight into the factors that predict patient-specific improvement, and with better alignment between predicted and actualized outcomes, patient satisfaction levels may likely increase through the use of such an evidenced-based predictive outcomes tool.

Embodiments of the present disclosure herein describe methods and systems for utilizing radiomic-based measurements (and other image-based measurements) for modeling predictive outcomes of arthroplasty surgical procedures. Arthroplasty may be used to repair or replace any joint in the body, including but not limited to the hips, knees, shoulders, elbows, and ankles, for example. However, to further illustrate these methods and systems, shoulder arthroplasty is used herein as an exemplary embodiment throughout this disclosure.

Radiomic measurements (and other image-based measurements) may include quantitative features extracted from medical images, such as for example, but not limited to computed tomography (CT) scans, Magnetic Resonance Imaging (MRI) scans, and/or Positron Emission Tomography (PET) scans. These features may describe the characteristics of tissues and lesions within the image, going beyond the simple visual assessment by a radiologist. Radiomic features may be broadly categorized into several types without limitation such as first-order statistics, texture features, and/or shape features. With regard to first-order statistics, these features may describe, for example, the distribution of pixel intensities within a region of interest (ROI), such as mean, standard deviation, skewness, and kurtosis. With regard to texture features, these features may capture the spatial distribution of pixel intensities, providing information about the texture and/or heterogeneity of the tissue. Common texture features may include but are not limited to gray-level co-occurrence matrix (GLCM), gray-level run-length matrix (GLRLM), and/or neighborhood gray-level difference (NGTDM) features. With regard to shape features, these features may describe the geometric properties of the region of interest (ROI), such as for example, volume, surface area, and/or sphericity.

In at least some embodiments, clinical decision support software may leverage standard of care medical imaging (CT, MRI, X-ray, Ultrasound, etc), in combination with surgical planning software, along with a machine learning framework to: 1) analyze a volume/region of interest from medical images (where the region of interest could be a portion of (or a full) muscle, tendon, bone (cortical or cancellous), or ligament, 2) perform numerous different quantitative image-based analyses, 3) compare these image-based measurements to a clinically relevant reference group of similar patients (to provide clinical context to the measurements—this comparison group may be derived or a learned group), specifically with the aid of a library of pre-trained image-based classification models and/or groups, for example a cluster model, that may be prospectively assigned to an individual patient in the software, and 4) use that image-based data (and/or aggregated data in the form of one or multiple groups/classes) to perform one or more clinically relevant predictions (i.e. regression or classification predictions) that may aid a physician and/or health care professional to diagnose, understand, and/or treat a musculoskeletal injury (degenerative or otherwise).

FIG. 1 is a block diagram of a surgical assistance system 10 for utilizing radiomic-based measurements (and other image-based measurements) within a clinical decision support software 80 in accordance with one or more embodiments of the present disclosure. The surgical assistance system 10 may include a medical computing device 15, a medical imaging system 35, a plurality of N electronic medical resources denoted ELECTRONIC RESOURCE 1 40A . . . ELECTRONIC RESOURCE N 40B, where N is an integer, and a computing device 77 of a user 20 all communicating 32 over a communication network 30. The computing device 77 of the user 20 may also be communicatively coupled 37 directly to the medical computing device 15.

In at least some embodiments, the user 20 that may interact with a graphic user interface (GUI) 75 on the computing device 77, may be a physician discussing an arthroplasty surgical procedure to be performed on a patient 25. In other embodiments, the computing device 77 may be placed in any suitable location such as an operating room where the joint arthroplasty surgical procedure may be performed.

The medical computing device 15 may include a processor 45, a non-transitory memory 60, a communication circuitry 70 for communicating 32 over the communication network 30, and/or I/O devices 65, such as a display for displaying the GUI 75 to the user 20, a keyboard 65A and a mouse 65B, for example.

In at least some embodiments, the medical computing device 15 may be configured to execute the clinical decision support software 80 that may include any or all of the different software modules listed below to perform the functions in the surgical assistance system 10 as described herein. The different software modules may include, but are not limited to, a patient-specific data collection module 46, a Medical Imaging Preprocessing Analyzer 48, a medical imaging machine learning model (MLM) module 50, a surgical planning software module 52, a machine learning model training module 54, and/or a GUI manager module 56 for controlling the GUI 75 on the user's computing device 77.

In at least some embodiments, the non-transitory memory 60 may be configured to store a clinical outcome database 62 with a plurality of clinical outcomes of different types of arthroplasty surgical procedures performed on a plurality of patients.

In at least some embodiments, the patient-specific data collection module 46 may query any of the plurality of electronic medical resources 40A and 40B over the communication network 30 to obtain medical data from the patient 25. The plurality of electronic medical resources 40A and 40B may be managed by the patient's health management organization HMO, a hospital that the patient 25 received medical treatment, a doctor that the patient 25 received medical treatment, for example.

In at least some embodiments, the Medical Imaging Preprocessing Analyzer 48 may analyze the data from medical images received from the medical imaging system 35. The medical imaging system 35 may generate an X-ray image, a computed tomography (CT) image, a magnetic resonance image, and/or a three-dimensional (3D) medical image, for example.

In at least some embodiments, the machine learning model (MLM) training module 54 may generate a training dataset for training any or all of the machine learning models used in the surgical assistance system 10.

The general overview of the image-based analysis in clinical decision support software 80 may be described hereinbelow.

In at least some embodiments, a machine learning analysis of the medical image may be performed by the Medical Imaging MLM 50 to identify clinically relevant data that may be useful for diagnosis and/or treatment decision making. These pixel/voxel level image-based analyses may be machine learning inferred characteristics (like embeddings) or more direct measurements, based on pre-defined formulas. As an example, radiomic image-based measurements may extract shape-based, first-order, and/or texture (second-order) measurements to define the characteristics associated with a patient's region and/or volume of interest (bone, muscle, tendon, ligament, or a portion or combination of each).

In at least some embodiments, the automated image-based measurements may be combined in the surgical planning software module 52 with patient data (demographics, comorbidities, diagnoses) and/or traditional clinical outcomes data (pre-operative patient reported outcomes, range of motion, pain scores, as well as post-operative results for each associated with numerous different treatments) and complication/revision data associated with numerous different treatments, along with data obtained from the planning software (joint relationship measurements, bone shape measurements of deformity, best-fit implants sizes/types which may match the anatomy of a given patient to best reconstruct the joint/match a bone shape, etc.) to better characterize the patients, with applications for diagnosis of pathology and defining potential options for treatment.

In at least some embodiments, these image-based measurements may be combined with pre-operative and/or post-operative clinical outcomes data, and/or surgical planning software data and may be used to train using the model training module 54, a machine learning (ML)-based predictive model to predict pre-operative and/or post-operative outcomes at various timepoints for different treatment options, as well as be used to predict clinical complications and risks of revision (for example, anatomic total shoulder arthroplasty vs. reverse total shoulder arthroplasty). However this process may not be limited to shoulder hip, knee, and/or ankle arthroplasty, but may be used for other treatment outcomes as well, such as trauma repair using open-reduction internal fixation plates, pins, screws, or nails and/or sports applications (rotator cuff, ligament, and/or bone repair, etc.)

In at least some embodiments, the clinical decision support software 80 may identify which of the image-based measurements may be clinically relevant. The feature importance data associated with the ML model inputs may be analyzed and rank-ordered so as to identify what features may be clinically relevant and meaningful within the medical images. The clinical decision support software 80 may compare these rank-ordered features relative to the same analysis from a reference patient group that may be used to identify outliers and unique morphological/anatomic parameters of interest to the physician and/or health care professional for a particular patient.

In at least some embodiments, the clinical decision support software 80 may prospectively deploy these ML models within the surgical planning software 52 in the clinical decision support software 80. Specifically, after the health care professional may upload medical images such as for example, a CT image into the planning software, the ML framework may create the 3D models on various regions of interest (bone, muscle, ligament, tendon, etc) and then may extract the radiomic data and combine it with other automated inputs and/or manual inputs (from the planning software) about a specific patient. The medical imaging MLM 50 may output to the surgeon (e.g., the user 20) within the Surgical Planning software 52 in order to aid in the diagnosis of a musculoskeletal injury (degenerative or otherwise), for example, and/or to aid them in decision-making related to which treatment option to select so as to optimize post-operative clinical outcomes.

One technical problem associated with image-based measurements which consider pixel/voxel-level granularity, is that these highly quantitative measurements may lack intuitive clinical interpretation such that the clinical meaning/relevance of these image-based measurements may not be readily apparent to the physician and/or health care professional. To solve these technical problems and aid the physician and/or health care professional to visualize and interpret the image-based measurements, the clinical decision support software 80 may conduct additional analyses and may be displayed within the software to reduce the dimensionality of the data and transform relevant image-based measurements into clinically relevant classification systems, which may be aggregated based on similarities to reference patient groups (these reference groups may be either learned or derived). For example, rather than displaying some or all of the raw or calculated image-based measurements associated with a given patient to the user in the surgical planning software 52, the surgical planning software 52 may provide the output of additional ML models and techniques which may be relevant to those measurements. To clarify, the software may provide one or more classification groups that may be representative of the patient's image measurements, where these pre-defined classifications may be derived from prior ML analyses, (e.g. a clustering algorithm) which may aggregate a series of image-based measurements (with or without corresponding patient data) and may output a clinically relevant classification system associated with an anatomic region/volume of interest. For example, there may be a library of image-based measurements which may include, a class 1/2/3/4 supraspinatus (rotator cuff muscle) describing the shape, size, or quality (and other radiomic measurements) of that muscle, and a class A/B/C/D/E proximal humeral bone which may describe the shape, size, or quality of that bone (and other radiomic measurements), and/or a class A/B/C/D scapular spine/acromion bone that may describe the shape, size, or quality of that bone, etc. These multiple radiomic measurements may be aggregated together into a single class or classification/type using an ML based clustering algorithm.

In at least some embodiments, the clinical decision support software 80 may aggregate numerous image-based measurements associated with a given patient that may improve the clinical interpretation of these pixel/voxel-level image-based measurements, as well as improve usability of the software. Moreover, the planning software may also have the capability to visualize in 2D or 3D the region of interest as a model, and to overlay a relevant image-based measurement alongside the original medical image (CT slide, 3D reconstruction, etc) so that the clinical meaning of the pixel/voxel-level measurements may be visualized and more easily interpreted by the physician and/or health care professional. If the physician and/or health care professional wants to be aware of a specific automated feature used by the ML models with high predictive importance, that data may be visualized on the display, if prompted.

In at least some embodiments, the clinical decision support software 80 may facilitate a development of a library of pre-defined classification systems derived from clinically relevant image-based measurements that may provide some additional usability advantages as well, since these bone/muscle groups/clusters may be prospectively identified. They may be numerically or visually displayed in the pre-operative planning software, mitigating the need to display multiple tables of radiomic measurements, which may have likely limited utility to the user.

In at least some embodiments, the advantage of ML based approaches to aggregate the data into clinically relevant classification systems that may be readily displayed in the software display 75 may be that it facilitates the physician and/or health care professional to more simply understand what may be clinically meaningful from this granular pixel/voxel-level image-based assessment. Additionally, by analyzing multiple, individual regions/volumes of interest (e.g., clinically relevant radiomics associated bone, tendon, and/or ligament), the interaction between these different anatomic structures/classification groups may be better understood, which may translate to an improved understanding of a patient's potential improvement capability and/or the patient's complication/revision risk, that may greatly simplify the meaning of the radiomic data.

In at least some embodiments, regarding the image-based analysis and clinical deployment of the clinical decision support software 80 that may utilize standard of care medical images from various hospitals and imaging manufacturers, using different image acquisition protocols, image pre-processing may be required to normalize and standardize the analysis, to be incorporated into the framework. Regardless of the imaging modality, this image processing may occur through various steps, most commonly: normalization, resampling, and discretization. Normalization may adjust the pixel gray level intensity values within an image-based on the mean and standard deviation of gray levels of that image. Resampling may adjust image resolution to standardize voxel size and ensure consistent spatial dimensions between images. Depending on the original image resolution, this process may up-sample (which may increase resolution but may introduce noise; interpolation may create new pixels in the gaps) or down-sample (which may decrease resolution and may reduce noise; interpolation may combine pixel values to reduce the number of pixels). Discretization may convert continuous intensity values into discrete values, simplifying image analysis and reducing storage requirements. This process may be performed using two methods: 1) a fixed bin width (which may distribute pixel intensities into bins of equal width, so the number of bins may vary across all images) or 2) a fixed bin count (which may distribute pixel intensities into a fixed number of bins, ensuring the number of bins may remain the same across all images). After these aforementioned image processing steps, image based measurements and/or radiomic features may be generated and extracted from the region/volume of interest. The region of interest may be derived using various methods, including manual segmentation, automated segmentation, and/or landmark/bounding boxes, etc.

In at least some embodiments, the at least one segmentation algorithm may include defined inputs and outputs, where the inputs may include PVG corrected medical images, image metadata that may preserve voxel spacing, orientation, and origin, configuration parameters for segmentation that may include anatomical priors, landmarks, or bounding boxes, and optional user edits that may refine automated results in semi-automated workflows. The outputs may include at least one ROI image map boundary that may provide a three dimensional, voxel aligned delineation of inclusion or exclusion for a specified region of interest, and an at least one ROI image map that may include the at least one ROI image map boundary and the PVG corrected image data that may be within the boundary for downstream preprocessing, feature extraction, classification, prediction, and visualization.

In at least some embodiments, at least one ROI image map boundary may include a three-dimensional, voxel aligned delineation that may encode inclusion or exclusion of image elements for a specified region of interest. At least one ROI image map boundary value may indicate membership in an anatomic structure or sub structure. This may define the region's boundary and interior in the same spatial frame as the PVG corrected medical images. The at least one ROI image map boundary may be generated by automated, semi-automated, or manual segmentation workflows. It may be stored as a binary or multi class 3D label map that may preserve voxel spacing, orientation, and origin metadata. It may be used by the at least one processor to constrain preprocessing, feature extraction, classification, prediction, and visualization to the labeled region.

In at least some embodiments, at least one ROI image map may include the at least one ROI image map boundary and the PVG corrected image data from the plurality of PVG corrected medical images that may be within the at least one ROI image map boundary. The at least one ROI image map may be provided, together with the associated metadata, to one or more medical image analysis machine learning models for subsequent analysis and display.

In at least some embodiments, with regard to arthroplasty procedures such as for example, shoulder arthroplasty, the machine learning techniques used in the clinical decision support software 80 may be further used to pre-operatively predict clinical outcomes at various post-operative timepoints after surgery for patients receiving total shoulder arthroplasty. For example, these predictions may be used to inform the surgeon of what a particular patient may expect to experience after anatomic total shoulder arthroplasty (aTSA) and/or reverse total shoulder arthroplasty (rTSA), for example. A list of model inputs may be obtained from the health care professional and/or automatically from the patient's electronic medical record through software integration by querying any of the electronic medical resources as previously described. While this disclosure focuses on aTSA and rTSA outcomes prediction, these models could also be applied to other shoulder arthroplasty applications, like hemiarthroplasty, fracture reconstruction, endoprostheses, resurfacing, and primary vs. revision arthroplasty outcomes predictions. These types of models may also be used in other orthopedic procedures, such as hip, knee, or ankle arthroplasty, spine or trauma procedures, as well as sports (muscle/tendon/ligament repair) procedures.

In at least some embodiments, regarding the inputs to these predictive models, the predictive outcomes for a given total shoulder arthroplasty patient may be further refined to provide recommendations for optimal clinical outcomes using different implant sizes, such as different sizes of humeral heads, humeral stems, glenospheres, glenoid or humeral augments, for example, implant types, such as aTSA, rTSA, hemiarthroplasty, resurfacing, short stem, stemless, fracture arthroplasty, endoprostheses, revision devices, for example, and/or surgical techniques, such as delto-pectoral, superior-lateral, subscapularis sparing, for example, in order to account for the patient specific diagnoses and bone/soft tissue morphological considerations.

In at least some embodiments, the machine learning predictive outcome algorithms in the clinical decision support software 80 as described herein may be used to pre-operatively predict a patient's post-operative clinical outcomes that may have numerous additional practical applications that may be valuable to the patient and surgeon. First, the ability to differentiate pre-operatively which patients may achieve clinical improvement after aTSA and rTSA relative to patient satisfaction anchor-based minimal clinically important difference (MCID) and substantial clinical benefit (SCB) thresholds for multiple different patient reported outcome measures (PROMs) and active range of motion (ROM) measurements may be useful to the orthopedic surgeon to objectively identify which patients are appropriate candidates for these elective procedures. It may also assist the orthopedic surgeon to decide between implant types for a particular patient. As a non-operative treatment may be best for some patients, this foreknowledge may represent a more efficient resource allocation for the patient, surgeon, hospital, and/or payer.

In this disclosure, the terms "outcome metric" and "outcome measure" may be used interchangeably herein. The terms "machine learning model", "machine learning module", "machine learning predictive outcome algorithms", "predictive outcome algorithms" and/or "predictive outcome model" may be used interchangeably herein.

In at least some embodiments, a patient-specific prediction of clinical improvement at multiple post-surgical timepoints may be helpful to align patient and surgeon expectations on what is achievable after this elective procedure. Given the association between pre-operative expectations and post-operative satisfaction, better surgeon-patient alignment on both the magnitude and rate of clinical improvement may result in greater levels of patient satisfaction. Furthermore, an improved understanding of the amount of clinical improvement that can be expected at different post-surgical timepoints for a given patient may aid the surgeon in establishing protocols for rehabilitation. This may also help both the surgeon and patient weigh these gains versus the procedure-specific risks associated with aTSA and rTSA, such as: instability, aseptic loosening, and infection.

In at least some embodiments, the predictive models used by the clinical decision support software 80 may provide a better understanding of the factors influencing outcomes, which may assist the orthopedic surgeon to personalize care for each patient in terms of patient-specific requirements for pain relief, function, and mobility, as well as to help the patient better understand how well the arthroplasty surgical procedure may meet their needs based upon that patients unique characteristics that are input to and accounted for in the predictive model output.

In at least some embodiments, there may be numerous clinical applications for the clinical decision support software 80 using the automated image-based clinical decision support tool (e.g., the medical imaging pre-processing analyzer 48 and/or the medical imaging machine learning model (MLM) 50, when incorporated into a CT based pre-operative planning software (e.g., the surgical planning software 52) as described in the four clinical applications hereinbelow.

In at least some embodiments, the medical imaging machine learning model (MLM) module 50 may include defined inputs and outputs, where the inputs may include PVG corrected medical images of the joint, at least one ROI image map boundary, an at least one ROI image map that may include the at least one ROI image map boundary and the PVG corrected image data within the boundary, segmentation outputs identifying at least one region of interest such as bone, connective tissue, or muscle, patient specific data including demographics, comorbidities, diagnosis, preoperative range of motion and pain metrics, surgical planning data and arthroplasty parameters including implant type, size, and planned positions, reference cohort and classification library data for outlier detection and class assignment, and image preprocessing metadata and radiomics configuration including normalization, resampling, and discretization settings.

In at least some embodiments, the outputs may include at least one image based measurement and/or radiomic feature extracted from the region of interest, at least one implant complication risk assessment that may predict probabilities for instability, aseptic loosening, fracture, infection, or revision within defined windows, prospective class or cluster assignments based on image-based measurements, predicted postoperative joint performance metrics at multiple timepoints that may include range of motion values and pain metrics when provided with the reconstruction plan and patient data, visualization artifacts that may improve interpretability such as heat maps, class activation maps, and color coded indicators, alerts that may identify outlier image-based measurements linked to decreased function or increased complication risk, and at least one 3D representation and overlay that may integrate measurements and risk assessments for display in the GUI.

In at least some embodiments, in a first Clinical Application for improving the accuracy of aTSA and rTSA Clinical Outcome Predictions, the addition of automated image-based measurements may provide additional objective data that may be used to improve the accuracy of clinical outcome predictions. With improved accuracy of outcomes associated with multiple different treatments, the clinical decision support software 80 may be used to improve surgeon and patient understanding of what may be possible with different treatments such as for example, identifying patients with higher/lower potential for clinical improvement for a given treatment. Post-operative patient satisfaction may increase if actual results may be more closely aligned with pre-operative patient expectations related to a given treatment.

In at least some embodiments, to demonstrate the capability of these image-based measurements to improve clinical outcome predictions, a study was performed on preoperative CT images and clinical data from 4,009 primary shoulder arthroplasty patients (2099 female, 1910 male; age=69.6±8.4, range: 23-97 years; 1011 aTSA and 2998 rTSA) enrolled in a multi-center, IRB-approved clinical outcome study of a single platform shoulder prosthesis (See for example, Equinoxe; Exactech, Inc., Gainesville, FL). Specifically, 3D masks of the deltoid muscle (2597 patients) and scapular bone (3,358 patients) may be auto-segmented from pre-operative CT images using a ML-based framework. Using this framework, numerous radiomic measures of the deltoid muscle and/or scapular bone may be extracted. These radiomic measurements may be used to quantify deltoid muscle and scapular bone characteristics, including, for example: shape-based features, first order Hounsfield (HU) intensity-based features, and/or second order "texture" features. A sensitivity study may be performed to demonstrate that these radiomic measures may be stable and robust across the range of CT image acquisition parameters and across the image processing parameters that may be deployed.

FIG. 15 is a table showing Definitions of PyRadiomics Radiomic Feature Measurements in accordance with one or more embodiments of the present disclosure. In at least some embodiments, a description of these radiomic parameters may be shown in the Table of FIG. 15. The parameters used in the sensitivity study are presented in the Table of FIG. 16.

FIG. 16 is a table showing CT image processing parameters used for the 7 different methods for the Deltoid muscle and Scapular bone sensitivity study in accordance with one or more embodiments of the present disclosure.

FIG. 17 is a table showing PyRadiomics radiomic features deemed robust, stable, and unique/non-redundant after sensitivity analysis and correlation study for the Deltoid muscle in accordance with one or more embodiments of the present disclosure.

FIG. 18 is a table showing PyRadiomics radiomic features deemed robust, stable, and unique/non-redundant after sensitivity analysis and correlation study for the Scapular Bone in accordance with one or more embodiments of the present disclosure.

In at least some embodiments, machine learning models may be developed to predict pre-operative pain, motion, and function, as well as clinical outcomes after aTSA and rTSA. Predictive models were trained using 3 different sets of inputs. The study control may be trained using inputs for patient demographics and comorbidities, along with data from pre-operative planning software (implant type/size and/or joint measurements). A second model may be trained using the control inputs in combination with deltoid muscle radiomic data. A third model may be trained using the control inputs in combination with scapular bone radiomic data. Specifically, XGBoost may be used to construct ML regression models that may predict the ASES, Constant, Shoulder Function, VAS Pain, and the Shoulder Arthroplasty Smart (SAS) scores, as well as active abduction, forward elevation, external rotation with the arm at the side, and the internal rotation (IR) score. Regression models may predict each of these clinical measures preoperatively (except ASES and Constant) and post-operatively at 3-6 months, 6-9 months, 1-year (9-18 months), 2-3 years (18-36 months), and 3-5 years (36-60 months) outcomes after aTSA and rTSA. Additionally, classification models may predict 2-3 year clinical improvement relative to the minimal clinically important difference (MCID) and substantial clinical benefit for each outcome measure.

In at least some embodiments, the deltoid model may utilize data from 2597 patients (1502 F, 1095 M) with 4970 post-operative visits (610 aTSA patients (311 F, 299 M), average latest follow-up=23.6±19.2 months; 1987 rTSA patients (1191 F, 796 M), average latest follow-up=21.1±18.0 months), that may be distributed across timepoints as follows: pre-operatively (aTSA=610 and rTSA=1987), 3-6 months (aTSA=284 and rTSA=1014 visits), 6-9 months (aTSA=105 and rTSA=534 visits), 1 year (aTSA=351 and rTSA=1075 visits), 2-3 years (aTSA=281 and rTSA=766 visits), and 3-5 years (aTSA=160 and rTSA=400 visits). Similarly, the scapular bone model may utilize data from 3,358 patients (1740 F, 1618 M) with 6,972 post-operative visits (877 primary aTSA patients (368 F, 509 M), average latest follow-up=25.8±19.2 months; 2481 primary rTSA patients (1372 F, 1109 M), average latest follow-up=23.5±18.2 months), that may be distributed across time-points as follows: pre-operatively (aTSA=877 and rTSA=2481), 3-6 months (aTSA=398 and rTSA=1187 visits), 6-9 months (aTSA=156 and rTSA=664 visits), 1 year (aTSA=530 and rTSA=1485 visits), 2-3 years (aTSA=462 and rTSA=1174 visits), and 3-5 years (aTSA=274 and rTSA=642 visits). This data may be randomly split into 80%: 20% mutually exclusive datasets to build and test the predictive models at each timepoint; the process may be repeated using k-fold cross validations (n=5) to reduce overfitting. The predictive performance of each regression model may be quantified by the Mean Absolute Error (MAE) and the predictive performance of each 2-3 year MCID and SCB classification model was quantified using accuracy, precision, recall, and the area under the receiver operating curve (AUROC).

FIG. 19 is a table showing a comparison of the Mean Absolute Error (MAE) Associated with 2 Different Machine Learning Models (Deltoid Muscle Image data vs. No-image data) to Predict Clinical Outcomes, Pre-operatively, 3 months, 6 months, 1 yr, 2-3 yrs, and 3-5 yrs after aTSA and rTSA in accordance with one or more embodiments of the present disclosure.

FIG. 20 is a table showing Classification Predictions Performance Associated with 2 Different Machine Learning Models (Deltoid Muscle Image data vs. No-image data) to Predict aTSA and rTSA clinical improvement at 2-3 years follow-up greater than the MCID threshold for multiple different outcome measures in accordance with one or more embodiments of the present disclosure.

FIG. 21 is a table showing Classification Predictions Performance Associated with 2 Different Machine Learning Models (Deltoid Muscle Image data vs. No-image data) to Predict aTSA and rTSA clinical improvement at 2-3 years follow-up greater than the SCB threshold for multiple different outcome measures in accordance with one or more embodiments of the present disclosure.

In at least some embodiments, the addition of deltoid muscle radiomic data to the XGBoost ML models may improve the accuracy of 110 of 156 (70.5%) regression predictions of clinical outcomes before and after aTSA and rTSA as shown in the Table of FIG. 19. For all patients, the largest improvements in predictive accuracy were observed for abduction (preoperative=10.8% improvement and 3-5 years=9.3% improvement). Some marginal differences were observed with the other outcome measures. rTSA predictions (37 of 52, 71.2%) were improved more frequently than aTSA predictions (35 of 52, 67.3%) by the addition of the deltoid muscle radiomic data; however, the largest improvements in prediction accuracy (Constant at 3-5 years=16.3% improvement) and the largest reduction in prediction accuracy (IR score at 6 months=15.7% decline) were observed with aTSA patients. The addition of the deltoid muscle radiomic data achieved similar MCID (see the Table in FIG. 20) and SCB (see the Table in FIG. 21) classification prediction performance.

FIG. 22 is a table showing a comparison of the Mean Absolute Error (MAE) Associated with 2 Different Machine Learning Models (Scapular Bone Image data vs. No-image data) to Predict Clinical Outcomes, Pre-operatively, 3 months, 6 months, 1 yr, 2-3 yrs, and 3-5 yrs after aTSA and rTSA in accordance with one or more embodiments of the present disclosure.

FIG. 23 is a table showing Classification Predictions Performance Associated with 2 Different Machine Learning Models (Scapular Bone Image data vs. No-image data) to Predict aTSA and rTSA clinical improvement at 2-3 years follow-up greater than the MCID threshold for multiple different outcome measures in accordance with one or more embodiments of the present disclosure.

FIG. 24 is a table showing Classification Predictions Performance Associated with 2 Different Machine Learning Models (Scapular Bone Image model vs. No radiomic image data) to Predict aTSA and rTSA clinical improvement at 2-3 years follow-up greater than the SCB threshold for multiple different outcome measures in accordance with one or more embodiments of the present disclosure.

In at least some embodiments, the addition of scapular bone radiomic data to the XGBoost ML models may improve the accuracy of 105 of 156 (67.3%) regression predictions of clinical outcomes before and after aTSA and rTSA. (See the Table of FIG. 22) For all patients, the largest improvements in predictive accuracy may be observed for abduction (6 month=9.7% improvement and 1 year=10.2% improvement), forward elevation (preoperative=8.6% improvement, 1 year=9.4% improvement, 3-5 year=11.1% improvement), and Constant (3-5 year=13.7% improvement). Some marginal differences may be observed with the other outcome measures. rTSA predictions (36 of 52, 69.2%) may be improved more frequently than aTSA predictions (32 of 52, 61.5%) by the addition of the scapular bone radiomic data; however, the largest improvements in prediction accuracy may be observed for aTSA patients, for each of forward elevation (1 year=20.0% improvement), abduction (6 months=19.4% improvement), and SAS score (1 year=18.3% improvement). The addition of the scapular bone radiomic data achieved similar MCID (See the Table of FIG. 23) and SCB (See the Table of FIG. 24) classification prediction performance.

In some embodiments in a second clinical application, the clinical decision support software 80 may be configured to identify patients with Outlier Image-based Measurements and to trigger physician alerts when detecting these Outlier Measurements are Associated with Poor Functional Performance. The clinical decision support software 80 may identify patients with outlier image-based measurements by: identifying radiomic measurements which were most clinically relevant and meaningful, identifying typical ranges associated with those measurements, and then comparing the ranges to clinically relevant functional thresholds to determine if an outlier image-based measurement is associated with a poor functional performance.

In at least some embodiments, the clinical decision support software 80 may utilize the clinical data and ML models as described above, specifically for the ML models trained with radiomic data. The relative importance of each input may be quantified to predict each outcome measure preoperatively and may be quantified to predict each outcome measure 2-3 years post-operatively by using an F-score. The F-score feature importance data may be averaged across the outcome measures and rank ordered to identify the consensus top deltoid muscle radiomic measures and the scapular bone radiomic measurements that may be most predictive of pre-operative pain, motion, and/or function, as well as clinical outcomes after aTSA and/or rTSA. These most clinically relevant radiomic measures may then be compared between patients for various functional differences.

FIG. 25 is a table showing Comparison of the Top 20 Preoperative Model Inputs (by F-Score Ranking) Used to Predict Pre-operative Clinical Outcomes Using the Deltoid Muscle Model in accordance with one or more embodiments of the present disclosure.

FIG. 26 is a table showing Comparison of the Top 20 Pre-operative Model Inputs (by F-Score Ranking) Used to Predict 2-3 year Clinical Outcomes after aTSA and rTSA Using the Deltoid Muscle Model in accordance with one or more embodiments of the present disclosure.

FIG. 27 is a table showing Comparison of Average Deltoid Muscle Radiomic Measurements Associated with Primary aTSA and rTSA Patients, Stratified by Gender and Age at the Time of Surgery in accordance with one or more embodiments of the present disclosure.

In at least some embodiments, the F-score feature importance data for the deltoid muscle model may be rank-ordered to identify the most predictive features driving the pre-operative predictions (see the Table of FIG. 25), as well as the 2-3 year predictions (see the Table of FIG. 26). Deltoid muscle data may be commonly used by the ML models, with 13 of the top 20 features driving the pre-operative model (see the Table of FIG. 25) and 6 of the top 20 features driving the 2-3 year model (see the Table of FIG. 26). Across these timepoints, the consensus top 8 most predictive deltoid muscle features may be: normalized volume, flatness, elongation, sphericity, max 2D diameter column, max 2D diameter row, fat percentage, and 10th percentile HU. The Table of FIG. 27 may compare the variability of these 8 features across the aTSA and rTSA patients, stratified by age and gender, and may demonstrate that deltoid elongation, flatness, fat percentage, max 2D diameter row/column measurements may all differ significantly by gender across the range of patient age at the time of surgery.

FIG. 28 is a table showing Comparison of the Top 20 Preoperative Model Inputs (by F-Score Ranking) Used to Predict Pre-operative Clinical Outcomes Using the Scapular Bone Model in accordance with one or more embodiments of the present disclosure.

FIG. 29 is a table showing a comparison of the Top 20 Pre-operative Model Inputs (by F-Score Ranking) Used to Predict 2-3-year Clinical Outcomes after aTSA and rTSA Using the Scapular Bone Model in accordance with one or more embodiments of the present disclosure.

FIG. 30 is a table showing a comparison of Average Scapular Bone Radiomic Measurements Associated with Primary aTSA and rTSA Patients, Stratified by Gender and Age at the Time of Surgery in accordance with one or more embodiments of the present disclosure.

The F-score feature importance data for the scapular bone model were rank-ordered to identify the most predictive features driving the pre-operative predictions (see the Table of FIG. 28), as well as the 2-3 year predictions (see the Table of FIG. 29). Scapular bone data was commonly used by the ML models, with 13 of the top 20 features driving the preoperative model (see the Table of FIG. 28) and 7 of the top 20 features driving the 2-3 year model (see the Table of FIG. 29). Across these timepoints, the consensus top 8 most predictive scapular bone features are: flatness, elongation, sphericity, max 2D diameter column, max 2D diameter slice, least axis length, 10th percentile HU, and max 2D diameter row. The Table of FIG. 30 may compare the variability of these 8 features across the aTSA and rTSA patient cohorts, stratified by age and gender, and demonstrates these scapular bone measurements all differ significantly by gender across the range of patient age at the time of surgery, with only a few exceptions: elongation and sphericity for patients <60 years of age.

FIG. 31 is a table showing a comparison of Average Deltoid Muscle Radiomic Measurements Associated with aTSA/rTSA Patients with and without High Preoperative Overhead Motion (defined as ≥160° in abduction and/or forward elevation), stratified by the prosthesis type that they would later receive in accordance with one or more embodiments of the present disclosure.

In at least some embodiments, to assess the clinical relevance of the deltoid image measurements and identify which radiomic measures may be associated with poor functional performance, primary aTSA and rTSA patients with high-levels of pre-operative overhead motion (defined as ≥160° in abduction and/or forward elevation) may be compared to patients with lower-levels of pre-operative overhead motion. As described in the table of FIG. 31, prior to surgery aTSA patients with high overhead motion may have comparatively larger, rounder, and thicker deltoids as demonstrated by the significantly larger values of deltoid normalized volume ($p=0.047$), elongation ($p=0.013$), flatness ($p=0.017$), least axis length ($p=0.014$), mesh volume ($p=0.023$), and a significantly lower deltoid surface to volume ratio ($p=0.049$) as compared to aTSA patients with lower overhead motion. Similar findings may be observed for rTSA patients, as described in the Table of FIG. 31, where rTSA patients with high overhead motion pre-operatively, may have comparatively larger, rounder, and thicker deltoids as demonstrated by the significantly larger values of deltoid normalized volume ($p=0.001$), elongation ($p<0.001$), mesh volume ($p<0.001$), sphericity ($<0.001$) and a significantly lower deltoid surface to volume ratio ($p<0.001$) as compared to rTSA patients with lower overhead motion.

Figure 2:
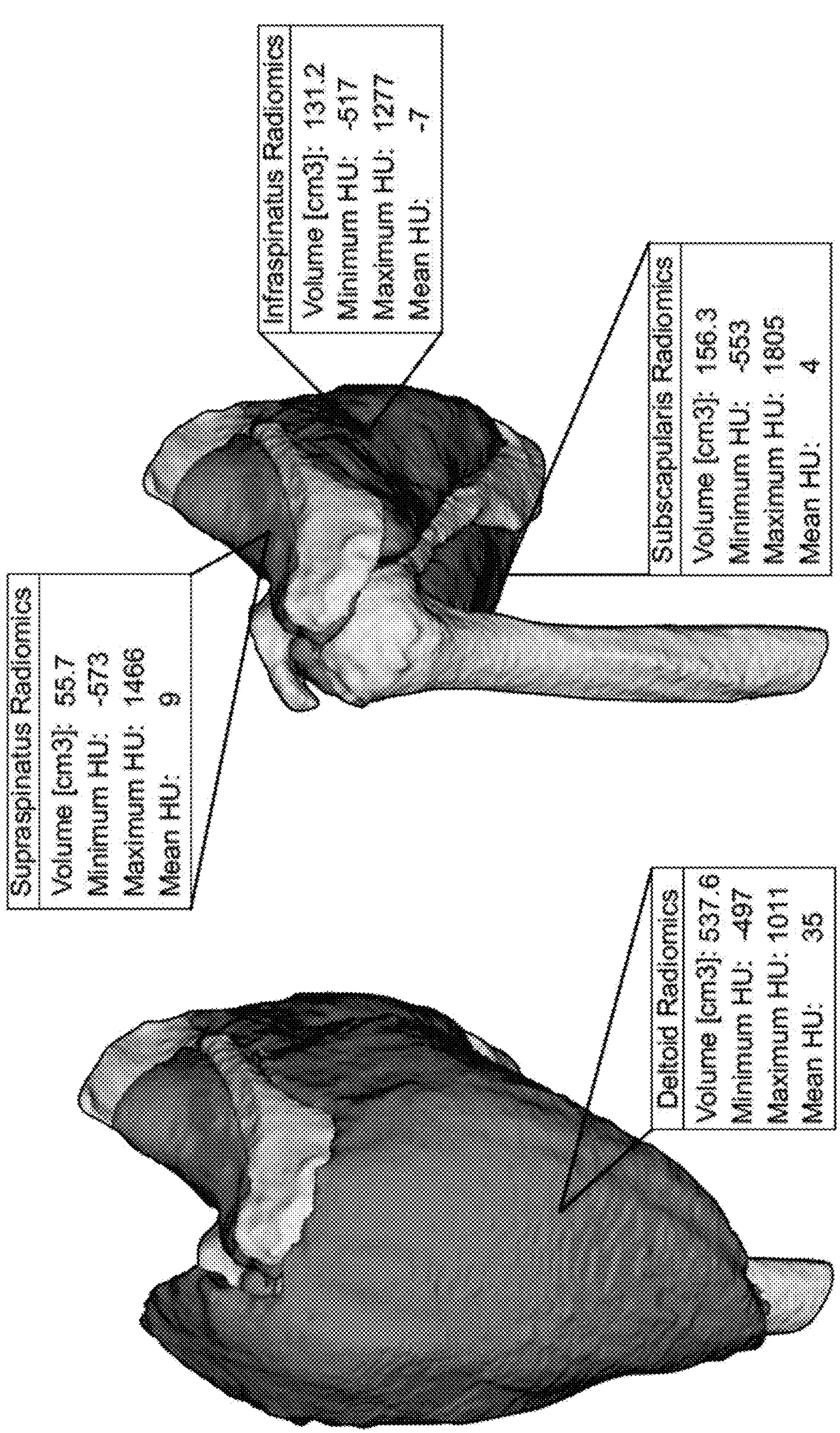

FIG. 2 illustrates 3D reconstructions of the scapula, proximal humerus, deltoid muscle, and rotator cuff muscles (left), with select radiomic measurements of the deltoid are extracted and presented (left), and also with the deltoid removed (right) to show the supraspinatus, infraspinatus, and subscapularis rotator cuff muscles (right), in this example (right) select radiomic measures of the supraspinatus, infraspinatus, and subscapularis rotator cuff muscles are extracted and presented in accordance with one or more embodiments of the present disclosure. FIG. 2 illustrates the individual muscles as referenced in this disclosure.

Figure 3:
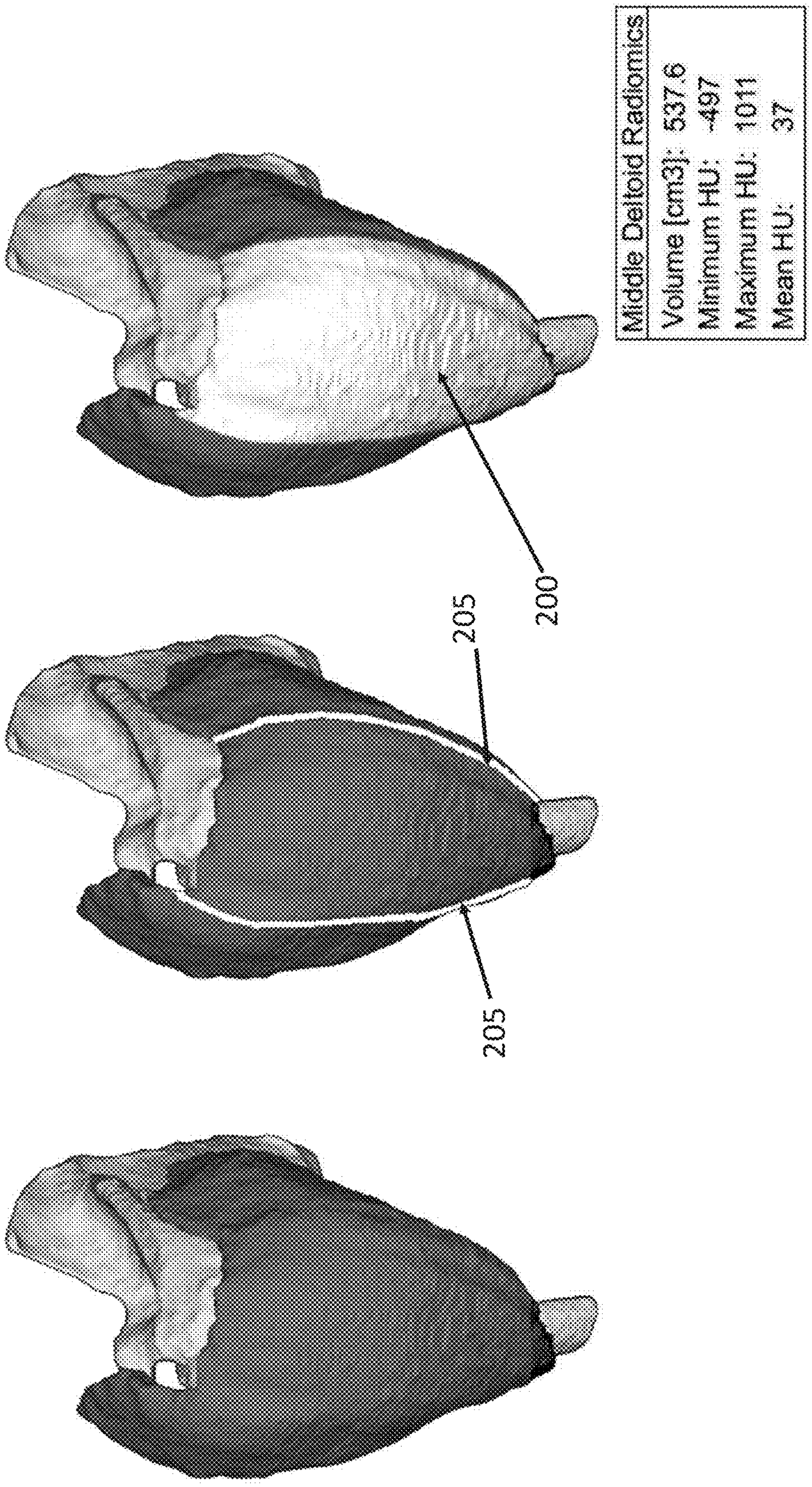

FIG. 3 illustrates 3D reconstructions of the scapula, proximal humerus, and deltoid muscle (left), with segmentation of the 3D muscle volume into anatomically relevant sub-volumes of the deltoid (anterior, middle, and posterior deltoid) for localized radiomic analysis (right), select radiomic measures of the middle deltoid are extracted and presented in accordance with one or more embodiments of the present disclosure. Particularly, FIG. 3 illustrates the deltoid muscle as a region of interest (ROI) 200 and a ROI image map boundary 205 (e.g., ROI outline) that are the output of the at least one segmentation algorithm as described hereinabove. The ROI image map boundary 205 and the PVG corrected image data of the region of interest 200 of the deltoid muscle may be inputted into the at least one medical image analysis machine learning model that is trained to output at least one image based measurement in the region of interest 200 and at least one implant complication risk assessment for the implantation of the at least one implant into the joint.

In at least some embodiments, while one example may be demonstrated here, it should be understood that similar analyses between image data and clinical performance may be performed for any number of good/poor performing cohorts for any clinical outcome measure. For example as described in FIG. 2, radiomics associated with the deltoid and rotator cuff muscles may be analyzed and compared between patients with and without full range of motion, and in doing so may identify the radiomic parameters that may be associated with patients who experienced more range of motion as compared to patients with less range of motion, and may then use that knowledge prospectively as a risk-profiler for new patients to alert the physician and/or health care professional if a particular patient may be at risk for less range of motion after a given treatment. This comparison of radiomic parameters may be performed on the full muscle volume or may be performed on a segment of the muscle, if that may be more clinically appropriate, for example the middle deltoid sub-volume as depicted in FIG. 3. These analyses may also be performed on other soft-tissue, like tendons or ligaments.

In some embodiments in a third clinical application, the clinical decision support software 80 may be configured to identify Patients with Outlier Image-based Measurements and to alert the physician if these outlier measurements may be associated with a complication.

FIG. 32 is a table showing a comparison of Average Deltoid Muscle Radiomic Measurements Associated with Primary rTSA Patients with and without Adverse Event Reports of Instability in accordance with one or more embodiments of the present disclosure.

In at least some embodiments, similarly, to the process described above, the clinical decision support software 80 may compare outlier image measurements between patients with and without complications and may determine if an outlier image-based measurement may be associated with a particular treatment complication. To assess the clinical relevance of the deltoid muscle measurements to complications, as an example, the deltoid muscle radiomic measurements may be associated with rTSA patients who experienced post-operative instability as compared to deltoid muscle radiomic measurements for rTSA patients without a report of instability. As described in the table of FIG. 32, rTSA patients with instability may have comparatively larger, longer, wider, and thicker deltoids preoperatively as demonstrated by the significantly larger values of deltoid normalized volume ($p=0.016$), least axis length ($p=0.0024$), max 2D diameter column ($p=0.009$), max 2D diameter row ($p=0.001$) and a significantly lower deltoid surface to volume ratio ($p=0.001$) as compared to rTSA patients without instability.

FIG. 33 is a table showing a comparison of Average Scapula Bone Radiomic Measurements Associated with Primary rTSA Patients with and without Adverse Event Reports of Scapula Fractures in accordance with one or more embodiments of the present disclosure.

To assess the clinical relevance of the scapular bone measurements to complications, as an example, scapular bone radiomic measurements may be associated with primary rTSA patients who experienced scapular fractures that may be compared to scapular bone radiomic measurements associated with rTSA patients without scapular fractures. As described in the table of FIG. 33, rTSA patients with scapular fractures may have comparatively smaller, thinner, shorter, and less-spherical scapula preoperatively as demonstrated by the significantly smaller values of scapula least axis length ($p=0.004$), minor axis length ($p=0.012$), max 2D diameter row ($p=0.016$), max 2D diameter slice ($p=0.009$), mesh volume ($p=0.001$), sphericity ($p=0.049$), and a significantly larger scapula surface to volume ratio ($p<0.001$) as compared to rTSA patients without scapular fractures. Some differences may also be observed with texture measurements as well, where rTSA patients with scapular fractures may have significantly higher values of NGTDM Strength ($p<0.001$) as compared to rTSA patients without scapular fractures.

Figure 4:
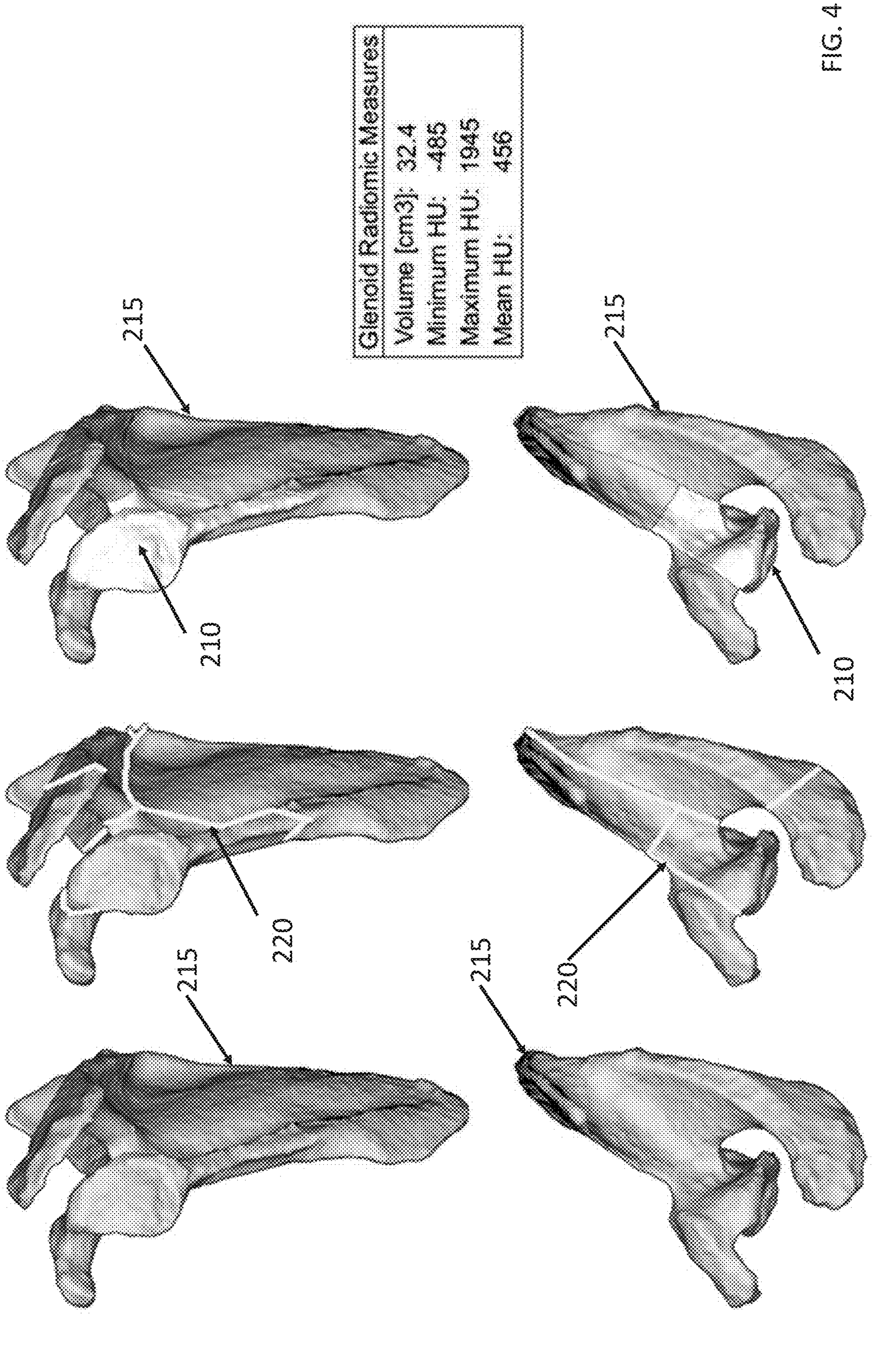

FIG. 4 illustrates multiple views of 3D reconstructions of a scapular bone (left), with segmentation of the 3D volume into anatomically relevant sub-volumes of scapular bone segments for localized radiomic analysis (middle), in this example (right), select radiomic measures of the glenoid vault are extracted and presented in accordance with one or more embodiments of the present disclosure. Particularly, FIG. 4 illustrates the scapula 215 having a region of interest (ROI) 210 and a ROI image map boundary 215 (e.g., ROI outline) that are the output of the at least one segmentation algorithm as described hereinabove. The ROI image map boundary 215 and the PVG corrected image data of the region of interest 210 of the scapula may be inputted into the at least one medical image analysis machine learning model that is trained to output at least one image based measurement in the region of interest 210 and at least one implant complication risk assessment for the implantation of the at least one implant into the joint.

Figure 5:
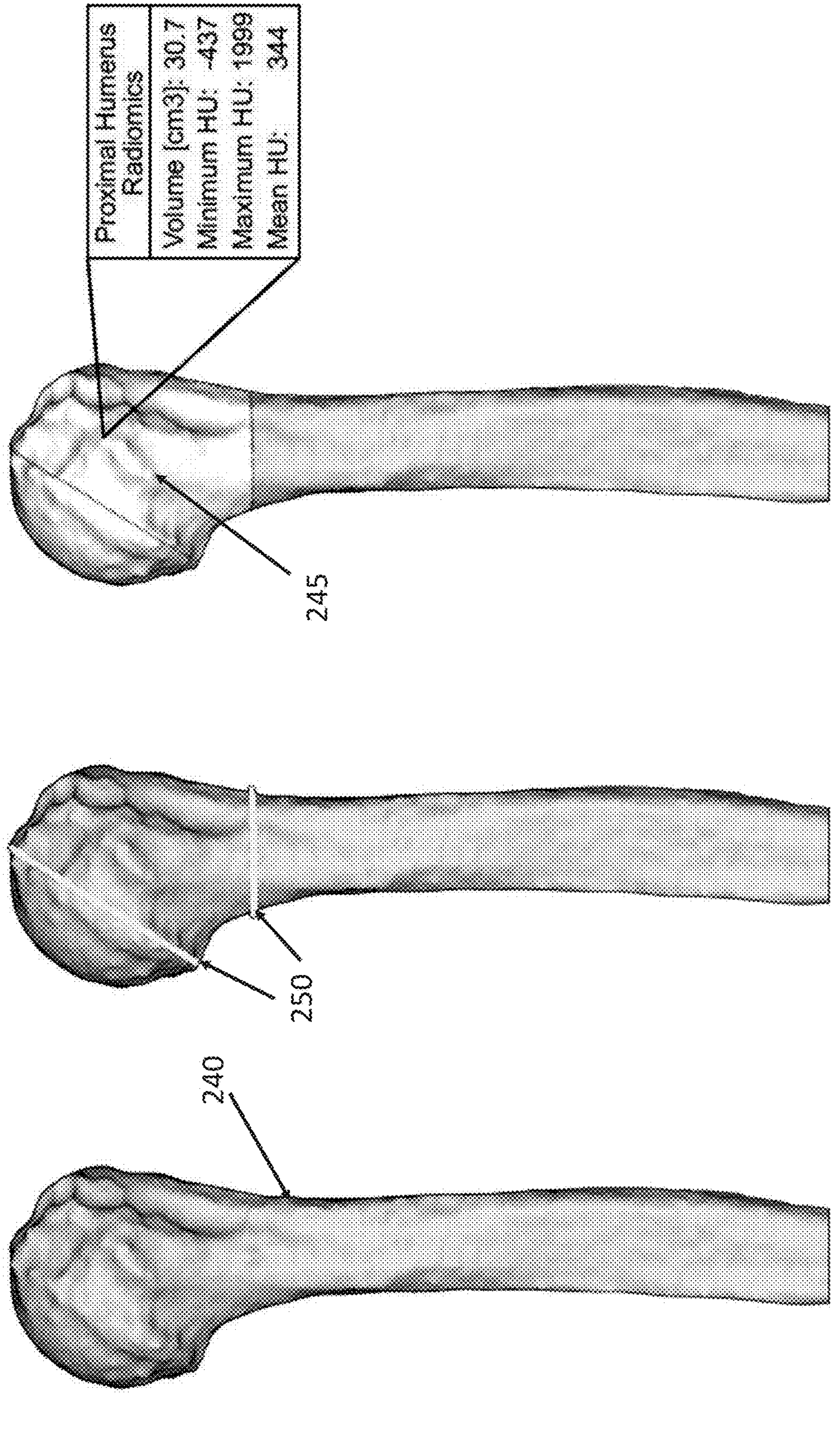

FIG. 5 illustrates multiple views of 3D reconstructions of the proximal humerus (left), with segmentation of the 3D volume into anatomically relevant sub-volumes of the proximal humeral bone segments for localized radiomic analysis (middle), in this example (right), select radiomic measures of the proximal humeral metaphysis and humeral head are extracted and presented in accordance with one or more embodiments of the present disclosure. Particularly, FIG. 5 illustrates the proximal humerus 240 having a region of interest (ROI) 245 of a bone segment of the proximal humerus 240 and a ROI image map boundary 250 (e.g., ROI outline) that are the output of the at least one segmentation algorithm as described hereinabove. The ROI image map boundary 250 and the PVG corrected image data of the region of interest 245 of the proximal humerus 240 may be inputted into the at least one medical image analysis machine learning model that is trained to output at least one image based measurement in the region of interest 245 and at least one implant complication risk assessment for the implantation of the at least one implant into the joint.

In at least some embodiments, that while two examples may be demonstrated here, it should be understood that similar analyses between image data and complications may be performed for any number of different cohorts with and without complications of various types (intra-operative, post-operative, revision, etc.) For example, as described in FIG. 4, radiomics associated with the glenoid vault may be analyzed and compared between patients with and without aseptic aTSA/rTSA glenoid loosening, and in doing so may identify the radiomic parameters that may be associated with patients that experienced this complication, and then may use that knowledge prospectively as a risk-profiler for new patients to alert the physician and/or health care professional if a particular patient may be at risk for glenoid implant loosening because they may have a glenoid vault with low bone quality and/or a radiomic profile similar to other patients that may have previously experienced the same failure mode.

In at least some embodiments, as another example described in FIG. 5, radiomics associated with the proximal humerus metaphysis may be analyzed and may be compared between patients with and without humeral stem loosening, and in doing so may identify the radiomic parameters that may be associated with patients that experienced this complication, and then use that knowledge prospectively as a risk-profiler for new patients to alert the physician and/or health care professional if a particular patient may be at risk for humeral implant loosening because they may have a proximal humerus with low bone quality and/or with a radiomic profile similar to other patients that may have previously experienced the same failure mode. Additionally, the examples provided for this risk profiler applications may be based on radiomic image-based measurements, but this image-based data may be based on other measurements, like embeddings or class activation maps.

In some embodiments in a fourth clinical application, the clinical decision support software 80 may be configured to create a library of clinically relevant classification systems derived using predictive image-based automated measurements, which may be prospectively matched to an individual patient in the Clinical Decision Support Tools (CDSTs). One barrier to the adoption of ML based CDSTs may be the need for clinicians to understand the basis of the predictions. The clinical interpretability of CDSTs utilizing image-based measurements may vary with technique. For example, when considering model inputs, shape based radiomic inputs may be more intuitive than first-order and second-order/texture inputs, since these pixel and/or voxel level measurements may be imperceptible to the naked eye. However, even if an individual image-based measurement may be intuitive to the health care professional user of the software, because there may be potentially so many different measurements that may be used, it may not be practical to communicate all of these image-based measurements to the user. One potentially user-friendly method to leverage numerous image-based measurements may aggregate these most clinically relevant image-based data into classification groups by utilizing one or more ML based methods, such as principal component analysis or clustering. As an illustrative example, clustering may be an unsupervised ML based approach to classify complex datasets into distinct groups having unique characteristics. This dimensionality reduction technique may improve the interpretation of image-based analysis by consolidating numerous pixel and/or voxel level measurements into macro-patterns that may be morphologically distinct and may be more readily visualized. Moreover, these types of ML based methods may be used singularly or may be combined to aggregate the most-predictive image-based measurements which may naturally occur in a reference population to create clinically relevant classification systems associated with different anatomical structures or performance characteristics.

In at least some embodiments, the clinical utility and/or specificity of the classification systems may be objectively assessed to select the methodology by which classification systems are derived, including choice of ML technique and/or associated model parameters. Model parameters may include the number of groups and/or classes and the number of image-based measurements and/or patient parameters based on which the classes may be formed. Objective assessment may include internal validation metrics which may assess the compactness and separation of clusters and/or "groups" formed by the ML algorithms based on the number of clusters. Additionally, clinical utility and/or relevance of the classification systems may be objectively examined in the context of clinical outcomes, patient satisfaction, and/or complications to determine if prospective assignment of certain classes may be associated with higher/lower outcomes, higher/lower patient satisfaction, and/or higher/lower risk of a complication compared to other singular classes and/or the rest of the population to aid in both outlier detection and/or interpretability of the associated image-based measurements.

In at least some embodiments, as a non-limiting example, perturbations of centroid-based k-means clustering were performed for the scapular bone and deltoid muscle by varying the number of clusters and/or the number of image-based parameters utilized as predictors on which the algorithms formed clusters. Both internal validation metrics and/or clinical-based metrics quantifying separation of clusters were plotted against the number of clusters for various combinations of image-based predictors. Predictors were rank ordered from the feature importance analysis and clustering was performed using the top 4, 8, 12, and all radiomic measurements as predictors to form clusters for the scapula and deltoid. The scapular bone clustering may also include native morphological measurements that were used as features in the predictive ML models. Internal validation metrics may be included within cluster sum of squares (WCSS) and the Silhouette score. Clinical metrics may include the percentage of pairwise significant differences between clusters for nine clinical outcome measures preoperatively and for 2-year minimum post-operative and pre-to-postoperative improvement. Additionally, the maximum difference in the percentage of patients falling within a given patient satisfaction ranking (unchanged/worse, better, much better) at latest 2-year minimum follow-up between one cluster and the rest of the population was plotted.

FIG. 40 illustrates graphs of: within cluster sum of squares (WCSS) (top left), Silhouette score (top middle), the percentage of significant pairwise difference in clinical outcomes (top right), and the maximum difference in relative proportion between a single cluster and the remaining population for each of the different patient satisfaction rankings (bottom row) for various combinations of predictor variables and cluster numbers for the Scapula bone in accordance with one or more embodiments of the present disclosure.

FIG. 41 illustrates graphs of: within cluster sum of squares WCSS (top left), Silhouette score (top middle), the percentage of significant pairwise difference in clinical outcomes (top right), and the maximum difference in relative proportion between a single cluster and the remaining population for each of the different patient satisfaction rankings (bottom row) for various combinations of predictor variables and cluster numbers for the Deltoid muscle in accordance with one or more embodiments of the present disclosure.

In at least some embodiments, the elbow of the WCSS, which may be considered the optimal number of clusters from a compactness standpoint, does not shift based on the number of predictors, despite scaling differences in the magnitude. On the other hand, the silhouette score, a measure of both compactness and separation of clusters, is higher when less clusters may be used and when only 4 predictors may be used versus 8, 12, or all. A higher silhouette score may be considered better from a cluster compactness and separation standpoint. Additionally, the percentage of pairwise significant differences in outcomes between clusters is largely not impacted by the number of predictors, but increases with a lower number of clusters. However, low numbers of clusters may represent a trade-off relative to clinical specificity with detection of outliers. This may be illustrated by the patient satisfaction charts, which generally show there is larger separation between at least one cluster and the rest of the population within a given satisfaction ranking with an increased number of clusters. In this manner, various internal validation and clinical metrics may be analyzed separately or in parallel to understand the impact of clustering methodology and parameters on the ability of a resulting classification system identify patients that may have outlier outcomes and/or elevated risk of complications.

In at least some embodiments, it should be noted that additional internal validation metrics and/or clinical relevance metrics to objectively assess, compare, and optimize classification systems may be derived and deployed and the non-limiting example(s) herein may be intended to be representative of potential methodologies. Classification systems may also be formed separately on the basis of patient demographic information such as gender, and/or include patient demographic information/characteristics as target parameters. Once classification systems may be derived and optimized relative to technique/parameters, more detailed information pertaining to morphological variation, clinical outcomes, and/or complication risks may be analyzed and presented to aid the surgeon with interpretability of radiomic measurements, groups within which a given patient falls based on these measurements, and whether or not these groups of patients may have outlier performance or complication risks.

In at least some embodiments, as an example, to facilitate clinical interpretation of the radiomic features in an analysis of >4000 shoulder arthroplasty patients, an unsupervised ML clustering analysis may be performed to aggregate the most predictive radiomic measurements of deltoid muscles and/or scapula bones into distinct morphological groups and/or classes within the study population. Specifically, a centroid-based k-means clustering algorithm may analyze a deltoid muscle cohort and/or a scapular bone cohort, using the top 8 most predictive radiomic measurements, for example, from the feature importance analysis, along with patient age and gender. Four clusters (4F, 4M) for each deltoid muscle and scapular bone may be defined. Pre-operative and 2-year minimum post-operative clinical outcomes (deltoid muscle cohort=37.9±15.1 months, scapular bone cohort=37.7±14.8 months) may be compared using a Kruskal-Wallis to identify whether clusters may be associated with different outcomes, where $p<0.05$ defined significance.

Figure 6:
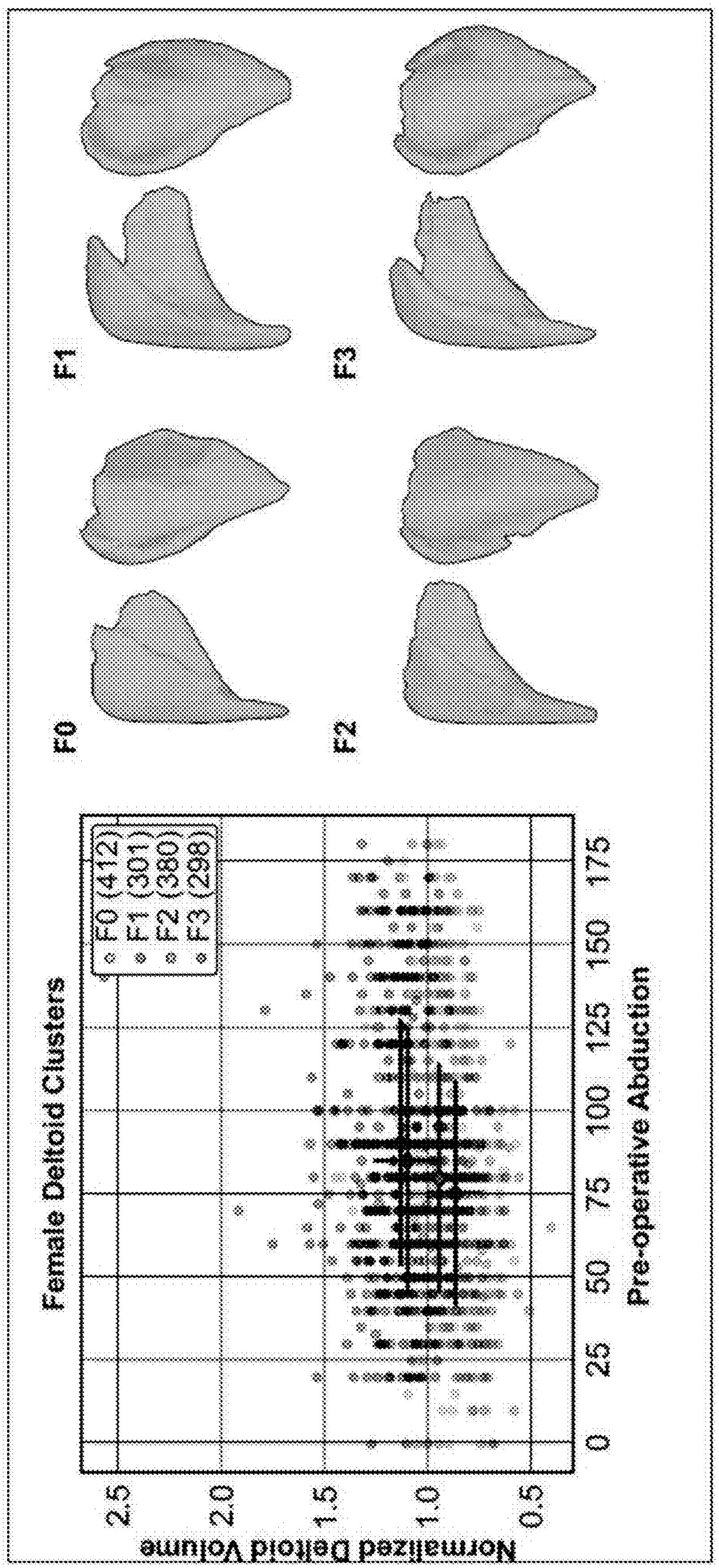

FIG. 6 is a Scatter Plot of Pre-operative Abduction vs. Deltoid Volume Normalized by Age and Gender (left), with Corresponding 3D CT Reconstructed Deltoids Representative (i.e. Near) of the Centroid of each of the 4 Female Deltoid Cluster Cohorts. Note that Female Deltoid Cluster F1 is associated with Significantly more Pre-operative Abduction than Female Deltoid Cluster F2, as shown in the Table of FIG. 35 below in accordance with one or more embodiments of the present disclosure.

Figure 7:
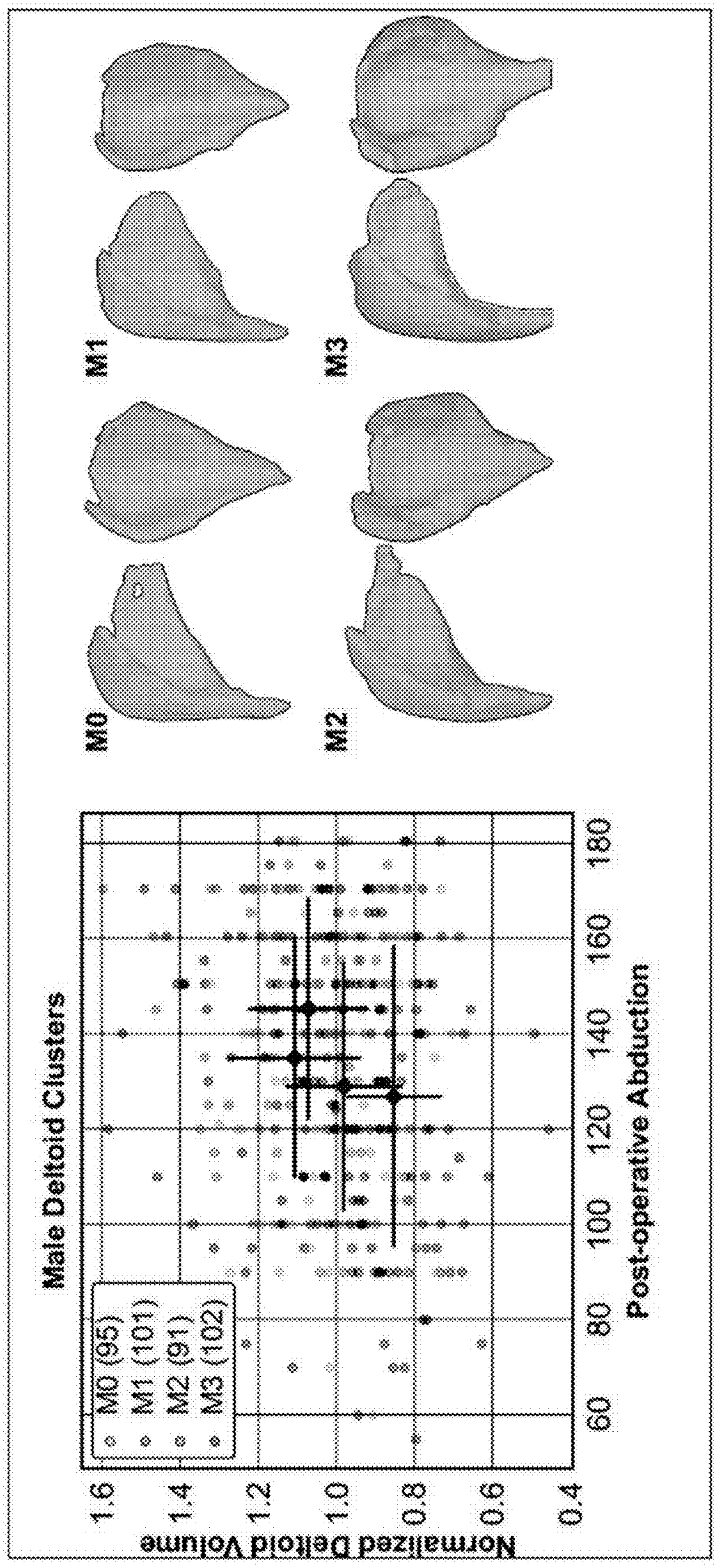

FIG. 7 is a Scatter Plot of 2-year Minimum Abduction vs. Deltoid Volume Normalized by Age and Gender (left), with Corresponding 3D CT Reconstructed Deltoids Representative (i.e. Near) of the Centroid of each of the 4 Male Deltoid Cluster Cohorts. Note that Male Deltoid Cluster M2 is associated with Significantly more 2-year Minimum Abduction than Male Deltoid Cluster M1, as shown in the Table of FIG. 36 below. in accordance with one or more embodiments of the present disclosure.

Figure 8:
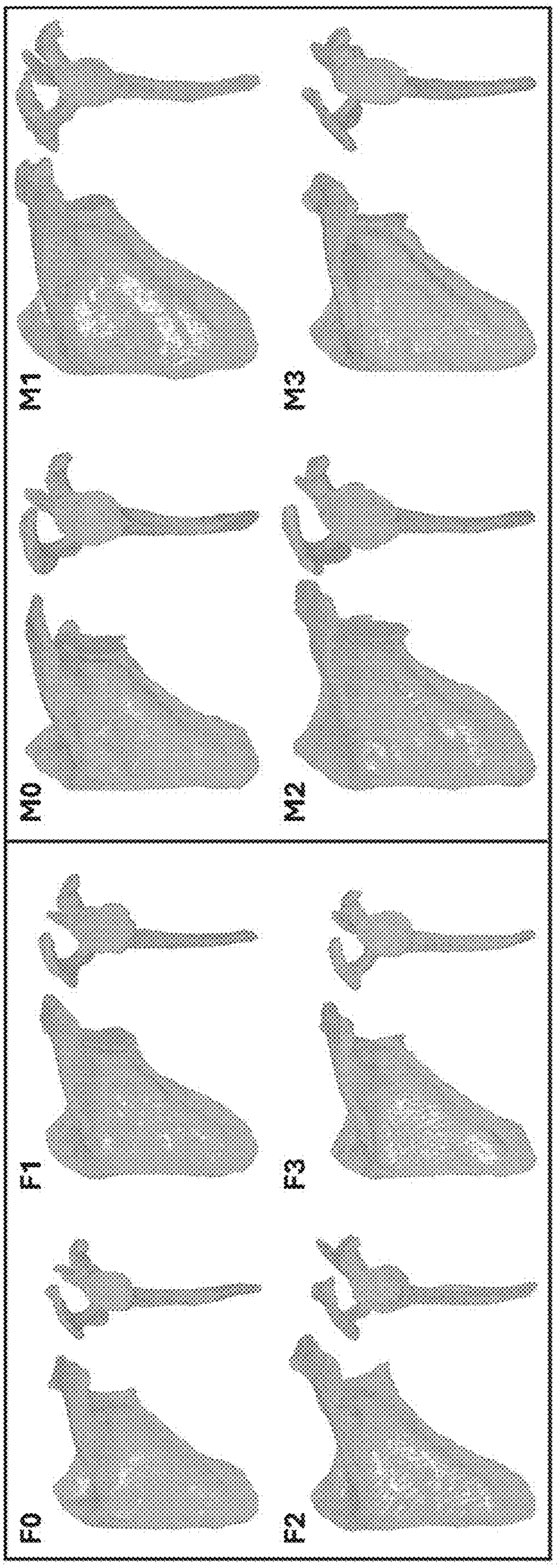

FIG. 8 illustrates 3D CT Reconstructed Scapula Representative (i.e. Near) of the Centroid of each of the 4 Female (Left) and 4 Male (Right) Deltoid Cluster Cohorts in accordance with one or more embodiments of the present disclosure.

FIG. 34 is a table showing a distribution of Deltoid Muscle Radiomic Measurements and Patient Demographics Associated with Male and Female Deltoid Clusters in accordance with one or more embodiments of the present disclosure.

FIG. 35 is a table showing a comparison of Deltoid Clusters to Pre-operative Clinical Outcomes Measures of Active Range of Motion, Pain, Function, and Patient Reported Outcome Measures for Male and Female Patients in accordance with one or more embodiments of the present disclosure.

FIG. 36 is a table showing a comparison of Deltoid Clusters to 2-Year Minimum Clinical Outcomes Measures of Active Range of Motion, Pain, Function, and Patient Reported Outcome Measures for Male and Female Patients in accordance with one or more embodiments of the present disclosure.

In at least some embodiments, using the image-based radiomic measurements, clusters may be created for 4 unique deltoid muscles (FIGS. 6-7) and 4 unique scapular bones (FIG. 8) for male and female patients who received aTSA or rTSA. The distribution of image-based data used in these deltoid muscle clusters is described in the Table of FIG. 34. Some of these deltoid muscle clusters and scapular bone clusters were associated with significantly more/less motion, function, and pain before/after shoulder arthroplasty, though clusters were not associated with differences in every outcome measure. Where specifically as described in the Table of FIG. 35, significant differences between at least two deltoid muscle clusters for male patients in abduction, forward elevation, IR score, Constant score, and SAS Score prior to surgery. Similarly, as described in in the Table of FIG. 35, deltoid muscle clusters for female patients were identified with significant differences in abduction (see FIG. 6), forward elevation, IR score, external rotation, VAS pain score, global shoulder function score, Constant score, ASES score, and SAS Score prior to surgery. As described in in the Table of FIG. 36, deltoid muscle clusters for male patients were identified with significantly better/worse abduction (see FIG. 6), IR score, and external rotation at 2-years minimum follow-up. Similarly, as described in in the Table of FIG. 36, deltoid muscle clusters for female patients were identified with significantly better/worse forward elevation, IR score, global shoulder function score, Constant score, ASES score, and SAS Score at 2-years minimum follow-up.

FIG. 37 is a table showing a distribution of Scapular Bone Radiomic Measurements and Patient Demographics Associated with Male and Female Deltoid Clusters in accordance with one or more embodiments of the present disclosure.

FIG. 38 is a table showing a comparison of Scapula Clusters to Pre-operative Clinical Outcomes Measures of Active Range of Motion, Pain, Function, and Patient Reported Outcome Measures for Male and Female Patients in accordance with one or more embodiments of the present disclosure.

FIG. 39 is a table showing a comparison of Scapula Clusters to 2-Year Minimum Clinical Outcomes Measures of Active Range of Motion, Pain, Function, and Patient Reported Outcome Measures for Male and Female Patients in accordance with one or more embodiments of the present disclosure.

In at least some embodiments, the distribution of image-based data used in these scapular bone clusters may be described in the Table in FIG. 37. Comparing the scapular bone clusters to clinical outcomes may also demonstrate significant differences between at least 2 scapular bone clusters for male patients in IR score, global shoulder function score, and constant score prior to surgery. Similarly, as described in the Table in FIG. 38, scapular bone clusters for female patients may be identified with significantly differences in abduction, external rotation, VAS pain score, and ASES score prior to surgery. Finally, as described in the Table in FIG. 39, scapular bone clusters for female patients may be identified with significantly better/worse external rotation at 2-years minimum follow-up; no 2-year minimum clinical outcome differences in scapular bone clusters were observed for male patients.

In at least some embodiments, these classes and/or clusters of patients may be identified prospectively and may be utilized in the software, such that when a physician and/or health care professional may upload their patient's medical image into the planning software, the framework may be able to automatically assign one or multiple classifications (e.g. clusters) which may most closely represent and/or resemble that patient's 3D reconstruction and associated image-based measurements. This software may include a library of classifications, and those classifications which may most closely represent and/or resemble the patient may be communicated to the physician and/or health care professional. These classifications may be trained and developed for numerous use cases. For example, classes may be developed which may be associated with good, medium, and/or poor results for any number of different clinical outcome measures (ROM, pain, function, PROMs) and/or may identify patients who may have the greatest risk (or lowest risk) for any number of different complications. For example, if the library of classification systems may include multiple bone and/or muscle classes associated with patients who may be at high risk and/or low risk for different complications, including implant loosening (e.g. glenoid loosening or humeral loosening), bone fracture, muscle tears, tendon or ligament tears, etc, then any and all classifications which may most closely represent and/or resemble that patient's bone and/or muscle, may be communicated to the physician and/or health care professional, so that they may better communicate to the patient the risks and benefits of a given treatment. This method of training a hierarchy of classification systems may be based on different risk factors and prospectively matching any and all relevant classes and/or clusters that may resemble a given patient from this library may be potentially an effective software workflow for personalized risk management to identify patients with risk factors for complications and/or lower potential for improvement.

In at least some embodiments, the clinical applications of prospective assignment of classification models within the CDST from a pre-trained library of ML derived classes may have many uses beyond just the prediction of outcomes after one or multiple treatments. For example, this method of prospective classification assignment may be effectively utilized within the image-based planning software to perform a diagnosis of a clinical pathology, identification of a unique anatomic morphology, and/or identification of tumors, anomalies, or fracture patterns. As an example, in the case of shoulder arthroplasty, patients that may be treated with aTSA or rTSA may typically be diagnosed with osteoarthritis, osteonecrosis, irreparable rotator cuff tears with or without arthritis, rotator cuff tear arthropathy, rheumatoid arthritis, or proximal humerus fracture (acute or sequelae). One or multiple classification systems may be trained for each of these different diagnoses (including subcategories within these classifications to describe joint wear patterns-like Walch or Favard or Antuna classification glenoid wear and/or defect systems) and then the planning software may prospectively assign the class or groups of classes which may most closely represent and/or resemble the image-based measurements associated with a particular patient as method of diagnosis and/or as a confirmation of diagnosis by the physician and/or health care professional. One clinical benefit of this approach may be that a given patient may very likely be prospectively assigned one or multiple classes for different diagnoses, which may imply that the historical diagnosis classification methods may be incomplete and patients may actually experience a continuum of degenerative conditions as opposed to one single diagnosis consisting of a narrow definition. This method of deployment of pre-trained classification systems for diagnoses may be deployed to create new, more granular diagnosis classifications which may better define a patient's condition (on a continuum) prior to treatment.

In at least some embodiments, regardless of the clinical use case, different ML based methods may be utilized to derive these classification systems, for example, principal component analysis or clustering. Additionally, there may be multiple different methodologies associated within a given technique. For example, there may be multiple different clustering techniques (centroid-based, hierarchical, density based, distribution based, etc.), different input parameters, and also different types of input data. Regarding the input data, there may be many different types of image-based data that may be used to train the ML classification algorithms. For example, in the case of shoulder arthroplasty, the planning software may utilize traditional joint degeneration or joint relationship measurements, like glenoid retroversion angle, beta angle, or humeral head subluxation percentage. These measurements may be automatically collected by the software from a 3D reconstructed image. Additionally, if using radiomic based measurements as ML model inputs, clustering algorithms may use shape-based measures, first-order measures, second-order/texture measures, embeddings, and/or from any combination of these image-based measurements. Additionally, many different datasets may be used to supplement these image-based data when training this library of classifications. For example, various data may be readily available in the patient's electronic medical record (blood work, subjective pain scores, range of motion data, comorbidities, demographics, previous medical history, etc.) and any or all of that data may be used as inputs to the ML models when building this library of clusters/classifications.

In at least some embodiments, another potential application of this prospective class assignment method may be to define important different clinically relevant thresholds for treatment, for example: 1) to define when a patient stops being "healthy" and actually may have a diagnosis for a pathology (by comparing an individual patient's class to that of classes developed from healthy control patients), 2) to define when a patient may need to transition from one type of treatment (a more conservative treatment, like physical therapy, NSAIDs, or a cortisone injection for pain) to another type of treatment (a more end-stage treatment, like joint replacement procedure like shoulder, hip, knee or ankle arthroplasty), or 3) to define the precise time in which a patient may get a joint replacement procedure as waiting longer may subject the patient to greater risk from performing the procedure or waiting longer will result in greater amounts of joint deformity which may make the procedure less bone-conserving and more difficult to recover from. Deployment of this type of application may have potential to greatly improve the surgeon-patient shared decision-making process by helping both the surgeon and patient learn, based on the aggregate previous experiences of similar patients, as to when may be the ideal time to perform the joint replacement surgery. Various methods may be used to visualize the stage in the process for an individual patient. For example, a dial clock may indicate if a particular patient may be early in the degenerative process and may indicate green for methods of treatment-suggesting that the patient may wait for 1-2 years before more aggressive treatments are necessary if they perform other tasks to reduce pain (NSAIDs, cortisone shots) and may improve function (physical therapy). Alternatively, the dial clock may indicate yellow or red if the patient is worse than typical patient and may be in need of more aggressive treatment options. For example, in the case of shoulder arthroplasty, the image-based software may calculate the amount of joint wear and may compare that to other image-based measurements, where specifically a cluster based model may be developed from the glenoid vault measurements for patients who may have previously had glenoid loosening after shoulder arthroplasty and may be compared to a given patient in order to determine if that particular patient already may have had a significant amount of glenoid wear (which may progress with time) and may compromise the ability to place an implant where desired based on increased risk of glenoid implant loosening.

Figure 9:
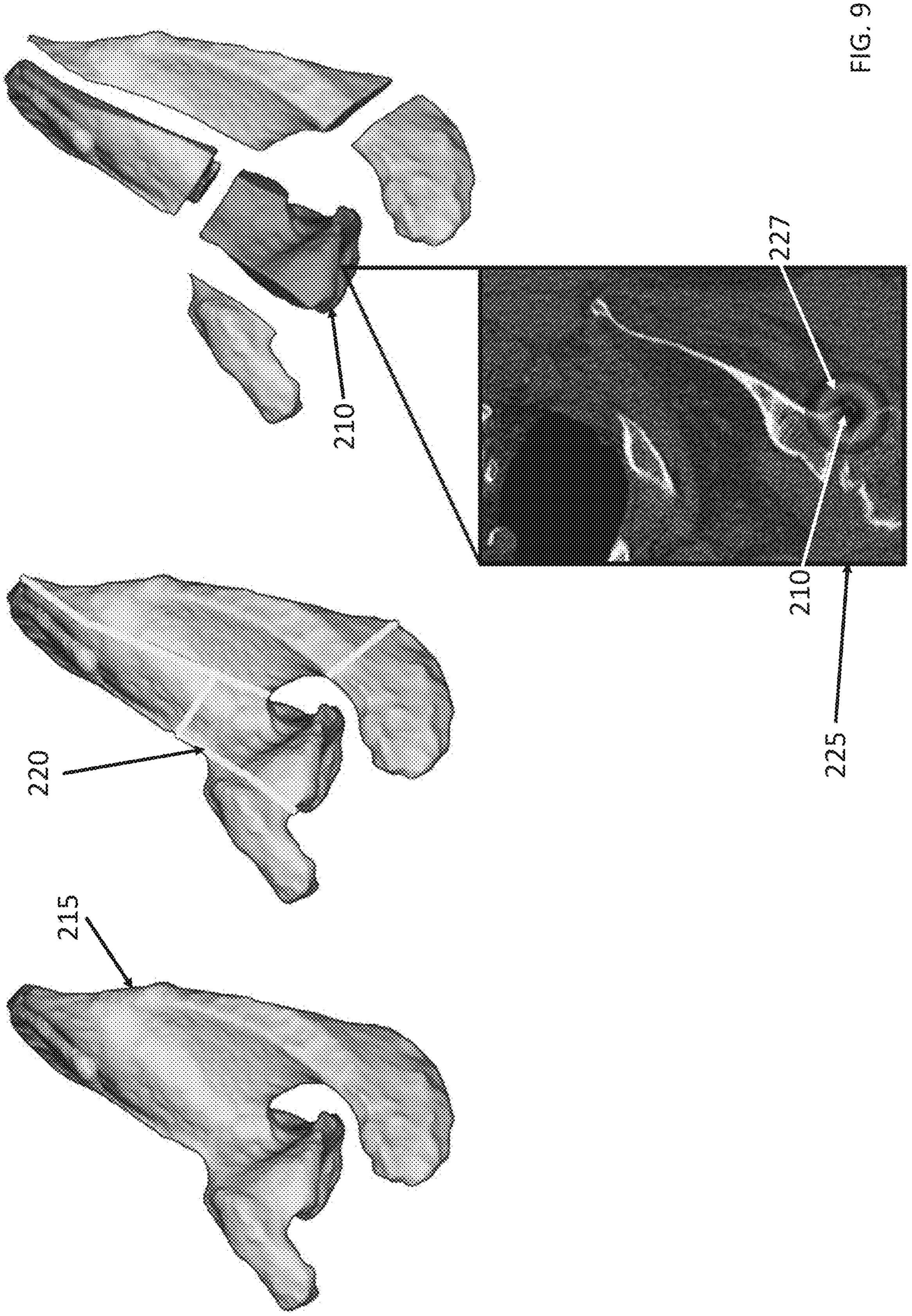

In at least some embodiments, another post-operative application may be to redefine the complication risk for a patient after the procedure based on the specific implants and techniques used to perform the procedure. For example, if a surgeon may utilize thicker implants than was originally planned when performing an aTSA procedure, that patient may have an elevated risk of rotator cuff failure and an image-based assessment from a medical image may be used to identify that the rotator cuff muscles may have an elevated strain (change in length divided by native/pre-operative length) because they have been stretched beyond their native length by the use of the thicker implant components (relative to the amount of bone removed during the procedure). The software may calculate the change in length and may also calculate the strain in the deltoid and/or rotator cuff by comparing the prosthesis displacement for a given configuration, position, and use of a specific implant size. Another application of this type of image-based joint relationship calculation may be to perform this calculation prior to the procedure for all the various combinations of implants sizes and combinations and to recommend against specific combinations of sizes, and/or positions for surgical planning that will result in elevated strain. Moreover, these image-based measurements may be used as inputs to computational models/finite element analyses which may be incorporated into the software and/or used to simulate stresses and strains in the bone, muscles, and/or implants for various implant size/type configurations and/or various implant positioning on the bone for different physiologically-relevant loading scenarios. In doing so these inputs and corresponding computational models may effectively generate a "digital twin" that may be utilized by the clinician to simulate different clinical decisions that may reduce the occurrence of complications, such as evaluation and/or selection of different treatment types, different implant types/sizes/configurations, and/or different implant positioning for a given surgical technique in order to minimize complication risk and/or probability of occurrence of a risk by reducing bone or soft tissue stresses, etc. Similarly, these inputs and corresponding computational models may be utilized by the clinician to simulate different clinical decisions that may impact post-operative factors of interest to the patient, such as pain, impingement, range of motion, and/or patient reported outcome measures or other functional measurements, such that this tool may be used to help the clinician make decisions that optimize these factors based on the needs of the patients. FIG. 9 illustrates Multiple views of 3D reconstructions of a scapular bone (left), with segmentation of the 3D volume into anatomically relevant sub-volumes of scapular bone segments for localized radiomic analysis (middle), in this example (right), outlier image-based measurements (relative to a patient reference group) of the glenoid vault displayed for visual interpretation in accordance with one or more embodiments of the present disclosure. Particularly, FIG. 9, as in FIG. 4, illustrates the scapula 215 having a region of interest (ROI) 210 of the glenoid vault and a ROI image map boundary 215 (e.g., ROI outline) that are the output of the at least one segmentation algorithm as described hereinabove. FIG. 9 also illustrates a medical image enlarged region 225 showing the glenoid vault within the shoulder with the region of interest 210 as highlighted 227. The ROI image map boundary 215 and the PVG corrected image data of the region of interest 210 of the scapula may be inputted into the at least one medical image analysis machine learning model that is trained to output at least one image based measurement in the region of interest 210 and at least one implant complication risk assessment for the implantation of the at least one implant into the joint.

Figure 10:
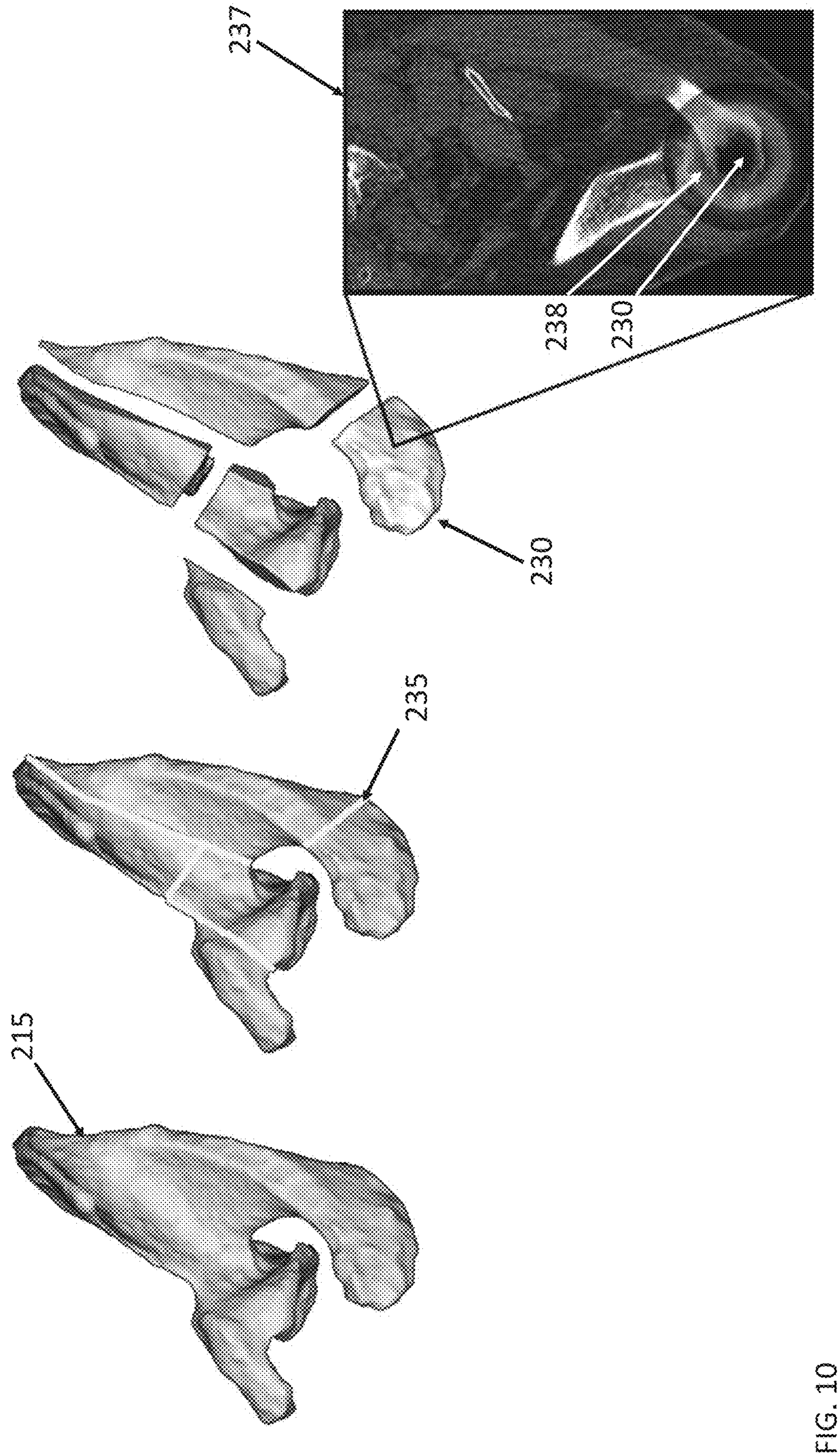

FIG. 10 illustrates multiple views of 3D reconstructions of a scapular bone (left), with segmentation of the 3D volume into anatomically relevant sub-volumes of scapular bone segments for localized radiomic analysis (middle), in this example (right), outlier image-based measurements (relative to a patient reference group) of the acromion displayed for visual interpretation in accordance with one or more embodiments of the present disclosure. Particularly, FIG. 10 illustrates the scapula 215 having a region of interest (ROI) 230 of the acromion and a ROI image map boundary 235 (e.g., ROI outline) that are the output of the at least one segmentation algorithm as described hereinabove. FIG. 10 also illustrates a medical image enlarged region 237 showing the acromion within the shoulder with the region of interest 230 as highlighted 227. The ROI image map boundary 215 and the PVG corrected image data of the region of interest 238 of the scapula may be inputted into the at least one medical image analysis machine learning model that is trained to output at least one image based measurement in the region of interest 230 and at least one implant complication risk assessment for the implantation of the at least one implant into the joint.

Figure 11:
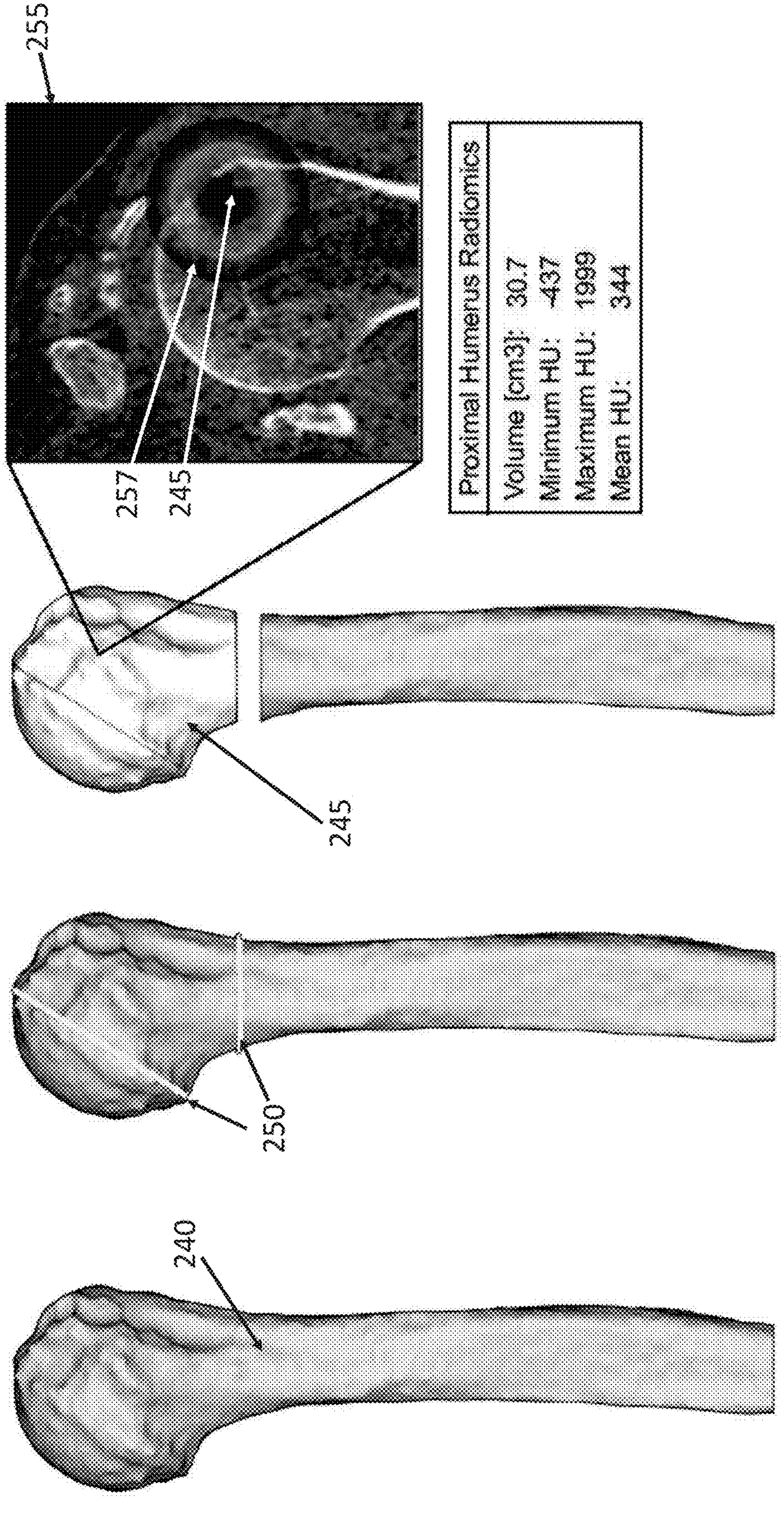

FIG. 11 illustrates multiple views of 3D reconstructions of the proximal humerus (left), with segmentation of the 3D volume into anatomically relevant sub-volumes of the proximal humeral bone segments for localized radiomic analysis (middle), in this example (right) outlier image-based measurements (relative to a patient reference group) of the proximal humerus are displayed and presented for visual interpretation in accordance with one or more embodiments of the present disclosure. Particularly, FIG. 11 illustrates the proximal humerus 240 having a region of interest (ROI) 245 of a bone segment of the proximal humerus 240 and a ROI image map boundary 250 (e.g., ROI outline) that are the output of the at least one segmentation algorithm as described hereinabove. FIG. 11 also illustrates a medical image enlarged region 255 showing the proximal humerus 240 within the shoulder with the region of interest 245 as highlighted 257. The ROI image map boundary 250 and the PVG corrected image data of the region of interest 245 of the proximal humerus 240 may be inputted into the at least one medical image analysis machine learning model that is trained to output at least one image based measurement in the region of interest 245 and at least one implant complication risk assessment for the implantation of the at least one implant into the joint.

Figure 12:
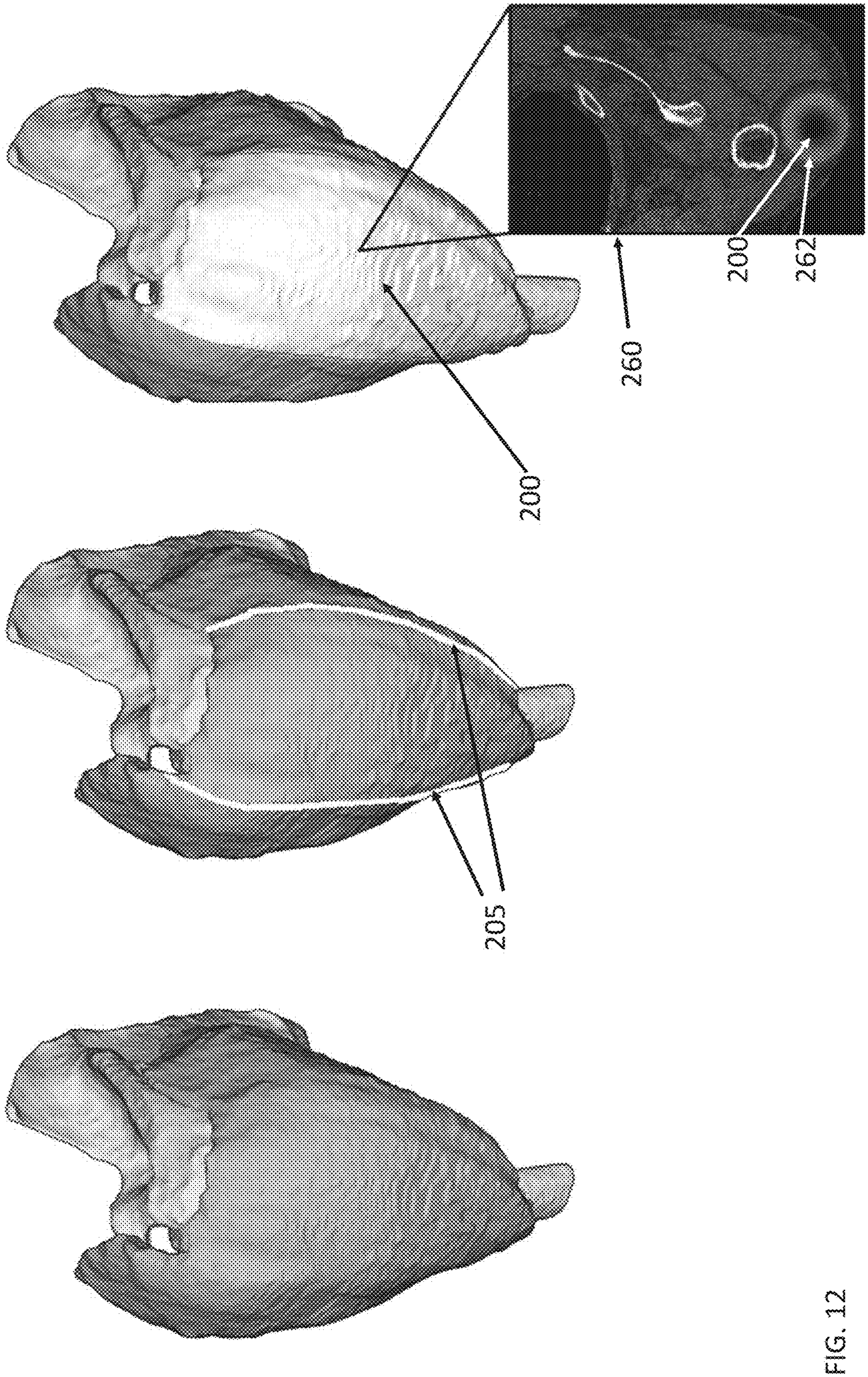

FIG. 12 illustrates 3D reconstructions of the scapula, proximal humerus, and deltoid muscle (left), with segmentation of the 3D muscle volume into anatomically relevant sub-volumes of the deltoid (middle deltoid, middle) for localized radiomic analysis (right), in this example (right) outlier image-based measurements (relative to a patient reference group) of the middle deltoid are displayed and presented for visual interpretation in accordance with one or more embodiments of the present disclosure. Particularly, FIG. 12, as in FIG. 3, illustrates the deltoid muscle as a region of interest (ROI) 200 and a ROI image map boundary 205 (e.g., ROI outline) that are the output of the at least one segmentation algorithm as described hereinabove. FIG. 12 also illustrates a medical image enlarged region 260 showing the deltoid muscle region of interest 200 within the shoulder as highlighted 262. The ROI image map boundary 205 and the PVG corrected image data of the region of interest 200 of the deltoid muscle may be inputted into the at least one medical image analysis machine learning model that is trained to output at least one image based measurement in the region of interest 200 and at least one implant complication risk assessment for the implantation of the at least one implant into the joint.

Figure 13:
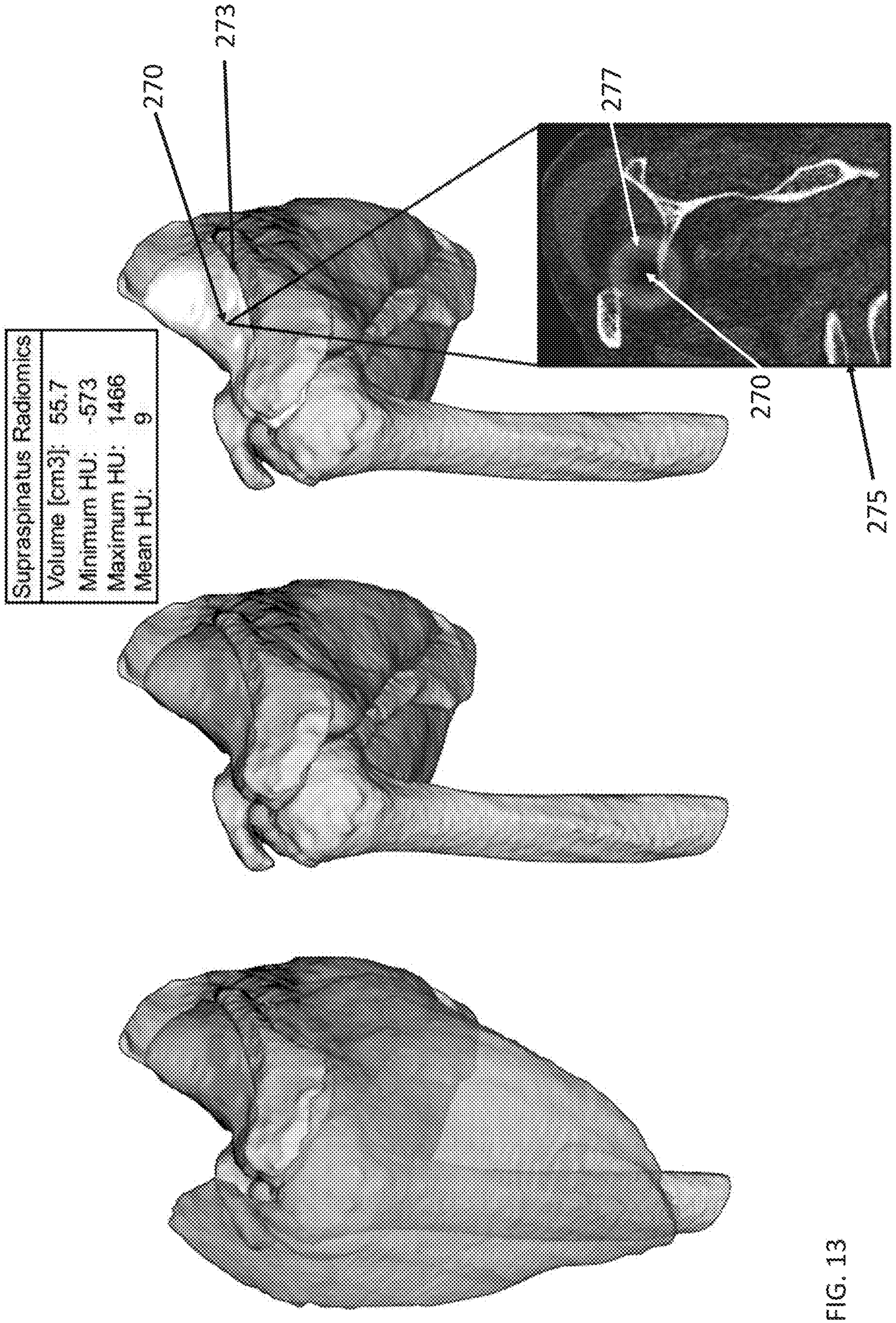

FIG. 13 illustrates 3D reconstructions of the scapula, proximal humerus, deltoid muscle, and rotator cuff muscles (left), with deltoid removed (middle, and with the supraspinatus rotator cuff muscle (right) highlighted for localized radiomic analysis (right), in this example (right) select radiomic measures of the supraspinatus are extracted and presented and outlier image-based measurements (relative to a patient reference group) of the supraspinatus are displayed and presented for visual interpretation in accordance with one or more embodiments of the present disclosure. Particularly, FIG. 13 illustrates the supraspinatus muscle as a region of interest (ROI) 270 and a ROI image map boundary 273 (e.g., ROI outline) that are the output of the at least one segmentation algorithm as described hereinabove. FIG. 13 also illustrates a medical image enlarged region 275 showing the supraspinatus muscle region of interest 270 within the shoulder as highlighted 277. The ROI image map boundary 273 and the PVG corrected image data of the region of interest 270 of the supraspinatus muscle may be inputted into the at least one medical image analysis machine learning model that is trained to output at least one image based measurement in the region of interest 270 and at least one implant complication risk assessment for the implantation of the at least one implant into the joint.

Figure 14:
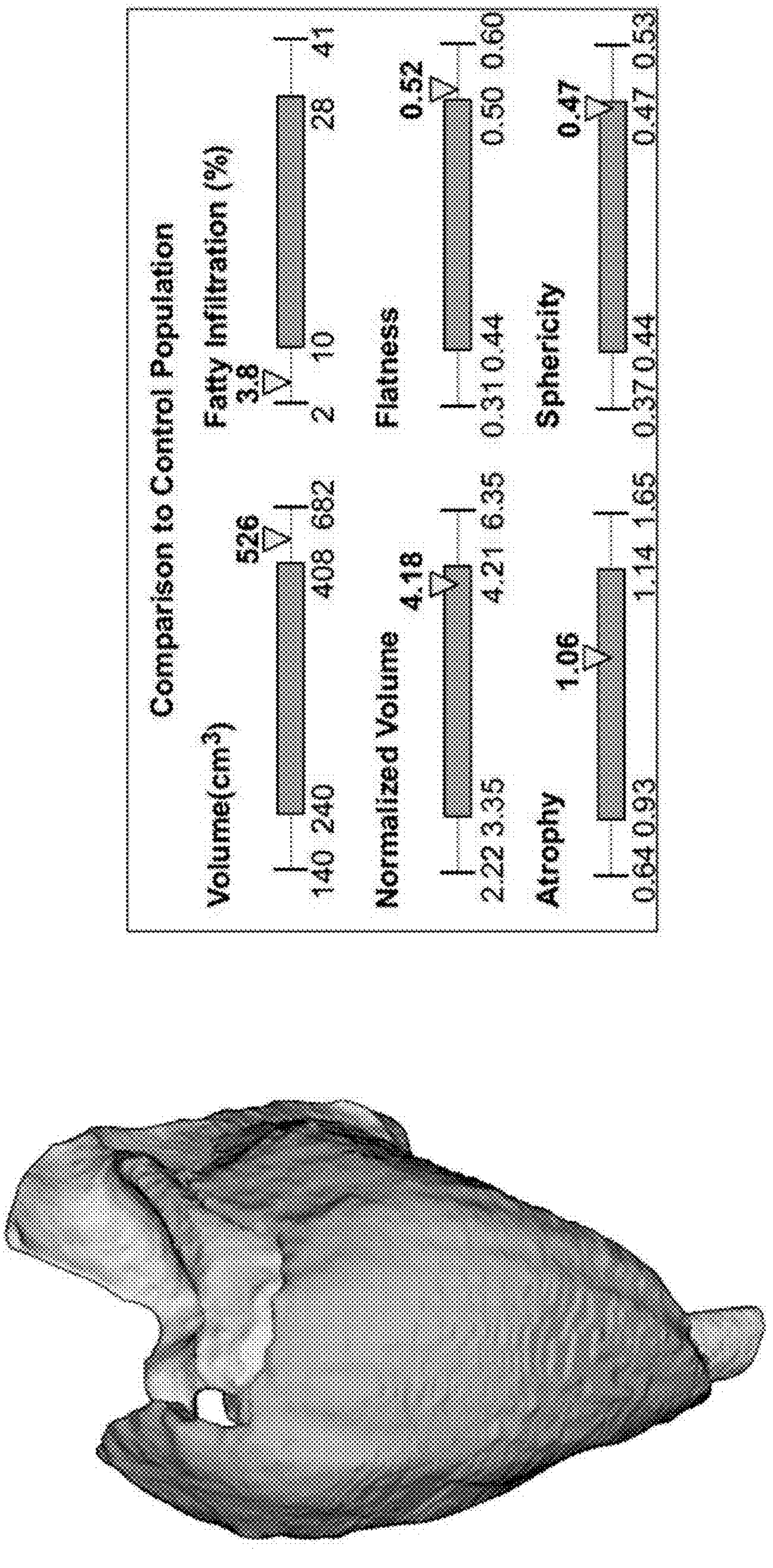

FIG. 14 illustrates 3D reconstructions of the scapula, proximal humerus, and deltoid muscle. The table below the reconstruction displays the extracted radiomic measures of the patient's deltoid muscle relative to a control/reference patient cohort of deltoid radiomic measures to provide the physician and/or health care professional context of this patient's image-based measurements in accordance with one or more embodiments of the present disclosure.

In at least some embodiments, the usability of an image-based CDST tool may be challenged with the presentation of highly granular data. As such, to improve the ease-of-use, it may be important that the method of communication of the clinically relevant data may be presented clearly and concisely to the user. There may be various methods to communicate the most important and clinically relevant data to the user. The ML based methods of developing classification systems presented above, when trained on data that may be composed of the greatest feature importance for a given clinical use case, may be a dimensional reduction technique to condense and/or aggregate the dataset to what may be most relevant to the user. However, there may be numerous additional methods to present the raw image data visually. One method may be a heat density map, or a class activation map may be used to help the physician and/or health care professional visualize a particular region of the image that may be clinically relevant. For example, for a patient with image-based measurements which may suggest that the patient may have a lesion and/or cavity in the scapular glenoid bone which may prevent the surgeon from achieving glenoid fixation. As depicted in FIG. 9, by the software directing the user to this region of interest, the likelihood that the surgeon may notice this bone abnormality may be increased, thereby reducing the risk that the region of poor-quality bone may be missed and ignored during the procedure. There may be many additional use cases for this kind of heat map identification of outlier data, for example, FIG. 10 depicts a heat map of image-based measurements of the acromion that may be outside the normal distribution of one or more measures of bone quality, density, and/or strength, in the acromion and/or scapular spine for an elderly patient who may be considering rTSA—for that patient, they may have an elevated risk of a scapular fracture). This software may be used to identify and communicate abnormalities in this manner from the full muscle, tendon, or ligament or from a sub-volume of any of these anatomic structures, if their image-based measurements may be outside the normal distribution relative to a comparison cohort, even if the abnormality may not be predictive of any particular complication. As additional examples, the bone defect in the proximal humerus depicted in FIG. 11, the abnormality in the middle deltoid depicted in FIG. 12, and abnormality in the supraspinatus rotator cuff muscle depicted in FIG. 13.

In at least some embodiments, heat maps may be visually effective, but communication of the raw data may be helpful for learning and future research applications. As such, the user interface of the software may be configured to have adaptive tables which may numerically represent the image-based measurements with the greatest feature importance for one or multiple outcomes. The user interface may output the one or multiple outcomes in tables that may be modifiable by the user so that they may flip through the various tables for different outcome predictions and/or complication predictions. These adaptive tables may also be configured to only present the patient's image-based data if it is outside of the expected range as defined by a predetermined patient cohort—for example, patients of the similar age, gender, diagnosis. As an example, these tables may be configured to filter out data by some statistical based method, like 1 or 2 standard deviations from the mean or as a location within the range of the patient control cohort, as depicted in FIG. 14. Furthermore, these tables may also have an adaptable user interface such that it displays data that may be more "abnormal" or further from the mean of the cohort using a color coding or a bar chart.

Some embodiments of the present disclosure presented many practical applications of creating a library of different classification models derived using various different ML based methods and trained on image-based measurements, which may be used in the planning software for a prospective assignment to an individual patient, for example:

1) Clinical outcome prediction tool (outcomes prediction to identify if a patient may have a more/less potential for clinical improvement after different treatments, this may be based on pre-operative image-based measurements and/or may be refined with additional post-operative image-based measurements)
2) Risk profiler complication prediction (complication prediction tool to help patients better understand if they have elevated risk factors for one or multiple postoperative complications after various treatments, this tool may be based on pre-operative image-based measurements and/or could be refined with additional post-operative image-based measurements)

3) Patient Expectation tool (combining these features into a single tool which communicates the patient specific potential for improvement, along with the risks and benefits of a given treatment, as compared to other patients)
4) Muscle size/shape/quality modeling/analysis tool for research and clinical purposes,
5) Bone size/shape/quality modeling/analysis tool for research and clinical purposes,
6) Tendon size/shape/quality modeling/analysis tool for research and clinical purposes,
7) Ligament size/shape/quality modeling/analysis tool for research and clinical purposes,
8) Joint characteristic tool to aggregate the measurements of the muscles, bone, tendons, and/or ligaments for all the anatomic structures in a joint, compare the relationships between those anatomic structures and compare trends associated with other patients for a more stratified, personalized analysis to a more relevant comparison cohort.
9) Diagnosis assignment and/or anatomy/morphology abnormality/outlier identification tool for research and clinical purposes
10) Treatment clock (to indicate when a patient may be treated with more conservative vs more aggressive treatments for a given pathology)

In at least some embodiments, a method may include performing at least one joint pre-surgical medical imaging procedure to image a portion of a joint of a patient prior to an implantation of at least one implant into the joint of the patient. By at least one processor (e.g., the at least one processor 45), image data of a plurality of medical images of the portion of the joint acquired from at least one medical imaging device (e.g., from the medical imaging system 35) may be received. A plurality of pixel-voxel granularity (PVG) corrected medical images may be generated by applying at least one PVG pre-processing algorithm (e.g., the medical imaging post-processing (PP) analyzer 48) to the image data of each image from the plurality of medical images. The at least one PVG pre-processing algorithm may be configured to: normalize pixel values in the image data in each medical image by adjusting pixel gray level intensity values within each medical image of the plurality of medical images to a common gray scale; resample the image data to increase or decrease a number of pixels in each medical image-based on a standard voxel size between images; and convert the pixel values in each image to digital pixel values to generate each PVG corrected medical image in the plurality of PVG corrected medical images. The at least one processor may segment the image data of each PVG corrected medical image of the portion of the joint using at least one segmentation algorithm to segment the plurality of PVG corrected medical images to identify at least one region of interest in the portion of the joint associated with: at least one bone member of the joint, at least one connective tissue associated with the joint, at least one muscle associated with the joint, or any combination thereof. The at least one region of interest in the portion of the joint and the plurality of PVG corrected medical images may be inputted by the at least one processor into at least one medical image analysis machine model (e.g., the medical imaging MLM 50) that may be trained to output: at least one image based measurement and/or at least one radiomic feature in the at least one region of interest, and at least one implant complication risk assessment for the implantation of the implant into the joint. At least one 3-dimensional (3D) representation of the joint and the at least one implant complication risk assessment based on the plurality of PVG corrected medical images may be displayed to a user on a display (e.g., via the GUI manager 56).

In at least some embodiments, the method hereinbelow that may be performed by the at least one processor 45 executing the surgical planning software 52 may further include receiving, by the at least one processor, pre-operative patient specific data for an arthroplasty surgery to implant the at least one implant in the joint of the patient. The pre-operative patient specific data (e.g., collected by the patient-specific data collection module 46) may include a medical history of the patient, a measured range of movement for at least one type of joint movement of the joint, and at least one pain metric associated with the joint. At least one arthroplasty surgical parameter based on the at least one implant complication risk assessment may be received, by the at least one processor, from the user. The at least one arthroplasty surgical parameter may include the at least one implant, at least one implant size, at least one arthroplasty surgical procedure, at least one position for implanting the at least one implant in the joint, or any combination thereof. A reconstruction plan of the joint of the patient may be generated based at least in part on the plurality of PVG corrected medical images of the joint, the at least one implant complication risk assessment, and the at least one arthroplasty surgical parameter. The pre-operative patient specific data and reconstruction plan data may be inputted into at least one postoperative joint performance machine learning model to determine a predicted post-operative joint performance data output at a plurality of post-operative timepoints after surgery. The predicted post-operative joint performance data output may include at least: a predicted range of movement for the at least one type of joint movement of the joint, and at least one predicted pain metric associated with the joint. The at least one postoperative joint performance machine learning model may be trained to output data comprising a plurality of values for the predicted post-operative joint performance data output at the plurality of post-operative timepoints after surgery, each value is at a particular timepoint of the plurality of post-operative timepoints after surgery. Input data to train the at least one postoperative joint performance machine learning model may include at least: the pre-operative patient specific data, the at least one implant complication risk assessment, the at least one region of interest in the portion of the joint, and the reconstruction plan data. The reconstruction plan data and the predicted post-operative joint performance data output at the plurality of post-operative timepoints after the arthroplasty surgery may be displayed on the display to the user. The arthroplasty surgery may be performed to implant the at least one implant based on the reconstruction plan of the joint of the patient and the at least one arthroplasty surgical parameter.

In at least some embodiments, the surgical assistance system 10 may be used to assist the surgeon during an arthroplasty surgical procedure identify at least one of but not limited to: at least one implant complication risk assessment, at least one post-operative outcome, at least one position of the implant into a joint, at least one size of the implant, at least one type of the implant, at least one resection associated with at least one of a first bone member or a second bone member at the joint, at least one soft tissue parameter, at least one position of at least one of the first bone member or the second bone member within the joint, an alignment angle of at least one of the first bone member or the second bone member, a flexion angle of at least one of the first bone member or the second bone member, or an axial rotation angle of at least one of the first bone member or the second bone member.

In at least some embodiments, the medical computing device 15 may be configured to operate in robotic and/or computer arthroplasty systems and/or other sensor devices that may include providing the graphic user interface 75 to the surgeon in the surgeon console where the surgeon sits to control the robotic arm or other similar instruments. In other embodiments, the at least one processor 45 may be configured to execute controller software for controlling a surgical robotic arm and/or the surgical instruments coupled to the robotic arm, or the highly precise and maneuverable arm that holds and manipulates the surgical instruments for performing the arthroplasty surgery.

In at least some embodiments, radiomic measurements may include quantitative descriptors that may be extracted from PVG corrected medical images within anatomically segmented regions of interest, such as muscles, tendons, ligaments, and/or bones. These descriptors may include shape features, first-order intensity statistics, and/or second-order texture features that may numerically characterize geometry, density, and spatial intensity organization. Shape features may include volume, surface area, surface-to-volume ratio, sphericity, flatness, elongation, principal-axis lengths, and maximum two-dimensional diameters in row, column, and slice planes. First-order features may include statistics derived from voxel intensities, such as mean, median, minimum, maximum, range, interquartile range, standard deviation, entropy, percentiles, skewness, and kurtosis. Texture features may include matrix-based statistics that may quantify spatial relationships among gray levels, including gray-level co-occurrence matrix (GLCM) measures such as contrast, correlation, homogeneity (Id), joint energy, joint entropy, maximum probability, autocorrelation, sum entropy, and maximal correlation coefficient; gray-level run length matrix (GLRLM) measures such as run entropy; gray-level size zone matrix (GLSZM) measures such as gray level variance, gray level non-uniformity normalized, size-zone non-uniformity normalized, low gray level zone emphasis, and zone entropy; gray-level dependence matrix (GLDM) measures such as dependence entropy, dependence variance, gray level variance, and large/small dependence emphases; and neighborhood gray-tone difference matrix (NGTDM) measures such as coarseness and strength. These radiomic measurements may be produced after normalization, resampling to a standard isotropic voxel size, and discretization, where such PVG preprocessing may improve robustness across scanners and imaging protocols.

In at least some embodiments, other image-based measurements may include quantitative outputs that may extend beyond hand-engineered radiomics by leveraging learned representations, geometric modeling, modality-specific biophysical surrogates, and/or planning-oriented joint metrics. Such other measurements may include deep learning embeddings and intermediate feature maps that may encode high-level morphological patterns; class activation maps and saliency maps that may localize image regions influential to model predictions; bone mineral density surrogates and Hounsfield unit-derived density gradients; mesh-based or statistical shape model parameters, principal geodesic modes, local and principal curvature, cortical thickness maps, signed distance fields, and geometric strain proxies; joint relationship and alignment metrics that may include joint space width, congruency, subluxation percentages, version and inclination angles, center of rotation, and impingement clearances; multi-scale texture and structure measures such as fractal dimension, lacunarity, structure tensor metrics, Gabor filter responses, and local binary patterns; registration-derived deformation field summaries that may capture local expansions, compressions, and asymmetries; segmentation uncertainty maps that may quantify boundary confidence; lesion and defect quantifications such as cystic volume, sclerotic rim thickness, osteophyte burden, erosions, marrow edema, and subchondral voids; biomechanics-informed surrogates that may estimate contact patches, contact pressure tendencies, moment arms, and surrogate strain fields; and modality-specific parameters, including T1/T2/T2*relaxometry, diffusion-weighted apparent diffusion coefficients, dynamic contrast-enhanced time-intensity parameters, ultrasound elastography shear wave velocities, and PET standardized uptake values.

In at least some embodiments, radiomic measurements may emphasize standardized, interpretable descriptors that may be directly calculated from voxel intensities and segmented geometries, while other image-based measurements may emphasize learned latent features, higher-order geometric constructs, registration- or biomechanics-derived surrogates, and multi-modal physiological parameters. Radiomic measurements may be particularly suited to robust, reproducible quantification after PVG preprocessing and may provide consistent inputs to predictive models, risk assessment, prospective class assignment, and outlier detection. Other image-based measurements may complement radiomics by capturing information that radiomics may not fully represent, such as complex appearance patterns learned by neural networks, patient-specific anatomical relationships important to implant planning, localized regions of abnormality highlighted by class activation techniques, and modality-specific biophysical signals that may inform tissue quality and function. Together, these measurement families may provide a comprehensive quantitative foundation that may enable the clinical decision support tool to transform heterogeneous medical images into actionable prognostic and prescriptive insights.

FIG. 42 is an exemplary flow diagram 100 for modeling predictive outcomes of arthroplasty surgical procedures in accordance with one or more embodiments of the present disclosure. The exemplary flow diagram 100 with reference to FIG. 1 may include the patient 25 entering a clinic (step 105) to consult with the doctor 20 about an arthroplasty surgical procedure to improve or replace a joint. The doctor 20 may collect pre-op patient-specific data from the patient 25 that may be entered into the patient-specific data collection module 46 executed by the processor 45 on the computing device 77. Alternatively, and/or optionally, the patient-specific data collection module 46 may query the plurality of N electronic resources (40A and 40B) for patient-specific pre-operative data that may be received by the server 15 over the communication network 30. The received dataset may include pre-operative patient specific data for an arthroplasty surgery to be performed on a joint of a patient where the pre-operative patient specific data may further include a medical history of the patient, a measured range of movement for at least one type of joint movement, at least one pain metric associated with the joint, or any combination thereof.

In at least some embodiments, the received pre-operative patient specific data may be inputted to an initial preop prediction machine learning model (MLM) 115. The initial preop prediction MLM 115 may determine a first predicted post-operative joint performance data output that includes at least one first predicted post-operative performance metric of the joint, which may then be displayed on the display of the computing device 77 to a user, such as the user 20 (e.g., the doctor 20), for example.

In at least some embodiments, the doctor 20 and the patient 25 may have an initial patient consultation 120. The doctor 20 and/or the patient 25 may decide to continue with the arthroplasty surgery of the joint, or to delay the surgery or to pursue other treatment 125 for the diseased joint.

In at least some embodiments, the doctor 20 may request that the patient 25 may receive at least one medical image of the joint, such as a computerized tomography (CT) scan 130, for example, obtained from at least one medical imaging procedure performed on the patient 25. The at least one medical image of the joint may include an X-ray image, a computerized tomography (CT) image, a magnetic resonance image, a three-dimensional (3D) image, and/or a 3D medical image based on multiple X-ray images. The at least one medical image of the joint may also include images of the bones and/or the connective tissues attached to and/or forming the joint.

In at least some embodiments, in a guided personalized surgery (GPS) Preop Planning 135 step, a CT image-based (GPS) Joint Reconstruction Planning module, which may be a software program executed by the processor 45, may generate a reconstruction plan of the joint that is display on the GUI 75. The CT image-based (GPS) Joint Reconstruction Planning module may be part of the surgical planning software module 52 of the clinical decision support software 80.

In at least some embodiments, the reconstruction plan may utilize at least one arthroplasty surgical parameter chosen by the doctor in response to the doctor viewing the first predicted post-operative joint performance data output. The reconstruction plan may include at least one arthroplasty surgical parameter that is selected from, but not limited to, at least one implant, at least one implant size, at least one arthroplasty surgical procedure, and/or at least one position for implanting the at least one implant in the joint. The reconstruction plan may include different views of the at least one medical image of the joint, such as the CT scan 130, that may be displayed on the GUI 75 along with images of the at least one implant implanted in the joint.

In at least some embodiments, the at least one arthroplasty surgical parameter may be inputted to a final Preop prediction model 140. The at least one arthroplasty surgical parameter may include any of the data inputs to the final Preop prediction model 140.

In at least some embodiments, the data inputs to the final Preop prediction model 140 may include any of the inputs to the initial preop prediction MLM 115 as well as any suitable parameters extracted from the reconstruction plan.

In at least some embodiments, the surgical planning software module 52 may include the initial preop prediction MLM 115 and/or the final Preop prediction model 140.

In at least some embodiments, the initial preop prediction MLM 115 and the final Preop prediction model 140 may be the same machine learning model.

In at least some embodiments, the software application for modeling the predictive outcomes of arthroplasty surgical procedures may be executed by the processor 45 and the GUI manager 56 may remotely control the GUI 75 running on the computing device 77 for providing inputs and/or outputs from the server 15.

In at least some embodiments, the first predicted post-operative joint performance data output and/or the second predicted post-operative joint performance data output may be displayed on the GUI 75 to the doctor 20 in any suitable format, such as outputting a list of predicted post-operative outcome metrics of the joint based on data inputs such as pre-operative patient specific data, medical images of the joint, and arthroplasty surgical parameters to the predictive outcome machine learning models. A visual representation of the implant implanted in a joint based on the medical images of the joint. The visual representation of the implant implanted in a joint may include raw, enhanced, and/or augmented images of the joint that may be displayed on GUI 75.

In at least some embodiments, the second predicted post-operative joint performance data output may include displaying on the GUI 75 at least one arthroplasty surgery recommendation of combinations of surgical procedures, implant types, implant sizes, implant positions along with the predicted post-operative outcome metrics from the models for each combination so as to allow the surgeon to optimize the post-operative joint performance by varying the arthroplasty surgical parameters. This optimization may be performed before and/or during the surgery.

In at least some embodiments, the at least one arthroplasty surgery recommendation may include a recommendation not to proceed with the arthroplasty surgical procedure and/or to pursue another treatment.

In at least some embodiments, the final Preop prediction model 140 may determine a second predicted post-operative joint performance data output that includes the at least one second predicted post-operative performance metric of the joint, which may then be displayed on the GUI 75 of the computing device 77 to a user, such as the doctor 20, for example.

In at least some embodiments, the doctor 20 may review second predicted post-operative joint performance data output and conduct a final patient consultation 145 with the patient 25. The doctor 20 and/or the patient 25 may decide to schedule the arthroplasty surgery 155 of the joint, or to delay the surgery or to pursue other treatment 150 for the diseased joint.

In at least some embodiments, FIG. 42 for modeling flow of predictive outcomes of arthroplasty surgical procedures that may also integrate radiomic image processing within the outcome modeling steps, where the flow may include receiving standard of care medical images, applying PVG preprocessing that may normalize gray level intensities, may resample to an isotropic voxel size, and may discretize intensities, performing at least one segmentation that may generate at least one ROI image map boundary and an at least one ROI image map, extracting image based measurements and/or at least one radiomic features that may include shape, first order intensity, and second order texture measures from the ROI, and passing these features to the medical imaging MLM module 50 which, together with patient specific data and surgical planning parameters, may generate at least one implant complication risk assessment and predicted postoperative joint performance metrics at multiple timepoints; the flow may further include visualization and alert steps that may display heat maps, class activation maps, and color coded indicators on the ROI, and may provide prospective class or cluster assignments, so that the image based measurements and/or radiomic features and ML outputs may be reused downstream in the decision steps of FIG. 42 to update recommendations and may enable iterative optimization of implant type, size, and position.

In at least some embodiments, the clinical decision support software 80 of FIG. 1 may include a coordinated set of algorithms mapped to its modules. The Medical Imaging Pre-Processing (PP) Analyzer 48 may include PVG preprocessing that may normalize gray-level intensities using z-score normalization. It may resample to an isotropic voxel size using B-spline or Welch-Sinc interpolation. It may discretize intensities using fixed bin width or fixed bin count strategies.

In at least some embodiments, the Medical Imaging MLM module 50 may include segmentation algorithms that may be automated, semi-automated, or manual with anatomical priors, landmarks, or bounding boxes. It may include U-net or other neural network architectures. It may execute image based measurement extraction and/or radiomic feature extraction that may include shape, first-order intensity, and second-order texture families such as GLCM, GLRLM, GLSZM, GLDM, and NGTDM. It may use deep learning representation methods that may include embeddings, saliency maps, and class activation maps. It may apply dimensionality reduction that may include principal component analysis. It may run unsupervised classification that may include centroid-based k-means clustering with internal validation metrics such as WCSS and Silhouette score. It may perform outlier detection that may include statistical thresholding against reference cohorts. It may compute feature importance rankings that may include F-score analyses. It may generate complication risk assessments that may predict instability, aseptic loosening, fracture, infection, and revision. It may produce postoperative joint performance models that may predict timepoint-specific range of motion and pain metrics.

In at least some embodiments, the Model Training module 54 may include XGBoost regression and classification pipelines. It may include neural network training workflows with periodic or continual retraining. It may include cluster optimization across predictor sets and cluster counts.

In at least some embodiments, the Surgical Planning Software 52 may include iterative optimization routines that may adjust implant type, size, and position based on predicted outcomes and risk signals. It may include digital twin or biomechanics-informed computations that may estimate contact tendencies and surrogate strain fields. It may include statistical shape modeling and geometric analysis that may evaluate principal geodesic modes, curvature, cortical thickness, and signed distance fields. It may include registration-driven deformation field analyses that may summarize local expansions and compressions. It may include multi-scale texture and structure analyses that may include fractal dimension, lacunarity, structure tensor metrics, Gabor filters, and local binary patterns.

In at least some embodiments, the GUI Manager 56 may include visualization algorithms that may render heat maps, class activation overlays, color coded indicators, 3D representations, and alerts. The Patient Specific Data Collection module 46 may ingest demographics, comorbidities, diagnosis, PROMs, and ROM data for integration with the imaging driven algorithms across the platform.

In at least some embodiments, the processor 45 may be configured to receive pre-operative patient specific data for an arthroplasty surgery to implant the at least one implant in the joint of the patient. The pre-operative patient specific data may include for example, but not limited to a medical history of the patient, a measured range of movement for at least one type of joint movement of the joint, and at least one pain metric associated with the joint. The processor 45 may be further configured to receive from the user, at least one arthroplasty surgical parameter based on the at least one implant complication risk assessment. The at least one arthroplasty surgical parameter may be selected from, but not limited to the at least one implant, at least one implant size, at least one arthroplasty surgical procedure, at least one position for implanting the at least one implant in the joint, or any combination thereof. The processor 45 may be further configured to generate a reconstruction plan of the joint of the patient based at least in part on the plurality of PVG corrected medical images of the joint, the at least one implant complication risk assessment, and the at least one arthroplasty surgical parameter, and to input the pre-operative patient specific data and reconstruction plan data into at least one postoperative joint performance machine learning model to determine a predicted post-operative joint performance data output at a plurality of post-operative timepoints after surgery. The predicted post-operative joint performance data output may include but is not limited to a predicted range of movement for the at least one type of joint movement of the joint, and/or at least one predicted pain metric associated with the joint. The at least one postoperative joint performance machine learning model may be trained to output data that may include a plurality of values for the predicted post-operative joint performance data output at the plurality of post-operative timepoints after surgery, each value is at a particular timepoint of the plurality of post-operative timepoints after surgery. The input data to train the at least one postoperative joint performance machine learning model may include but is not limited to the pre-operative patient specific data, the at least one implant complication risk assessment, the at least one region of interest in the portion of the joint, and/or the reconstruction plan data. The processor 45 may be further configured to display on the display 75 to the user 20 (e.g., a doctor, for example), the reconstruction plan data and the predicted post-operative joint performance data output at the plurality of post-operative timepoints after the arthroplasty surgery and perform the arthroplasty surgery based on the reconstruction plan data and the at least one arthroplasty surgical parameter.

In at least some embodiments, this application may incorporate by reference U.S. Pat. No. 11,490,966 in its entirety. The incorporated disclosure may provide additional technical background, exemplary implementations, and variations that may be applicable to the systems, methods, and algorithms described herein, including but not limited to medical image processing, machine learning model construction and deployment, clinical decision support workflows, and visualization techniques.

FIG. 43 is a flowchart of a method 300 for utilizing radiomic-based measurements (and other image-based measurements) within a clinical decision support tool in accordance with one or more embodiments of the present disclosure. The method 300 may be performed by the processor 45 of the medical computing device 15.

In at least some embodiments, the method 300 may include receiving 310 image data of a plurality of medical images of a portion of a joint acquired from at least one medical imaging device prior to an implantation of at least one implant into the joint of a patient.

In at least some embodiments, the method 300 may include generating 320 a plurality of pixel-voxel granularity (PVG) corrected medical images by applying at least one PVG pre-processing algorithm to the image data of each image from the plurality of medical images, where the applying of the at least one PVG pre-processing algorithm may include: normalizing pixel values in the image data in each medical image by adjusting pixel gray level intensity values within each medical image of the plurality of medical images to a common gray scale, resampling the image data to increase or decrease a number of pixels in each medical image based on a standard voxel size between images; and converting the pixel values in each image to digital pixel values to generate PVG corrected image data for each PVG corrected medical image in the plurality of PVG corrected medical images.

In at least some embodiments, the method 300 may include segmenting 330 the PVG corrected image data of each PVG corrected medical image of the portion of the joint using at least one segmentation algorithm to segment the plurality of PVG corrected medical images to identify at least one region of interest (ROI) in the portion of the joint that is represented by at least one ROI image map boundary and associated with at least one of: at least one bone member of the joint, at least one muscle associated with the joint, or both.

In at least some embodiments, the at least one region of interest (ROI) in the portion of the joint that is represented by at least one ROI image map boundary may also be associated with at least one connective tissue associated with the joint.

In at least some embodiments, the method 300 may include inputting 340 the at least one ROI image map boundary and the PVG corrected image data from the plurality of PVG corrected medical images into at least one medical image analysis machine learning model that is trained to output: at least one image based measurement in the at least one region of interest, and at least one implant complication risk assessment for the implantation of the at least one implant into the joint.

In at least some embodiments, the method 300 may include displaying 350 to a user on a display, at least one three-dimensional (3D) representation of the joint and the at least one implant complication risk assessment based on the plurality of PVG corrected medical images.

The technical problems as described above that highly granular image-based measurements lack intuitive clinical interpretation and consistency across heterogeneous scanners and protocols is solved by the system and methods disclosed herein. The technical solutions related to the lack of interpretability in highly granular image data by first standardizing acquired medical images into analysis-ready volumes. The technical flow may include receiving medical imaging data of a joint and may include applying pixel-voxel granularity preprocessing that may normalize gray-level intensities to a common scale, may resample to a standardized isotropic voxel size, and may convert intensities to discrete digital values for robust feature extraction across scanners and protocols. This preprocessing may produce consistent inputs that may enable downstream analytics to operate on harmonized, high-fidelity image information.

In at least some embodiments, the system may then identify anatomically relevant regions by generating three-dimensional, voxel-aligned label maps that may preserve spacing, orientation, and origin metadata. These label maps may define regions of interest such as bone segments, connective tissues, and muscles, where feature calculations may be constrained to the labeled voxels. From these regions, the system may extract quantitative descriptors that may include shape measures, first-order intensity statistics, and second-order texture metrics, and may further use learned representations and class activation maps to highlight localized patterns that may influence predictions.

In at least some embodiments, the extracted measurements and patient-specific inputs may be analyzed by trained models that may output implant complication risk assessments, prospective class or cluster assignments, and time-phased predictions of postoperative performance. The outputs may be visualized in a surgical planning interface that may include three-dimensional reconstructions with heat maps and adaptive tables, and may include alerts when outlier measurements are linked to decreased function or elevated risk. FIGS. 1, 42, and 43 may highlight this coordinated workflow across modules for preprocessing, segmentation, feature extraction, prediction, visualization, and user interaction.

In at least some embodiments, the clinical decision support flow may be integrated into a method of treatment for arthroplasty. The pre-operative steps may include collecting patient data, acquiring standard-of-care images, and generating risk assessments and predicted outcomes that may guide implant type, size, and positioning. Intraoperatively, the planning outputs and visual overlays may direct attention to regions of concern and may confirm resections and implant placement. Postoperatively, the predicted recovery trajectory (e.g., at different post-operative timepoints) may inform rehabilitation plans and follow-up decisions. By embedding the end-to-end analysis into the treatment pathway, the system may help the surgeon select patient-specific strategies that may reduce complication risk and may improve functional outcomes.

In at least some embodiments, radiomic features may be a defined, standardized subset of image-based features focused on shape, first-order intensity, and texture statistics calculated from segmented ROI voxels. Image-based measurements may include radiomics and may also include learned, geometric, biomechanical, registration-derived, and modality-specific metrics that capture information radiomics may not fully represent.

In at least some embodiments, a method may include receiving, by at least one processor, image data of a plurality of medical images of a portion of a joint acquired from at least one medical imaging device prior to an implantation of at least one implant into the joint of a patient; may include generating, by the at least one processor, a plurality of pixel-voxel granularity (PVG) corrected medical images by applying at least one PVG pre-processing algorithm to the image data of each image from the plurality of medical images; may include that the applying of the at least one PVG pre-processing algorithm may include normalizing pixel values in the image data in each medical image by adjusting pixel gray level intensity values within each medical image of the plurality of medical images to a common gray scale; may include resampling the image data to increase or decrease a number of pixels in each medical image based on a standard voxel size between images; and may include converting the pixel values in each image to digital pixel values to generate PVG corrected image data for each PVG corrected medical image in the plurality of PVG corrected medical images; may include segmenting, by the at least one processor, the PVG corrected image data of each PVG corrected medical image of the portion of the joint using at least one segmentation algorithm to segment the plurality of PVG corrected medical images to identify at least one region of interest (ROI) in the portion of the joint that is represented by at least one ROI image map boundary and associated with at least one of at least one bone member of the joint, at least one muscle associated with the joint, or both; may include inputting, by the at least one processor, the at least one ROI image map boundary and the PVG corrected image data from the plurality of PVG corrected medical images into at least one medical image analysis machine learning model that is trained to output at least one image based measurement in the at least one region of interest, and at least one implant complication risk assessment for the implantation of the at least one implant into the joint; and may include displaying, by the at least one processor, to a user on a display, at least one three-dimensional (3D) representation of the joint and the at least one implant complication risk assessment based on the plurality of PVG corrected medical images.

In at least some embodiments, the at least one region of interest may include at least one of a deltoid muscle, a rotator cuff muscle, a scapula including a glenoid vault and an acromion, and a proximal humerus including a metaphysis and a humeral head.

In at least some embodiments, the at least one image based measurement may include at least one shape feature, at least one first order intensity feature, and at least one second order texture feature, the at least one shape feature may include at least one of volume, surface area, sphericity, flatness, elongation, least axis length, and maximum two dimensional diameter in a row, column, or slice plane.

In at least some embodiments, the at least one PVG pre-processing algorithm may include normalizing the image data by z score normalization, resampling to an isotropic voxel size using an interpolation method, may include at least one of B spline or Welch Sinc interpolation, and discretizing the pixel gray level intensity values using at least one of a fixed bin width or a fixed bin count.

In at least some embodiments, the at least one implant complication risk assessment may include a predicted probability of occurrence of at least one complication selected from instability, aseptic loosening, bone fracture, infection, or revision within a defined postoperative time window.

In at least some embodiments, the method may include comparing, by the at least one processor, the at least one image based measurement and/or radiomic feature to a reference cohort to identify an outlier measurement based on a pre-defined statistical threshold; and may include generating, by the at least one processor, an alert in response to the outlier measurement being associated with a decreased functional performance or an increased complication risk.

In at least some embodiments, displaying the at least one 3D representation of the joint may include overlaying at least one of a heat map, a class activation map, or a color-coded indicator on the at least one region of interest to visualize at least one of the at least one radiomic feature, the outlier measurement, or the at least one implant complication risk assessment.

In at least some embodiments, the method may include, by the at least one processor, assigning the patient to at least one pre-defined classification selected from a plurality of machine learned classes derived from image-based measurements, and the at least one implant complication risk assessment may be conditioned on the at least one pre-defined classification.

In at least some embodiments, the at least one medical image analysis machine learning model may include a trained predictive model configured to generate the at least one implant complication risk assessment based at least in part on the at least one radiomic feature and one or more patient specific inputs may include at least one of age, sex, diagnosis, comorbidities, range of motion, or pain score.

In at least some embodiments, the method may include receiving, by the at least one processor, pre-operative patient specific data and at least one arthroplasty surgical parameter, may include generating a reconstruction plan of the joint based at least in part on the plurality of PVG corrected medical images and the at least one implant complication risk assessment, and may include displaying the reconstruction plan on the display.

In at least some embodiments, the method may include inputting, by the at least one processor, the pre-operative patient specific data, the at least one region of interest, and the reconstruction plan into at least one postoperative joint performance model trained to output a predicted postoperative range of motion and at least one predicted postoperative pain metric at a plurality of postoperative timepoints.

In at least some embodiments, the at least one medical imaging device may include a computed tomography scanner, and the plurality of PVG corrected medical images may include Hounsfield unit calibrated volumes.

In at least some embodiments, discretizing the pixel gray level intensity values may include selecting a fixed bin width in Hounsfield unit increments and may include mapping the plurality of PVG corrected medical images to selected bins prior to image based measurement extraction and/or radiomic feature extraction.

In at least some embodiments, the resampling of the image data may include resampling the image data to an isotropic voxel size between 0.5 mm and 1.5 mm.

In at least some embodiments, the method may include receiving, by the at least one processor, pre-operative patient specific data for an arthroplasty surgery to implant the at least one implant in the joint of the patient; may include that the pre-operative patient specific data may include a medical history of the patient, a measured range of movement for at least one type of joint movement of the joint, and at least one pain metric associated with the joint; may include receiving, by the at least one processor, from the user, at least one arthroplasty surgical parameter based on the at least one implant complication risk assessment; may include that the at least one arthroplasty surgical parameter may be selected from the at least one implant, at least one implant size, at least one arthroplasty surgical procedure, at least one position for implanting the at least one implant in the joint, or any combination thereof; may include generating, by the at least one processor, a reconstruction plan of the joint of the patient based at least in part on the plurality of PVG corrected medical images of the joint, the at least one implant complication risk assessment, and the at least one arthroplasty surgical parameter; may include inputting, by the at least one processor, the pre-operative patient specific data and reconstruction plan data into at least one postoperative joint performance machine learning model to determine a predicted post-operative joint performance data output at a plurality of post-operative timepoints after surgery; may include that the predicted post-operative joint performance data output may include at least a predicted range of movement for the at least one type of joint movement of the joint, and at least one predicted pain metric associated with the joint; may include that the at least one postoperative joint performance machine learning model may be trained to output data may include a plurality of values for the predicted post-operative joint performance data output at the plurality of post-operative timepoints after surgery, each value may be at a particular timepoint of the plurality of post-operative timepoints after surgery; may include that input data to train the at least one postoperative joint performance machine learning model may include at least the pre-operative patient specific data, the at least one implant complication risk assessment, the at least one region of interest in the portion of the joint, and the reconstruction plan data; and may include displaying, by the at least one processor, on the display to the user, the reconstruction plan data and the predicted post-operative joint performance data output at the plurality of post-operative timepoints after the arthroplasty surgery, and may include performing the arthroplasty surgery based on the reconstruction plan data and the at least one arthroplasty surgical parameter.

In at least some embodiments, a system may include at least one processor; and may include a non-transitory memory storing instructions that, when executed by the at least one processor, may cause the at least one processor to receive image data of a plurality of medical images of a portion of a joint acquired from at least one medical imaging device prior to an implantation of at least one implant into the joint of a patient; may include generating a plurality of pixel-voxel granularity (PVG) corrected medical images by applying at least one PVG pre-processing algorithm to the image data of each image from the plurality of medical images; may include that the at least one PVG pre-processing algorithm may be configured to normalize pixel values in the image data in each medical image by adjusting pixel gray level intensity values within each medical image of the plurality of medical images to a common gray scale; may include resampling the image data to increase or decrease a number of pixels in each medical image based on a standard voxel size between images; and may include converting the pixel values in each image to digital pixel values to generate PVG corrected image data for each PVG corrected medical image in the plurality of PVG corrected medical images; may include segmenting the PVG corrected image data of each PVG corrected medical image of the portion of the joint using at least one segmentation algorithm to segment the plurality of PVG corrected medical images to identify at least one region of interest (ROI) in the portion of the joint that is represented by at least one ROI image map boundary and associated with at least one of at least one bone member of the joint, at least one muscle associated with the joint, or both; may include inputting the at least one ROI image map boundary and the PVG corrected image data from the plurality of PVG corrected medical images into at least one medical image analysis machine learning model that is trained to output at least one image based measurement in the at least one region of interest, and at least one implant complication risk assessment for the implantation of the at least one implant into the joint; and may include displaying to a user on a display at least one 3-dimensional (3D) representation of the joint and the at least one implant complication risk assessment based on the plurality of PVG corrected medical images.

In at least some embodiments, the at least one region of interest of the system may include at least one of a deltoid muscle, a rotator cuff muscle, a scapula including a glenoid vault and an acromion, and a proximal humerus including a metaphysis and a humeral head.

In at least some embodiments, the at least one image based measurement and/or at least one radiomic feature of the system may include at least one shape feature, at least one first order intensity feature, and at least one second order texture feature, the at least one shape feature may include at least one of volume, surface area, sphericity, flatness, elongation, least axis length, and maximum two dimensional diameter in a row, column, or slice plane.

In at least some embodiments, the at least one PVG pre-processing algorithm of the system may be configured to normalize the image data by z-score normalization, to resample to an isotropic voxel size using an interpolation method may include at least one of B-spline or Welch-Sinc interpolation, and to discretize the pixel gray level intensity values using at least one of a fixed bin width or a fixed bin count.

In at least some embodiments, the at least one implant complication risk assessment of the system may include a predicted probability of occurrence of at least one complication selected from instability, aseptic loosening, bone fracture, infection, or revision within a defined postoperative time window.

In at least some embodiments, the at least one processor of the system may include comparing at least one of the image based measurements to a reference cohort to identify an outlier measurement based on a pre-defined statistical threshold and may include generating an alert in response to the outlier measurement being associated with a decreased functional performance or an increased complication risk.

In at least some embodiments, the at least one processor of the system may include displaying the at least one 3D representation of the joint by overlaying at least one of a heat map, a class activation map, or a color coded indicator on the at least one region of interest to visualize at least one of the at least one image based measurement, the outlier measurement, or the implant complication risk assessment.

In at least some embodiments, the at least one processor of the system may include assigning the patient to at least one pre-defined classification selected from a plurality of machine learned classes derived from image-based measurements, and the at least one implant complication risk assessment may be conditioned on the assigned classification.

In at least some embodiments, the at least one medical image analysis machine learning model of the system may include a trained predictive model configured to generate the at least one implant complication risk assessment based at least in part on the at least one image based measurement and one or more patient specific inputs may include at least one of age, sex, diagnosis, comorbidities, range of motion, or pain score.

In at least some embodiments, the at least one processor of the system may include receiving preoperative patient specific data and at least one arthroplasty surgical parameter, may include generating a reconstruction plan of the joint based at least in part on the PVG corrected medical images and the at least one implant complication risk assessment, and may include displaying the reconstruction plan on the display.

In at least some embodiments, the at least one processor of the system may include inputting the preoperative patient specific data, the at least one region of interest, and the reconstruction plan into at least one postoperative joint performance model trained to output a predicted postoperative range of motion and at least one predicted postoperative pain metric at a plurality of postoperative timepoints.

In at least some embodiments, the at least one medical imaging device of the system may include a computed tomography scanner, and the plurality of PVG corrected medical images may include Hounsfield unit calibrated volumes.

In at least some embodiments, discretizing the pixel gray level intensity values of the system may include selecting a fixed bin width in Hounsfield unit increments and may include mapping the PVG corrected medical images to the selected bins prior to image based measurement and/or radiomic feature extraction.

In at least some embodiments, the at least one PVG pre-processing algorithm of the system may be configured to resample the image data by resampling the image data to an isotropic voxel size between 0.5 mm and 1.5 mm.

In at least some embodiments, the at least one image based measurement may include at least one radiomic feature.

In at least some embodiments, the at least one processor of the system may include receiving pre-operative patient specific data for an arthroplasty surgery to implant the at least one implant in the joint of the patient; may include that the pre-operative patient specific data may include a medical history of the patient, a measured range of movement for at least one type of joint movement of the joint, and at least one pain metric associated with the joint; may include receiving from the user, at least one arthroplasty surgical parameter based on the at least one implant complication risk assessment; may include that the at least one arthroplasty surgical parameter may be selected from the at least one implant, at least one implant size, at least one arthroplasty surgical procedure, at least one position for implanting the at least one implant in the joint, or any combination thereof, may include generating a reconstruction plan of the joint of the patient based at least in part on the plurality of PVG corrected medical images of the joint, the at least one implant complication risk assessment, and the at least one arthroplasty surgical parameter; may include inputting the pre-operative patient specific data and reconstruction plan data into at least one postoperative joint performance machine learning model to determine a predicted post-operative joint performance data output at a plurality of post-operative timepoints after surgery; may include that the predicted post-operative joint performance data output may include at least a predicted range of movement for the at least one type of joint movement of the joint, and at least one predicted pain metric associated with the joint; may include that the at least one postoperative joint performance machine learning model may be trained to output data may include a plurality of values for the predicted post-operative joint performance data output at the plurality of post-operative timepoints after surgery, each value may be at a particular timepoint of the plurality of post-operative timepoints after surgery; may include that input data to train the at least one postoperative joint performance machine learning model may include at least the pre-operative patient specific data, the at least one implant complication risk assessment, the at least one region of interest in the portion of the joint, and the reconstruction plan data; and may include displaying on the display to the user, the reconstruction plan data and the predicted post-operative joint performance data output at the plurality of post-operative timepoints after the arthroplasty surgery and may include performing the arthroplasty surgery based on the reconstruction plan data and the at least one arthroplasty surgical parameter.

In at least some embodiments, exemplary inventive, specially programmed computing systems/platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes. In at least some embodiments, the NFC can represent a short-range wireless communications technology in which NFC-enabled devices are "swiped," "bumped," "tap" or otherwise moved in close proximity to communicate. In at least some embodiments, the NFC could include a set of short-range wireless technologies, typically requiring a distance of 10 cm or less. In at least some embodiments, the NFC may operate at 13.56 MHz on ISO/IEC 18000-3 air interface and at rates ranging from 106 kbit/s to 424 kbit/s. In at least some embodiments, the NFC can involve an initiator and a target; the initiator actively generates an RF field that can power a passive target. In at least some embodiments, this can enable NFC targets to take very simple form factors such as tags, stickers, key fobs, or cards that do not require batteries. In at least some embodiments, the NFC's peer-to-peer communication can be conducted when a plurality of NFC-enable devices (e.g., smartphones) within close proximity of each other.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In at least some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In at least some embodiments, one or more of exemplary inventive computer-based systems/platforms, exemplary inventive computer-based devices, and/or exemplary inventive computer-based components of the present disclosure such as the computing device 77 may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In at least some embodiments, as detailed herein, one or more of exemplary inventive computer-based systems/platforms, exemplary inventive computer-based devices, and/or exemplary inventive computer-based components of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a social media post, a map, an entire application (e.g., a calculator), etc. In at least some embodiments, as detailed herein, one or more of exemplary inventive computer-based systems/platforms, exemplary inventive computer-based devices, and/or exemplary inventive computer-based components of the present disclosure may be implemented across one or more of various computer platforms such as, but not limited to: (1) FreeBSD, NetBSD, OpenBSD; (2) Linux; (3) Microsoft Windows; (4) OS X (MacOS); (5) MacOS 11; (6) Solaris; (7) Android; (8) iOS; (9) Embedded Linux; (10) Tizen; (11) WebOS; (12) IBM i; (13) IBM AIX; (14) Binary Runtime Environment for Wireless (BREW); (15) Cocoa (API); (16) Cocoa Touch; (17) Java Platforms; (18) JavaFX; (19) JavaFX Mobile; (20) Microsoft DirectX; (21).NET Framework; (22) Silverlight; (23) Open Web Platform; (24) Oracle Database; (25) Qt; (26) Eclipse Rich Client Platform; (27) SAP NetWeaver; (28) Smartface; and/or (29) Windows Runtime.

In at least some embodiments, exemplary inventive computer-based systems/platforms, exemplary inventive computer-based devices, and/or exemplary inventive computer-based components of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In at least some embodiments, exemplary inventive computer-based systems/platforms, exemplary inventive computer-based devices, and/or exemplary inventive computer-based components of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In at least some embodiments, exemplary inventive computer-based systems/platforms, exemplary inventive computer-based devices, and/or exemplary inventive computer-based components of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, and/or objects. For example, such projections may be a visual overlay for a mobile augmented reality (MAR) application.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In at least some embodiments, the exemplary inventive computer-based systems/platforms, the exemplary inventive computer-based devices, and/or the exemplary inventive computer-based components of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIP-EMD-160, RTRO, SHA-1, SHA-2, Tiger (TTH), WHIRL-POOL, RNGs).

The aforementioned examples are, of course, illustrative and not restrictive.

As used herein, the term "user" shall have a meaning of at least one user. In the context as used herein, the user may be a doctor, or a surgeon or someone acting on behalf of the doctor, or surgeon, a laboratory technician, surgical staff, and the like.

In at least some embodiments, the exemplary inventive computer-based systems/platforms, the exemplary inventive computer-based devices, and/or the exemplary inventive computer-based components of the present disclosure may be configured to utilize one or more exemplary AI/machine learning techniques chosen from, but not limited to, decision trees, boosting, support-vector machines, neural networks, nearest neighbor algorithms, Naïve Bayes, bagging, random forests, and the like. In at least some embodiments and, optionally, in combination of any embodiment described above or below, an exemplary neutral network technique may be one of, without limitation, feedforward neural network, radial basis function network, recurrent neural network, convolutional network (e.g., U-net) or other suitable network. In at least some embodiments and, optionally, in combination of any embodiment described above or below, an exemplary implementation of Neural Network may be executed as follows:

i) Define Neural Network architecture/model,
ii) Transfer the input data to the exemplary neural network model,
iii) Train the exemplary model incrementally,
iv) determine the accuracy for a specific number of timesteps,
v) apply the exemplary trained model to process the newly-received input data,
vi) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In at least some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated. In at least some embodiments and, optionally, in combination of any embodiment described above or below, the exemplary aggregation function may be a mathematical function that combines (e.g., sum, product, etc.) input signals to the node. In at least some embodiments and, optionally, in combination of any embodiment described above or below, an output of the exemplary aggregation function may be used as input to the exemplary activation function. In at least some embodiments and, optionally, in combination of any embodiment described above or below, the bias may be a constant value or function that may be used by the aggregation function and/or the activation function to make the node more or less likely to be activated.

The disclosure described herein may be practiced in the absence of any element or elements, limitation or limitations, which is not specifically disclosed herein. Thus, for example, in each instance herein, any of the terms "comprising," "consisting essentially of and "consisting of" may be replaced with either of the other two terms, without altering their respective meanings as defined herein. The terms and expressions which have been employed are used as terms of description and not of limitation, and there is no intention in the use of such terms and expressions of excluding any equivalents of the features shown and described or portions thereof, but it is recognized that various modifications are possible within the scope of the disclosure.

The invention claimed is:

1. A method, comprising:

receiving, by at least one processor, image data of a plurality of medical images of a portion of a joint acquired from at least one medical imaging device prior to an implantation of at least one implant into the joint of a patient;

generating, by the at least one processor, a plurality of pixel-voxel granularity (PVG) corrected medical images by applying at least one PVG pre-processing algorithm to the image data of each image from the plurality of medical images;

wherein the applying of the at least one PVG pre-processing algorithm comprises:

normalizing pixel values in the image data in each medical image by adjusting pixel gray level intensity values within each medical image of the plurality of medical images to a common gray scale;

resampling the image data to increase or decrease a number of pixels in each medical image based on a standard voxel size between images; and converting the pixel values in each image to digital pixel values to generate PVG corrected image data for each PVG corrected medical image in the plurality of PVG corrected medical images;

segmenting, by the at least one processor, the PVG corrected image data of each PVG corrected medical image of the portion of the joint using at least one segmentation algorithm to segment the plurality of PVG corrected medical images to identify at least one region of interest (ROI) in the portion of the joint that is represented by at least one ROI image map boundary and associated with at least one of:

at least one bone member of the joint, at least one muscle associated with the joint, or both;

inputting, by the at least one processor, the at least one ROI image map boundary and the PVG corrected image data from the plurality of PVG corrected medical images into at least one medical image analysis machine learning model that is trained to output:

at least one image based measurement in the at least one region of interest, and at least one implant complication risk assessment for the implantation of the at least one implant into the joint; and displaying, by the at least one processor, to a user on a display, at least one three-dimensional (3D) representation of the joint and the at least one implant complication risk assessment based on the plurality of PVG corrected medical images.

2. The method of claim 1, wherein the at least one region of interest comprises at least one of: a deltoid muscle, a rotator cuff muscle, a scapula including a glenoid vault and an acromion, and a proximal humerus including a metaphysis and a humeral head.

3. The method of claim 1, wherein the at least one image based measurement comprises at least one shape feature, at least one first-order intensity feature, and at least one second-order texture feature, the at least one shape feature comprising at least one of volume, surface area, sphericity, flatness, elongation, least axis length, and maximum two-dimensional diameter in a row, column, or slice plane.

4. The method of claim 1, wherein the at least one PVG pre-processing algorithm comprises normalizing the image data by z-score normalization, resampling to an isotropic voxel size using an interpolation method, comprising at least one of: B-spline or Welch-Sinc interpolation, and discretizing the pixel gray level intensity values using at least one of: a fixed bin width or a fixed bin count.

5. The method of claim 1, wherein the at least one implant complication risk assessment comprises a predicted probability of occurrence of at least one complication selected from instability, aseptic loosening, bone fracture, infection, or revision within a defined postoperative time window.

6. The method of claim 1, further comprising comparing, by the at least one processor, the at least one image based measurement to a reference cohort to identify an outlier measurement based on a pre-defined statistical threshold; and generating, by the at least one processor, an alert in response to the outlier measurement being associated with a decreased functional performance or an increased complication risk.

7. The method of claim 6, wherein displaying the at least one 3D representation of the joint comprises overlaying at least one of a heat map, a class activation map, or a color-coded indicator on the at least one region of interest to visualize at least one of the at least one image based measurement, the outlier measurement, or the at least one implant complication risk assessment.

8. The method of claim 1, further comprising, by the at least one processor, assigning the patient to at least one pre-defined classification selected from a plurality of machine-learned classes derived from image-based measurements, and wherein the at least one implant complication risk assessment is conditioned on the at least one pre-defined classification.

9. The method of claim 1, wherein the at least one medical image analysis machine learning model comprises a trained predictive model configured to generate the at least one implant complication risk assessment based at least in part on the at least one image based measurement and one or more patient-specific inputs comprising at least one of: age, sex, diagnosis, comorbidities, range of motion, or pain score.

10. The method of claim 1, further comprising receiving, by the at least one processor, pre-operative patient-specific data and at least one arthroplasty surgical parameter, generating a reconstruction plan of the joint based at least in part on the plurality of PVG corrected medical images and the at least one implant complication risk assessment, and displaying the reconstruction plan on the display.

11. The method of claim 10, further comprising inputting, by the at least one processor, the pre-operative patient-specific data, the at least one region of interest, and the reconstruction plan into at least one postoperative joint performance model trained to output a predicted postoperative range of motion and at least one predicted postoperative pain metric at a plurality of postoperative timepoints.

12. The method of claim 1, wherein the at least one medical imaging device comprises a computed tomography scanner, and the plurality of PVG corrected medical images comprise Hounsfield-unit calibrated volumes.

13. The method of claim 1, wherein discretizing the pixel gray level intensity values comprises selecting a fixed bin width in Hounsfield-unit increments and mapping the plurality of PVG corrected medical images to selected bins prior to image based feature extraction.

14. The method of claim 1, wherein the resampling of the image data comprises resampling the image data to an isotropic voxel size between 0.5 mm and 1.5 mm.

15. The method of claim 1, wherein the at least one image based measurement comprises at least one radiomic feature.

16. The method of claim 1, further comprising receiving, by the at least one processor, pre-operative patient specific data for an arthroplasty surgery to implant the at least one implant in the joint of the patient;

wherein the pre-operative patient specific data comprises:

a medical history of the patient, a measured range of movement for at least one type of joint movement of the joint, and at least one pain metric associated with the joint;

receiving, by the at least one processor, from the user, at least one arthroplasty surgical parameter based on the at least one implant complication risk assessment;

wherein the at least one arthroplasty surgical parameter is selected from:

the at least one implant, at least one implant size, at least one arthroplasty surgical procedure, at least one position for implanting the at least one implant in the joint, or any combination thereof;

generating, by the at least one processor, a reconstruction plan of the joint of the patient based at least in part on the plurality of PVG corrected medical images of the joint, the at least one implant complication risk assessment, and the at least one arthroplasty surgical parameter;

inputting, by the at least one processor, the pre-operative patient specific data and reconstruction plan data into at least one postoperative joint performance machine learning model to determine a predicted post-operative joint performance data output at a plurality of post-operative timepoints after surgery;

wherein the predicted post-operative joint performance data output comprises at least:

a predicted range of movement for the at least one type of joint movement of the joint, and at least one predicted pain metric associated with the joint;

wherein the at least one postoperative joint performance machine learning model is trained to output data comprising a plurality of values for the predicted post-operative joint performance data output at the plurality of post-operative timepoints after surgery, each value is at a particular timepoint of the plurality of post-operative timepoints after surgery;

wherein input data to train the at least one postoperative joint performance machine learning model comprises at least:

the pre-operative patient specific data, the at least one implant complication risk assessment, the at least one region of interest in the portion of the joint, and the reconstruction plan data; and displaying, by the at least one processor, on the display to the user, the reconstruction plan data and the predicted post-operative joint performance data output at the plurality of post-operative timepoints after the arthroplasty surgery, and performing the arthroplasty surgery based on the reconstruction plan data and the at least one arthroplasty surgical parameter.

17. A system, comprising:

at least one processor; and a non-transitory memory storing instructions that, when executed by the at least one processor, cause the at least one processor to:

receive image data of a plurality of medical images of a portion of a joint acquired from at least one medical imaging device prior to an implantation of at least one implant into the joint of a patient;

generate a plurality of pixel-voxel granularity (PVG) corrected medical images by applying at least one PVG pre-processing algorithm to the image data of each image from the plurality of medical images;

wherein the at least one PVG pre-processing algorithm is configured to:

normalize pixel values in the image data in each medical image by adjusting pixel gray level intensity values within each medical image of the plurality of medical images to a common gray scale;

resample the image data to increase or decrease a number of pixels in each medical image based on a standard voxel size between images; and convert the pixel values in each image to digital pixel values to generate PVG corrected image data for each PVG corrected medical image in the plurality of PVG corrected medical images;

segment the PVG corrected image data of each PVG corrected medical image of the portion of the joint using at least one segmentation algorithm to segment the plurality of PVG corrected medical images to identify at least one region of interest (ROI) in the portion of the joint that is represented by at least one ROI image map boundary and associated with at least one of:

at least one bone member of the joint, at least one muscle associated with the joint, or both;

input the at least one ROI image map boundary and the PVG corrected image data from the plurality of PVG corrected medical images into at least one medical image analysis machine learning model that is trained to output:

at least one image based measurement in the at least one region of interest, and at least one implant complication risk assessment for the implantation of the at least one implant into the joint; and display to a user on a display at least one 3-dimensional (3D) representation of the joint and the at least one implant complication risk assessment based on the plurality of PVG corrected medical images.

18. The system of claim 17, wherein the at least one region of interest comprises at least one of: a deltoid muscle, a rotator cuff muscle, a scapula including a glenoid vault and an acromion, and a proximal humerus including a metaphysis and a humeral head.

19. The system of claim 17, wherein the at least one image based measurement comprises at least one shape feature, at least one first order intensity feature, and at least one second order texture feature, the at least one shape feature comprising at least one of volume, surface area, sphericity, flatness, elongation, least axis length, and maximum two dimensional diameter in a row, column, or slice plane.

20. The system of claim 17, wherein the at least one PVG pre-processing algorithm is configured to normalize the image data by z-score normalization, to resample to an isotropic voxel size using an interpolation method comprising at least one of B-spline or Welch-Sinc interpolation, and to discretize the pixel gray level intensity values using at least one of: a fixed bin width or a fixed bin count.

21. The system of claim 17, wherein the at least one implant complication risk assessment comprises a predicted probability of occurrence of at least one complication selected from instability, aseptic loosening, bone fracture, infection, or revision within a defined postoperative time window.

22. The system of claim 17, wherein the at least one processor is further configured to compare the at least one image based measurement to a reference cohort to identify an outlier measurement based on a pre-defined statistical threshold, and to generate an alert in response to the outlier measurement being associated with a decreased functional performance or an increased complication risk.

23. The system of claim 22, wherein the at least one processor is configured to display the at least one 3D representation of the joint by overlaying at least one of a heat map, a class activation map, or a color coded indicator on the at least one region of interest to visualize at least one of the at least one image based measurement, the outlier measurement, or the implant complication risk assessment.

24. The system of claim 17, wherein the at least one processor is further configured to assign the patient to at least one pre-defined classification selected from a plurality of machine learned classes derived from image-based measurements, and wherein the at least one implant complication risk assessment is conditioned on the assigned classification.

25. The system of claim 17, wherein the at least one medical image analysis machine learning model comprises a trained predictive model configured to generate the at least one implant complication risk assessment based at least in part on the at least one image based measurement and one or more patient specific inputs comprising at least one of: age, sex, diagnosis, comorbidities, range of motion, or pain score.

26. The system of claim 17, wherein the at least one processor is further configured to receive preoperative patient specific data and at least one arthroplasty surgical parameter, to generate a reconstruction plan of the joint based at least in part on the PVG corrected medical images and the at least one implant complication risk assessment, and to display the reconstruction plan on the display.

27. The system of claim 26, wherein the at least one processor is further configured to input the preoperative patient specific data, the at least one region of interest, and the reconstruction plan into at least one postoperative joint performance model trained to output a predicted postoperative range of motion and at least one predicted postoperative pain metric at a plurality of postoperative timepoints.

28. The system of claim 17, wherein the at least one medical imaging device comprises a computed tomography scanner, and the plurality of PVG corrected medical images comprise Hounsfield unit calibrated volumes.

29. The system of claim 17, wherein the at least one PVG pre-processing algorithm is configured to resample the image data by resampling the image data to an isotropic voxel size between 0.5 mm and 1.5 mm.

30. The system of claim 17, wherein the at least one processor is further configured to:

receive pre-operative patient specific data for an arthroplasty surgery to implant the at least one implant in the joint of the patient;

wherein the pre-operative patient specific data comprises:

a medical history of the patient, a measured range of movement for at least one type of joint movement of the joint, and at least one pain metric associated with the joint;

receive from the user, at least one arthroplasty surgical parameter based on the at least one implant complication risk assessment;

wherein the at least one arthroplasty surgical parameter is selected from:

the at least one implant, at least one implant size, at least one arthroplasty surgical procedure, at least one position for implanting the at least one implant in the joint, or any combination thereof;

generate a reconstruction plan of the joint of the patient based at least in part on the plurality of PVG corrected medical images of the joint, the at least one implant complication risk assessment, and the at least one arthroplasty surgical parameter;

input the pre-operative patient specific data and reconstruction plan data into at least one postoperative joint performance machine learning model to determine a predicted post-operative joint performance data output at a plurality of post-operative timepoints after surgery;

wherein the predicted post-operative joint performance data output comprises at least:

a predicted range of movement for the at least one type of joint movement of the joint, and at least one predicted pain metric associated with the joint;

wherein the at least one postoperative joint performance machine learning model is trained to output data comprising a plurality of values for the predicted post-operative joint performance data output at the plurality of post-operative timepoints after surgery, each value is at a particular timepoint of the plurality of post-operative timepoints after surgery;

wherein input data to train the at least one postoperative joint performance machine learning model comprises at least:

the pre-operative patient specific data, the at least one implant complication risk assessment, the at least one region of interest in the portion of the joint, and the reconstruction plan data; and display on the display to the user, the reconstruction plan data and the predicted post-operative joint performance data output at the plurality of post-operative timepoints after the arthroplasty surgery and perform the arthroplasty surgery based on the reconstruction plan data and the at least one arthroplasty surgical parameter.

* * * * *